(12) United States Patent
Okamoto et al.

(10) Patent No.: US 6,673,316 B1
(45) Date of Patent: Jan. 6, 2004

(54) SYNTHESIS EXPERIMENT AUTOMATING SYSTEM, LIQUID SEPARATING TREATING APPARATUS AND REACTION VESSEL

(75) Inventors: Hideho Okamoto, Otsu (JP); Kouji Deuchi, Ibaraki (JP); Hirokazu Murata, Duesseldorf (DE); Norihiko Hirata, Suita (JP); Toshio Koike, Yokohama (JP); Kenji Tani, Shiki (JP); Yasuharu Kawata, Yokohama (JP); Hideto Tojima, Kyoto (JP)

(73) Assignee: Sumitomo Chemical Co., Ltd., Osaka (JP)

( * ) Notice: Subject to any disclaimer, the term of this patent is extended or adjusted under 35 U.S.C. 154(b) by 0 days.

(21) Appl. No.: 09/091,877
(22) PCT Filed: Oct. 27, 1997
(86) PCT No.: PCT/JP97/03902
§ 371 (c)(1),
(2), (4) Date: Jun. 26, 1998
(87) PCT Pub. No.: WO98/18549
PCT Pub. Date: May 7, 1998

(30) Foreign Application Priority Data

| Oct. 30, 1996 | (JP) | 8-288708 |
| Jul. 18, 1997 | (JP) | 9-194506 |
| Jul. 31, 1997 | (JP) | 9-206881 |

(51) Int. Cl.$^7$ ............................................. B32B 27/04
(52) U.S. Cl. .......................... 422/63; 422/65; 422/102; 422/130
(58) Field of Search ............................ 422/63, 65, 100, 422/102, 82.02, 82.05, 106, 138, 130, 135; 436/47, 48, 49, 54, 139, 150, 164, 165, 174, 180

(56) References Cited

U.S. PATENT DOCUMENTS 4,006,062 A * 2/1977 Bhuchar et al. ............ 202/169
4,242,301 A * 12/1980 Heyneman et al. ......... 422/68
4,578,764 A    3/1986 Hutchins et al.

(List continued on next page.)

FOREIGN PATENT DOCUMENTS

| EP | 510 487 | 10/1992 | |
| EP | 628822 A2 * | 12/1994 | G01N/35/02 |
| JP | 54-102158 | 8/1979 | |

(List continued on next page.)

OTHER PUBLICATIONS

Valcarcel M. et al., 1989, Automatic Methods of Anaysis Techniques and Instrumentation in Analytical Chemistry, vol. 9, Elsevier. pp. 252.*

"Flexible laboratory automation to meet the challenge of the '90s " (J. Gentsch, chemometrics and Intelligent Laboratory Systems: Laboratory Information Management, 21(1993), pp. 229–233).

(List continued on next page.)

*Primary Examiner*—Jill Warden
(74) *Attorney, Agent, or Firm*—Fitch, Even, Tabin & Flannery

(57) ABSTRACT

A synthesis experiment automation system is provided with a robot, which transports synthesis reaction containers from a reaction container rack to a dispensing/separation position of a dispensing and separation device, and transports the synthesis reaction containers to a predetermined position in a temperature regulator unit of a reaction device, where a reaction is carried out under previously set experiment conditions; and with a computer, which controls the actions of the robot and the operations of the dispensing and separation device and the reaction device in accordance with a plurality of previously set experiment conditions. Accordingly, the synthesis experiment automation system is capable of simultaneously performing a plurality of different experiments as complex as those usually performed by researchers, and, moreover, has a large number of possible experiment operations, and can easily be improved and/or extended.

8 Claims, 39 Drawing Sheets

U.S. PATENT DOCUMENTS

| | | | | |
|---|---|---|---|---|
| 4,738,824 | A | * | 4/1988 | Takeuchi .................. 422/63 |
| 5,239,484 | A | | 8/1993 | Hayashi et al. |
| 5,380,486 | A | * | 1/1995 | Anami ..................... 422/63 |
| 5,417,922 | A | * | 5/1995 | Markin et al. ............... 42/65 |
| 5,455,008 | A | * | 10/1995 | Earley et al. .............. 422/100 |
| 5,463,564 | A | | 10/1995 | Agrafiotis et al. |
| 5,472,669 | A | * | 12/1995 | Miki et al. ................. 422/63 |
| 5,501,838 | A | * | 3/1996 | Ootani et al. ............... 422/65 |
| 5,525,300 | A | * | 6/1996 | Danssaert et al. ........... 422/99 |
| 5,578,269 | A | * | 11/1996 | Yaremko et al. ............. 422/64 |
| 5,714,127 | A | * | 2/1998 | DeWitt et al. .............. 422/130 |
| 5,716,584 | A | * | 2/1998 | Baker et al. ............... 422/131 |
| 5,928,952 | A | * | 7/1999 | Hutchins et al. ............. 436/50 |
| 5,948,360 | A | * | 9/1999 | Rao et al. .................. 422/65 |
| 6,044,212 | A | * | 3/2000 | Flavin et al. ............... 703/11 |
| 6,045,755 | A | * | 4/2000 | Lebl et al. ................ 422/103 |
| 6,060,022 | A | * | 5/2000 | Pang et al. ................. 422/65 |
| 6,293,750 | B1 | * | 9/2001 | Cohen et al. ............. 414/744.4 |
| 6,299,840 | B1 | * | 10/2001 | Watanabe et al. ............ 422/50 |
| 6,351,690 | B1 | * | 2/2002 | Lenz ....................... 422/100 |

FOREIGN PATENT DOCUMENTS

| | | |
|---|---|---|
| JP | 54/102158/1979 | 8/1979 |
| JP | 60-252268 | 12/1985 |
| JP | 1-249135 | 10/1989 |
| JP | 2-2870 | 1/1990 |
| JP | 02-275362 | 11/1990 |
| JP | 4-204159 | 7/1992 |
| JP | 5-192563 | 8/1993 |
| JP | 5-340670 | 12/1993 |
| JP | 6-63389 | 3/1994 |
| JP | 6-79166 | 3/1994 |
| JP | 6-94728 | 4/1994 |
| JP | 6-221895 | 8/1994 |
| JP | 6-221895/1994 | 8/1994 |
| JP | 07-027769 | 1/1995 |
| JP | 8-29432 | 2/1996 |
| JP | 8-43173 | 2/1996 |
| JP | 8-94412 | 4/1996 |
| JP | 9-133687 | 5/1997 |
| JP | 9-145453 | 6/1997 |
| WO | 92/22801 | 12/1992 |

OTHER PUBLICATIONS

"Automation of organic synthesis in industrial research laboratories" (P. Metivier et al., Chemometrics and Intelligent Laboratory systems: Laboratory Information Management, 17 (1992), pp. 137–143).

"Develop reaction automatically" (Gary W. Kramer et al., CHEMTECH Nov. 1989, pp. 682–688).

"Better Chemistry through Robotics: an Automated System for Process Optimization"(Susan D. Boettger, LRA, vol. 4, 1992, pp. 169–181).

Robotic work station for microscale synthetic chemistry: On–line absorption spectroscopy, quantitative automated thin–layer chromatography, and multiple reactions in parallel (Jonathan s. Lindsey et al., Sci, Instrum,59(6), Jun. 1988, pp. 940–950).

Robotic Automation of Some Common Organic Laboratory Techniques, Gary W. Kramer et al., Advances in Laboratory Automation Robotics, vol. 6, 1989, pp. 339–359.

Valcarcel M. et al., 1989, Automatic Methods of Analysis Techniques and Instrumentation in Analytical Chemistry, vol. 9, Elsevier pp. 258–261.

"Flexible Laboratory Automation To Meet The Challenge of The '90s", (J. Gentsch, Chemometrix and Intelligent Laboratory Systems: Laboratory Information Management, 21(1993), pp. 229–233.

"Automation of Organic Synthesis in Industrial Research Laboratories", P. Metivier et al., Chemometrics and Intelligent Laboratory Systems: Laboratory Information Management, 17(1993), pp. 137–143.

"Develop Reaction Automatically", Gary W. Kramer et al., CHEMTECH Nov. 1989, pp. 682–688.

"Robotic Work Station for Microscale Synthetic Chemistry: On–line Absorption Spectroscopy, Quantitative Automated Thin–Layer Chromatography, and Multiple Reactions in Parallel", Jonathan S. Lindsey et al., Sci, Instrum 59(6), Jun. 1988, pp. 940–950.

"Robotic Automation of Some Common Organic Laboratory Techniques", Gary W. Kramer et al., Advances in Laboratory Automation Robotics, vol. 6, 1989, pp. 339–359.

Susan D. Boettger, LRD, "Better Chemistry Through Robotics: An Automated System for Process Optimization", vol. 4 1992, pp. 169–181.

* cited by examiner

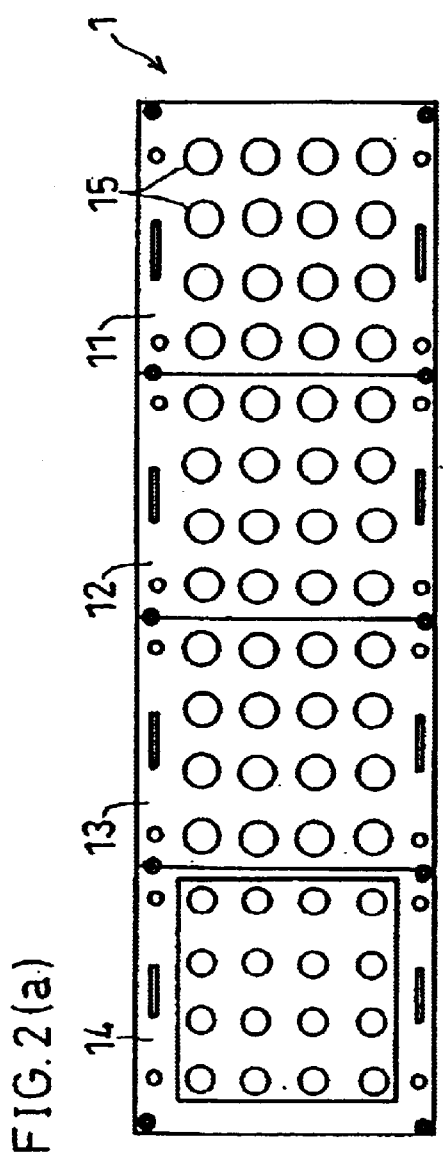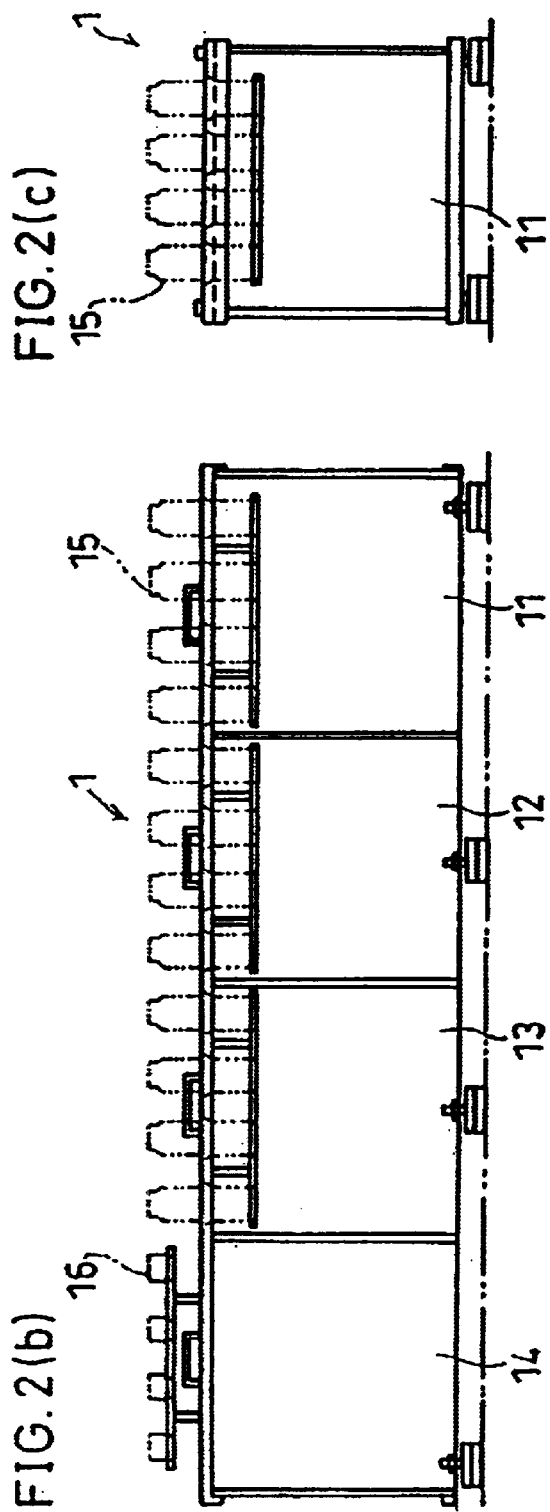

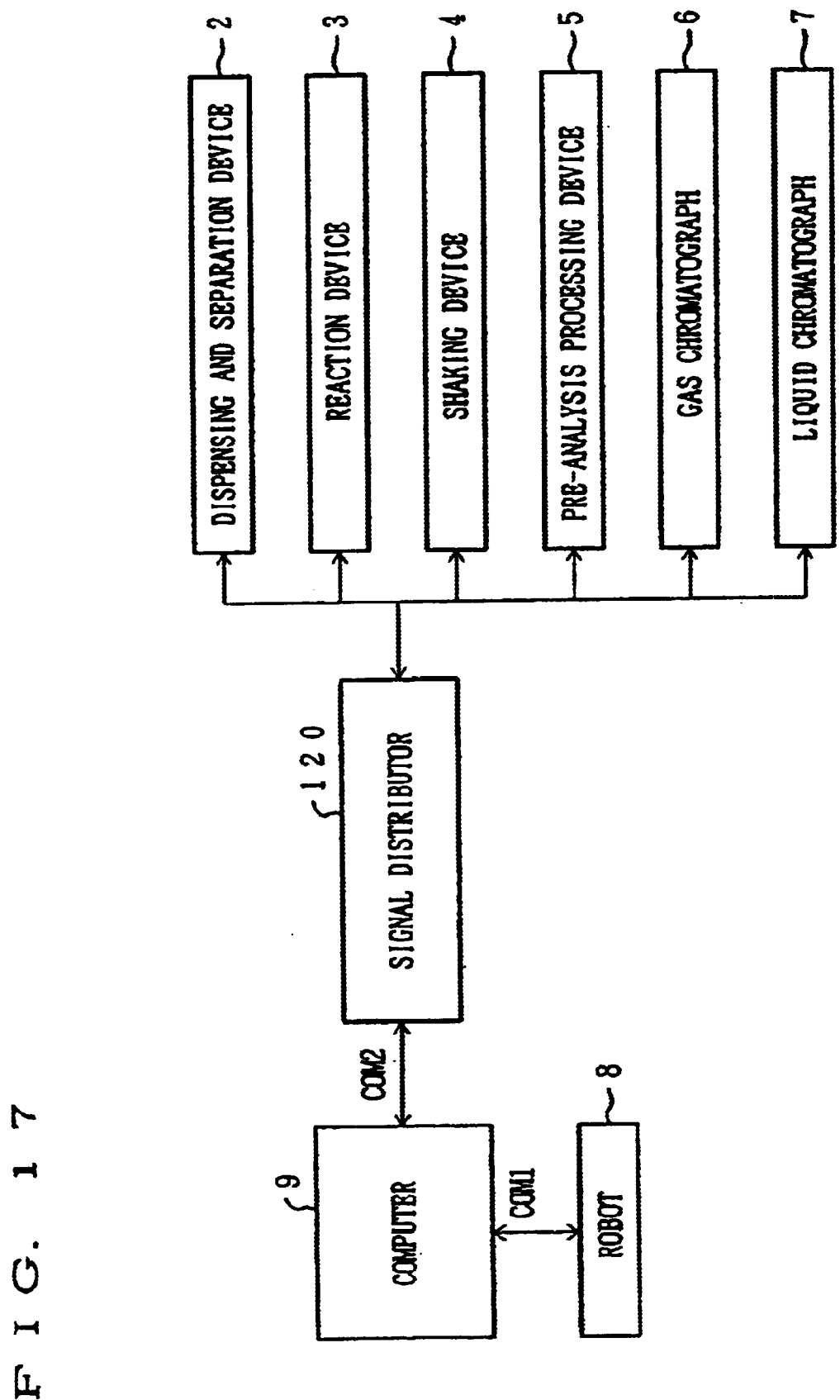

F I G. 1 9
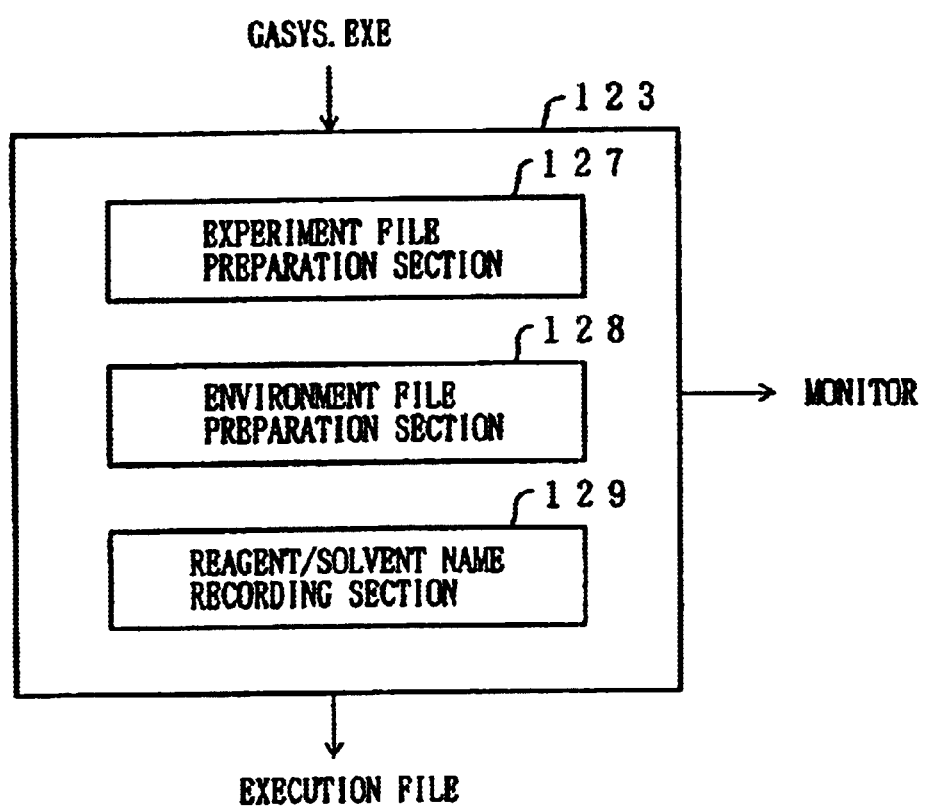

FIG. 23

SEQUENCE SETUP

FILE (F)　EDIT (E)　EXPERIMENT BOTTLE COPY/CLEAR (W)

| 1 | 2 | 3 | 4 | 5 | 6 | 7 | 8 | 9 | 10 | 11 | 12 | 13 | 14 | 15 | 16 |

200

EXIT

--SETUP: EXPERIMENT BOTTLE 1 (2/8)--

1. [ADD SOLVENT (WEIGHED)]
   QUANTITY: 20 (ml)
   PURE WATER

2. [PREP (TEMP. REGULATED)]
   QUANTITY: 1 (ml)
   WATER-ACETONE

3. [PREP (TEMP. REGULATED)]
   QUANTITY: 1 (ml)
   DMF

4. [ADD REAGENT (SEPARATION)]
   QUANTITY: 1 (ml)
   GLYCINONITRILE HYDROCHLORIDE

5. [TEMPERATURE REGULATION]
   25 (°C)

6. [DRIPPING] 10 (MIN.)
   QUANTITY: 1 (ml)
   SODIUM DIHYDROGEN CITRATE

7. [MAINTAIN TEMPERATURE]
   10 (MIN.)

--SEQUENCE (EXECUTION ACTIONS) SETUP--

TEMPERATURE          MAINTAIN
REGURATION           TEMPERATURE
END TEMPERATURE      PREP
REGURATION           (TEMP. REGULATED)
DRIPPING             LET STAND
[SHAKING]            SEPARATION
ANALYSIS             ADD SOLVENT
ADD SOLVENT          (UNWEIGHED)
(WEIGHED)            WEIGHING
ADD REAGENT
(SEPARATION)

2. PREPARATION (TEMP. REGULATED)

UNIT CHANGE

| PARAMETER NAME | MIN. | MAX. | SET VALUE |
|---|---|---|---|
| REAGENT NAME NO. | 101 | 116 | 102 |
| REAGENT QUANTITY | 0.0 | 100.0 | 1 |

EXPERIMENT BOTTLE 1 SETUP

SYNTHESIS EXPERIMENT AUTOMATING SYSTEM, LIQUID SEPARATING TREATING APPARATUS AND REACTION VESSEL

TECHNICAL FIELD

The present invention relates to a synthesis experiment automation system for automating chemical synthesis experiments, and to a liquid level/interface position detecting device, a separation processing device, and a reaction container, which are suitable for use in the synthesis experiment automation system.

BACKGROUND ART

In the past, various automated experiment devices have been developed in order to increase the efficiency of chemical experiments and reduce the effort involved therein.

Automated experiment devices of this kind can be broadly divided into, for example, (1) devices which control reaction conditions by, for example, controlling temperature, pressure, flow, etc., precision measuring of heat balance, and analyzing reaction parameters; (2) sequential devices for synthesizing samples of small quantity by performing synthesis, post-processing, refinement, etc.; and (3) devices which use a robot to perform synthesis, post-processing, and analysis.

Specific examples of these kinds of automated experiment devices are (I) synthesis reaction devices such as those disclosed in Japanese Unexamined Patent Publication Nos. 1-249135/1989 (Tokukaihei 1-249135), 2-2870/1990 (Tokukaihei 2-2870), 6-63389/1994 (Tokukaihei 6-63389), and 6-79166/1994 (Tokukaihei 6-79166); (II) automated synthesis devices such as the Contalab (manufactured by Mettler Co.) and the ARS (manufactured by Sogo Chemical Industries Co., Ltd.); and (III) the synthesis experiment device CombiTec (manufactured by Tecan Co.), which uses a robot.

However, the synthesis reaction devices in (I) above are integral sequence control devices, which conduct a reaction in a single location by introducing reagents, solvents, etc. into a pre-set reaction container. For this reason, with these devices, the system has little flexibility or extendibility, and since the location of the reaction is limited, it is difficult to conduct several reactions simultaneously or freely rearrange the reaction process.

Again, the automated synthesis devices in, (II) above can only perform a single reaction in a single reaction device, and thus have the drawback that only one reaction can be conducted at a time.

Since the synthesis experiment device in (III) above uses a robot, it has more extendibility than the devices in (I) or (II), but since the number of possible experiment unit operations is small, it is unable to perform complex synthesis experiments which combine a plurality of unit operations.

In each of the foregoing conventional automated devices, a machine performs operations formerly performed by humans. However, these conventional automated devices have several problems, such as inability to perform several experiments simultaneously, a limited number of reagents which can be supplied automatically, a narrow reaction temperature range, a limited number of possible experiment unit operations, difficulty of improvement or extension of the device, etc. Accordingly, these conventional automated devices cannot be said to have dramatically reduced the effort or improved the efficiency of chemical experiments.

Further, with organic synthesis reactions, there are many cases in which the reaction produces a solution phase made up of at least two incompatible solutions. In such a case, the desired compound must be separated out from the reaction container.

With this kind of solution phase made up of two incompatible solutions which have separated into layers, separation processing to separate out each solution is often carried out in extraction processing, in which a desired compound is separated out from a reaction liquid obtained by, for example, an organic synthesis reaction. A separation funnel is often used for this separation processing.

In separation processing using a separation funnel, the operator separates the two solutions by, first, visually checking the liquid level of the solution phase which has separated into layers and the interface between the two solution layers, and then, in accordance with the liquid level and interface, extracting from the separation funnel one of the solutions of the solution phase, after which, as necessary, the other solution remaining in the separation funnel may be extracted into another container.

However, in using a separation funnel to separate out each solution from this kind of solution phase made up of two incompatible solutions which have separated into layers, the operator must check the positions of the liquid level of the solution phase and the interface between the two solutions, as well as perform the operations for separating out each solution.

Accordingly, in conventional separation processing using a separation funnel, since the separation processing itself is carried out by the operator, the operator must be used to operating with a separation funnel in order to perform the separation processing correctly. In other words, if the operator is not used to operating with a separation funnel, when the difference in color of the two solutions in the solution phase is subtle, it is difficult to correctly distinguish the interface, and the operator may not be able to correctly separate out the solutions of the solution phase.

Since the operations of the above-mentioned separation funnel are manual, it has been difficult to use in conventional devices which perform organic synthesis reactions automatically, and this has made automation of organic synthesis reactions difficult.

In conventional chemical experiments, when allowing two or more reagents to react in a reflux, reaction containers like that shown in FIG. 39 have been used (see Experimental Chemistry Lectures 2: Basic Operations II, 4th Ed., Maruzen Co., Ltd.).

The reaction container shown in FIG. 39 is made up of a flask 511 which contains a reagent C, a drip funnel 512 which contains a reagent D, a condenser 513, and a stirrer 514.

A reaction between the reagents C and D is conducted by dripping the reagent D from the drip funnel 512 into the flask 511 which contains the reagent C. This kind of reaction is often conducted with the application of heat, and reaction raw materials, reaction products, and reaction solvent vaporized by heating are cooled by the condenser 513, and are thus liquefied and returned to the flask 511. Further, in order to stabilize the reaction, stirring is usually performed using the stirrer 514.

In addition, this kind of reaction is usually performed with the reaction system sealed under open pressure by means of a filling tube filled with drying agent, etc. and attached to the top of the condenser 513.

In this way, in conventional reaction containers, the drip funnel 512, which is a reagent introducing member, the condenser 513, which is a cooling member, and the sealing member (not shown) were provided separately from the flask 511.

However, since the reagent introducing member, cooling member, and sealing member are provided separately, disadvantages of this kind of conventional reaction container are that the size of the container as a whole in increased, and that assembly of the container is troublesome.

Because of these problems, it has been difficult to use the above-mentioned conventional reaction container in conventional devices which perform organic synthesis reactions automatically, and this has made automation of organic synthesis reactions difficult.

DISCLOSURE OF THE INVENTION

The object of the present invention is to provide a synthesis experiment automation system which is capable of simultaneously performing a plurality of different experiments as complex as those usually performed by researchers, which has a large number of possible experiment operations, and which can be easily improved and/or extended.

Another object of the present invention is to provide a separation processing device which automatically detects a liquid level position and an interface position in a solution phase made up of two incompatible solutions which have separated into layers, and which automatically performs solution extraction operations based on the detected liquid level and interface positions.

A further object of the present invention is to provide a reaction container in which a reagent introducing section, a cooling section, and a sealing section are combined together, and which is compact and easy to assemble.

In order to attain the foregoing objects, the inventors, etc. of the present invention invented a synthesis experiment automation system, a separation processing device, and a reaction container, which are, collectively, capable of simultaneously performing a plurality of different experiments as complex as those usually performed by researchers, and which dramatically reduce the effort and improve the efficiency of chemical experiments.

Accordingly, in order to attain the foregoing objects, a synthesis experiment automation system according to the present invention is made up of:

(1) a reaction system which includes (a) a reaction container rack for storing a plurality of reaction containers, (b) a dispensing device for introducing reagents and solvents into the reaction containers, and (c) a reaction device having a plurality of reaction sections capable of holding a plurality of reaction containers into which reagents and solvents have been introduced, and which is capable of setting different experiment conditions for different reaction sections;

(2) a robot which removes reaction containers from the reaction container rack, transports the reaction containers to a dispensing position of the dispensing device, and transports reaction containers into which reagents and solvents have been introduced to a predetermined position in a reaction section of the reaction device; and (3) a computer which controls the actions of the robot in transporting and placing the reaction containers and the operations of the devices in the reaction system, separately for each set of experiment conditions.

With the foregoing structure, since the computer controls the operations of the devices in the reaction system separately for each set of synthesis reaction experiment conditions, the reaction sections within the reaction device can be operated under different experiment conditions. For example, if each reaction section in the reaction device is provided with temperature regulating means which can be set to different temperatures, and if temperature regulating operations of these temperature regulating means are controlled by the computer, a plurality of synthesis reactions can be simultaneously carried out under different temperature conditions.

Further, since each reaction section is capable of holding a plurality of reaction containers, synthesis reactions can be carried out under an even greater number of different experiment conditions.

Again, since the actions of the robot in transporting and placing the reaction containers are also controlled by the computer, the robot transports the reaction containers within the reaction system in accordance with the experiment conditions of each synthesis reaction. For this reason, the synthesis experiment automated system can easily be extended by simply placing additional reaction system devices within the robot's range of action.

In addition, since the actions of the robot in transporting and placing the reaction containers and the actions of the reaction system devices are controlled for the experiment conditions of each synthesis reaction, they can be flexibly tailored to various synthesis reactions, and the reaction process can be freely rearranged. This also improves the flexibility of the system as a whole.

In order to attain the foregoing objects, a separation processing device according to the present invention includes a reading means which reads an image of a solution phase made up of two incompatible solutions which have separated into upper and lower layers, a position detecting means which detects, from the image read by the reading means, the positions of the liquid level of the solution phase and the interface between the upper- and lower-layer solutions, and a solution extracting means which calculates the quantities of the upper- and lower-layer solutions on the basis of the results detected by the position detecting means, and extracts one or both of the upper- and lower-layer solutions of the solution phase.

With the foregoing structure, the position detecting means detects the positions of the liquid level and the interface from the image of the solution phase made up of two incompatible solutions which have separated into layers. Accordingly, operations for detecting the positions of the liquid level and the interface can be carried out automatically.

Further, the solution extracting means calculates the quantities of the upper- and lower-layer solutions on the basis of the results detected by the position detecting means, i.e., on the basis of the positions of the liquid level and interface detected by the position detecting means, and then extracts one or both of the upper- and lower-layer solutions. Accordingly, extraction of the solutions can also be automated.

Since the positions of the liquid level and the interface can be automatically detected by the position detecting means from the image of the solution phase read by the reading means, and each solution of the solution phase can be automatically extracted based on the results detected by the position detecting means, this separation processing device is suitable for use in a device for automatically performing organic synthesis reactions. This makes it easy to fully automate a device for automatically performing organic synthesis reactions.

In order to attain the foregoing objects, a reaction container according to the present invention is made up of:

(1) a container section, into which a first reagent is placed in advance; and
(2) an introducing tube which introduces a second reagent into the container section, and which includes:
 (a) a cooling section having an inner tube, through which the second reagent is introduced, and an outer tube surrounding the outer wall of the inner tube, which cools a vaporized component passing through the inner tube by means of a cooling medium passed through the outer tube;
 (b) a reagent introducing section which introduces the second reagent through an upper opening of the inner tube, and thence into the container section through a lower opening of the inner tube; and
 (c) a sealing section which introduces a gas through a gas flow intake branching from the outer tube.

With the foregoing structure, in order to conduct a reaction between the first and second reagents, the first reagent is placed in the container section in advance. Next, the second reagent is introduced into the container section through the introducing tube. At this time, the second reagent passes through the inner tube of the introducing tube. A vaporized component produced in the container section during reaction attempts to escape through the inner tube of the introducing tube, but is cooled by the cooling medium (water, for example) passing between the inner tube and the wall of the outer tube, and is thus liquefied and returned to the container section. Further, in order to seal the container interior by isolating it from the atmosphere, an inert gas (nitrogen, for example) is introduced through a gas flow intake provided in the wall of the upper part of the introducing tube. This gas flows into and fills the upper part of the inner tube, and is released from the upper opening of the inner tube.

Incidentally, the first and second reagents referred to above are not necessarily single compounds, and in some cases may be mixtures of two or more compounds. Again, the first and second reagents may each be mixed with reaction solvents, or a reaction solvent may be placed in the container section in advance.

By means of the reaction container outlined above, the reagent introducing section, cooling section, and sealing section, which conventionally were provided separately on the container section, can be combined into a single member, and thus a reaction container can be obtained which is more compact, and which is easily assembled.

Accordingly, since assembly is easy, a reaction container with the foregoing structure is suited for use in an automated device.

Additional objects, features, and strengths of the present invention will be made clear by the description below. Further, the advantages of the present invention will be evident from the following explanation in reference to the drawings.

BRIEF DESCRIPTION OF THE DRAWINGS

FIG. 2(*a*) is a plan view of a reaction container rack provided in the synthesis experiment automation system shown in FIG. 1.

FIG. 2(*b*) is a front view of a reaction container rack provided in the synthesis experiment automation system shown in FIG. 1.

FIG. 2(*c*) is a side view of a reaction container rack provided in the synthesis experiment automation system shown in FIG. 1.

FIG. 15(*b*) is a side view showing a robot provided in the synthesis experiment automation system shown in FIG. 1.

FIG. 16(*b*) is an explanatory drawing showing a grasping section of the robot arm shown in FIG. 16(*a*).

FIG. 17 is a control block diagram of the synthesis experiment automation system shown in FIG. 1.

FIG. 19 is an explanatory drawing showing an execution file preparation section in an input section of the computer shown in FIG. 18.

FIG. 23 is an explanatory drawing showing one example of an execution file preparation screen.

FIG. 38($b$) is a side view of a lid of a container section of the reaction container shown in FIG. 36.

BEST MODE FOR CARRYING OUT THE INVENTION

The following embodiment will explain the present invention in further detail, but the present invention is not limited in any way thereby.
EMBODIMENT The following will explain an embodiment of the present invention.

Figure 1:
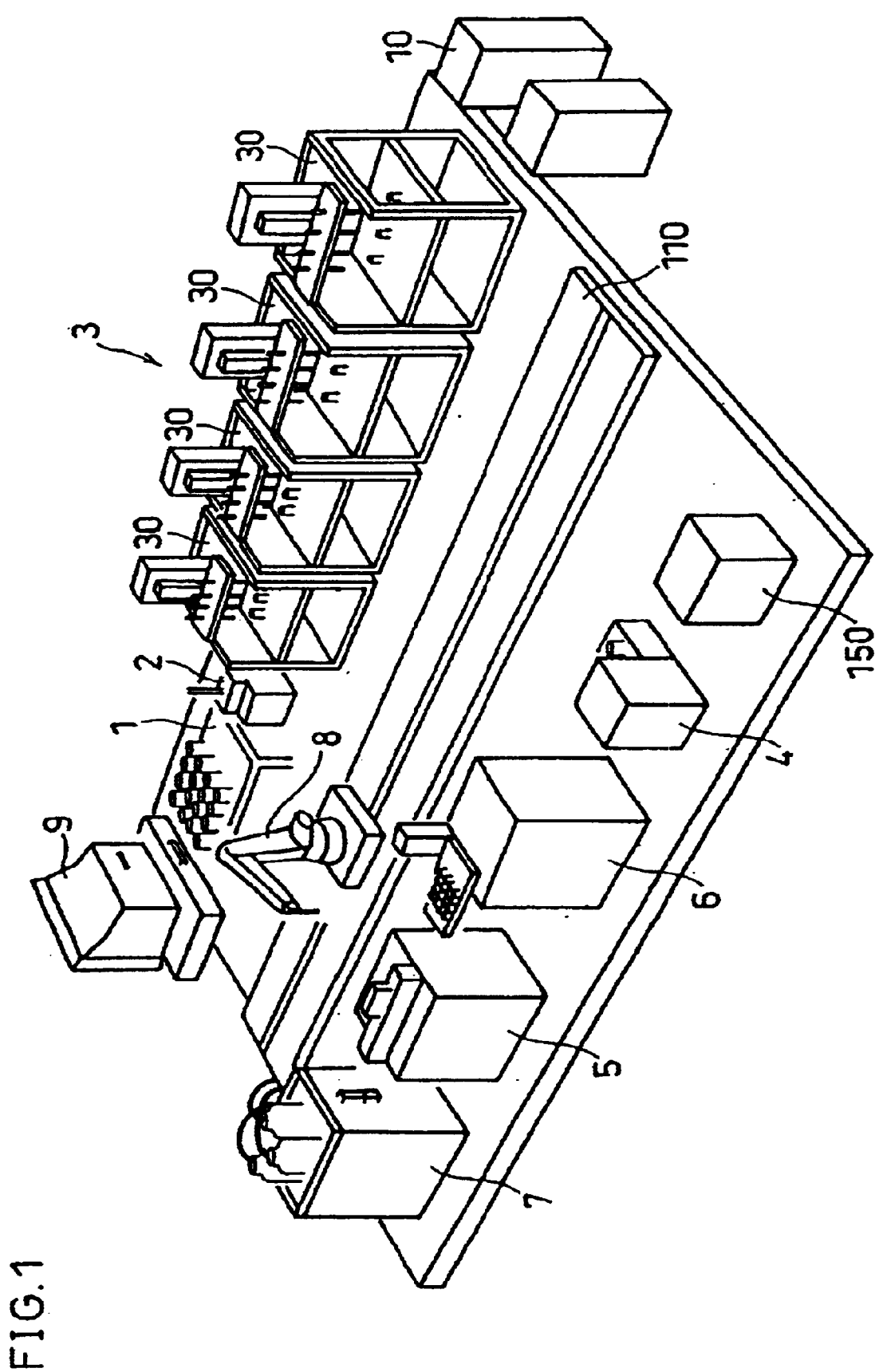
FIG. 1 is a schematic structural drawing of a synthesis experiment automation system according to an embodiment of the present invention.

As shown in FIG. 1, a synthesis experiment automation system according to the present embodiment includes a reaction system made up of a reaction container rack 1, a dispensing and separation device 2, a reaction device 3, a shaking device 4, a pre-analysis processing device 5, a gas chromatograph 6, and a liquid chromatograph 7; a robot 8; a computer 9; and a robot traveling rail 110.

In this synthesis experiment automation system, the robot 8, traveling along the robot traveling rail 110, transports containers to and places them at predetermined positions of the various devices, and the computer 9 controls the robot 8 and the various other devices. Thus, this is an experiment system which can perform desired synthesis experiments automatically. Accordingly, when the system is in operation, the containers transported among the various devices are transported by the robot 8. Since the robot 8 performs the actions of transporting and placing the reaction containers, the following explanations of the various devices omit explanation of the robot 8. The actions of the robot 8 will be discussed in detail later.

FIG. 1 shows the present synthesis experiment automation system only schematically, and the details of each device will be discussed later. Further, in the present embodiment, for ease of explanation, the synthesis experiment automation system will be divided into hardware and software, which will be explained separately. In other words, the following will first explain the various devices of the synthesis experiment automation system, and then explain how these various devices are controlled.

First, to begin explanation of the hardware, the reaction container rack 1 will be explained.

As shown in FIGS. 2($a$), 2($b$), and 2($c$), the reaction container rack 1 is made up of four storage sections: first, second, and third storage sections 11, 12, and 13, respectively, which store synthesis reaction containers 15 (reaction containers), and a fourth storage section 14, which stores a plurality of blind plugs 16 for the synthesis reaction containers 15.

Each of the first, second, and third storage sections 11, 12, and 13 is structured so as to store 4×4=16 synthesis reaction containers 15. Here, containers of 100 ml capacity are used as the synthesis reaction containers 15.

The fourth storage section 14 is structured so as to store 4×4=16 blind plugs 16. In the present embodiment, the fourth storage section 14 stores the blind plugs 16. However, there is no need to be limited to this, and other parts may be stored here. Accordingly, the fourth storage section 14 is a storage section which may be provided as needed.

In the first storage section 11 are stored empty synthesis reaction containers 15 before the introduction of reagents or solvents, and in the second storage section 12 are stored synthesis reaction containers 15 filled with reacted solutions after completion of the reaction.

The third storage section 13 is a place for temporary storage of synthesis reaction containers 15 or other containers filled with solutions in the process of reaction. Here, operations such as the introduction of reaction suspension agent for stopping a synthesis reaction are performed. Accordingly, the third storage section 13, like the fourth storage section 14, is a storage section which may be provided as needed.

Since the second storage section 12 stores synthesis reaction containers 15 after reaction, the second storage section 12 may, depending on the reaction temperatures of the synthesis reaction containers 15, be subjected to very high temperatures. For this reason, the part of the second storage section 12 which supports the synthesis reaction containers 15 is made of heat-resistant ethylene tetrafluoride resin. For the same reason, the blind plugs 16 are also made of ethylene tetrafluoride resin.

In the present embodiment, each of the storage sections is structured so as to store 16 synthesis reaction containers 15 or blind plugs 16, but there is no need to be limited to this number. Again, the order in which the storage sections are arranged is not limited to any particular order. Further, the reaction container rack 1 includes three sections for storing synthesis reaction containers 15, but there is no need to be limited to this number. In addition, the part of the second storage section 12 which supports the synthesis reaction containers 15, and the blind plugs 16, are made of ethylene tetrafluoride, but there is no need to be limited to this material; it is sufficient if these members are made of a material which is heat- and chemical-resistant.

Next, the dispensing and separation device 2 will be explained.

The dispensing and separation device has three functions: (1) a dispensing function of separately introducing solvents and reagents into the synthesis reaction containers 15; (2) a separation function of extracting an indicated solution from a reacted liquid which has separated into layers; and (3) a discharge function of discharging reacted liquids after reaction.

Figure 3:
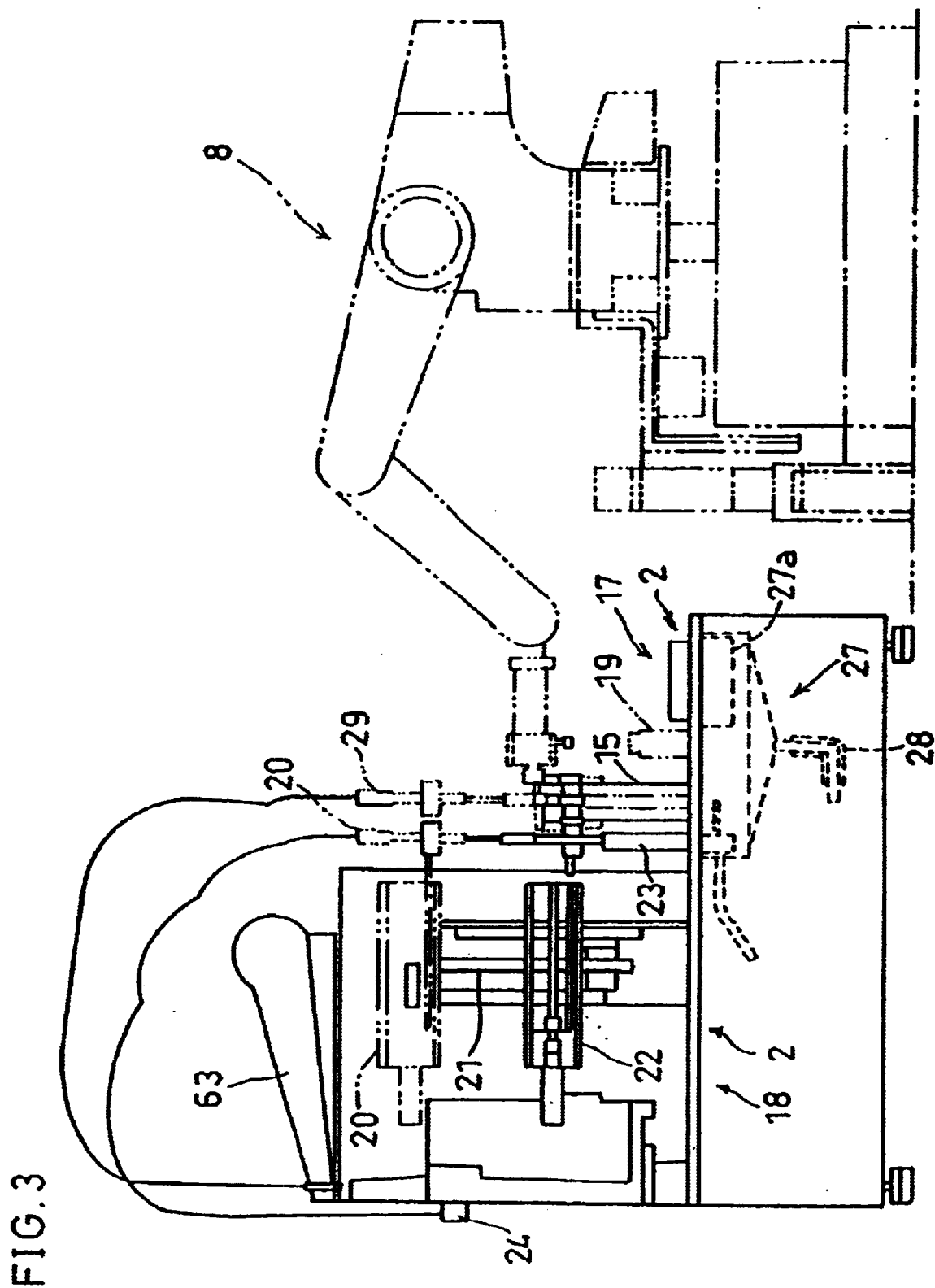
FIG. 3 is a schematic structural drawing of a dispensing and separation device provided in the synthesis experiment automation system shown in FIG. 1.

Accordingly, as shown in FIG. 3, the dispensing and separation device 2 is made up of a container placement section 17, where synthesis reaction containers 15 transported from the reaction container rack 1 are placed, and an introduction and extraction structure 18, which introduces reagents and solvents into a synthesis reaction container 15 placed on the container placement section 17, or extracts from a synthesis reaction container 15 placed on the container placement section 17 one of the solutions which have separated into layers after reaction.

The container placement section 17 is provided so that synthesis reaction containers 15 both prior to and after reaction may be placed thereon, and, further, so that solution storage containers 19, which store solutions extracted from synthesis reaction containers 15 after reaction, may be placed thereon.

The introduction and extraction structure 18 is made up of a needle bundle 20 including an introduction and extraction needle, which introduces reagents and solvents into and extracts solutions from synthesis reaction containers 15, and a nitrogen needle, which introduces nitrogen; a conductivity sensor 29, which is a detector which detects the electrical conductivity of solutions separated into layers after reaction; and a vertical shift axle 21 and a horizontal shift axle 22, which drive the needle bundle 20 and the conductivity sensor 29 vertically and horizontally, respectively.

In other words, in the introduction and extraction structure 18, the needle bundle 20 and the conductivity sensor 29 are moved from withdrawn positions to a dispensing/separation position, and vice versa, by the vertical shift axle 21 and the horizontal shift axle 22. In its withdrawn position, the introduction and extraction needle of the needle bundle 20 is inside a rinse port 23. The rinse port 23 is able to perform discharge processing of solutions, since it is connected to a discharge section 27 (to be discussed below), which discharges solutions to the exterior of the device.

In other words, after a synthesis reaction container 15 is placed in a predetermined position on the container placement section 17, the introduction and extraction structure 18, by means of the vertical shift axle 21, moves the needle bundle 20 upwards from its withdrawn position inside the rinse port 23; then, by means of the horizontal shift axle 22, moves the needle bundle 20 horizontally until its lower end is directly above a mouth of the synthesis reaction container 15 placed on the container placement section 17; next, using the vertical shift axle 21, it moves the needle bundle 20 downward so as to insert it into the synthesis reaction container 15; and then performs dispensing or separation (extraction) operations.

Figure 4:
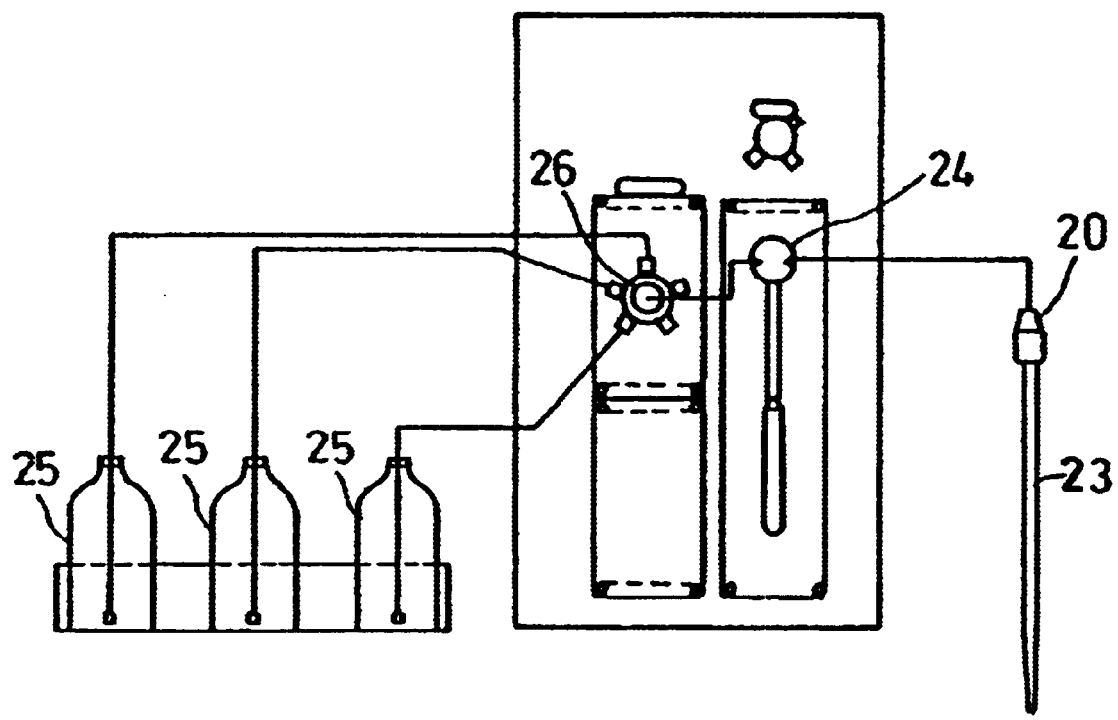
FIG. 4 is an explanatory drawing showing connections between solvent bottles and a dispensing needle of the dispensing and separation device shown in FIG. 3.

As shown in FIG. 4, the needle bundle 20 is connected, via a digital syringe pump 24, to a plurality of solvent bottles 25, which contain various solvents. Between the solvent bottles 25 and the digital syringe pump 24 is provided a switching valve 26, by control of which the digital syringe pump 24 is able to transport to the needle bundle 20 a solvent from a desired solvent bottle 25.

By being lowered into a solution in a synthesis reaction container 15, the conductivity sensor 29 detects data regarding conductivity domains (domains in a solution having different conductivities) and the liquid level of the solution where the conductivity domain changes. In other words, using the conductivity sensor 29, the interface of a reaction liquid which has separated into layers is detected. As with the actions of the needle bundle 20 described above, the actions of the conductivity sensor 29 are driven and controlled by means of the vertical shift axle 21 and the horizontal shift axle 22.

Conventional methods of performing separation automatically include optical methods using differences in refractive index, etc. There are also methods which use differences in electrical properties such as dielectric constant, etc. However, in applying these methods to the present invention, it was necessary, with each method, to scan the interface using a sensor, etc., with the drawback that the device for performing this scanning was expensive.

However, if, as in the present invention, a method is used whereby the point at which conductivity changes is detected as the interface between solutions, a device can be provided which is smaller in scale and less expensive than conventional devices which scan the interface using a sensor.

The conductivity sensor 29 is connected to a conductivity meter 63 provided on top of the introduction and extraction structure 18. The conductivity meter 63 is connected to the computer 9 of the present synthesis experiment automation system, and data detected by the conductivity sensor 29 are sent one by one through the conductivity meter 63 to the computer 9, by means of a communications function. This communications function is realized by mutual connection of RS232C terminals (to be discussed below) or terminals governed by RS232C specifications. Accordingly, data from the computer 9 can also be sent to the dispensing and separation device 2.

Next, based on the detected data, the computer 9 calculates the conductivity and liquid level of each solution in the synthesis reaction container 15, and sends the calculated results to the dispensing and separation device 2. In the dispensing and separation device 2, based on these calculated results, the introduction and extraction structure 18 moves the needle bundle 20 to a predetermined position in the solution in the synthesis reaction container 15, and then the digital syringe pump 24 extracts from the synthesis reaction container 15 a predetermined quantity of an indicated solution. At this time, the extracted solution is stored in the needle bundle 20, and, if the solution is needed, it is discharged into, for example, a sample bottle. If the solution is not needed, when the needle bundle 20 is withdrawn to the rinse port 23, the solution is discharged by the digital syringe pump 24 to the discharge section 27.

In this way, the dispensing and separation device 2 is provided so that, during separation operations, the conductivity sensor 29 detects the conductivity of the solutions in the synthesis reaction container 15, and then, based on the detected results, the needle bundle 20 extracts only a solution indicated in advance.

In the dispensing and separation device 2, when solvent is introduced into the synthesis reaction container 15 by the introduction and extraction needle of the needle bundle 20, the nitrogen needle usually introduces nitrogen into the synthesis reaction container 15 simultaneously with the introduction of the solvent, so as to create a nitrogen environment in the synthesis reaction container 15. Further, if necessary, the nitrogen may be introduced prior to introducing the solvent into the synthesis reaction container 15.

At the front of the container placement section 17 is provided the discharge section 27, for discharging reaction liquids after synthesis reaction and analysis. The discharge section 27 is provided with a discharge opening 27a, and with a discharge pipe 28, which discharges to the exterior of the device solutions discharged into the discharge opening 27a. Further, the rinse port 23, into which the needle bundle 20 is withdrawn, is connected to the discharge section 27, such that extracted solutions may be discharged through the rinse port 23.

As discussed above, the dispensing and separation device 2 has three functions. Of these, the second function (the separation function of extracting an indicated solution from a reacted liquid which has separated into layers) may be realized by a separate device. For example, the dispensing and separation device 2 explained above may be used for introducing reagents, and separation processing of reacted liquids may be performed by a separation processing device such as that shown in FIGS. 30 through 35. This separation processing device will be explained later.

Next, the reaction device 3 will be explained.

As shown in FIG. 1, the reaction device 3 has four temperature regulator units 30 (reaction sections), each of which can freely change its set reaction temperature. Since each of the four has the same structure, the following will only explain one temperature regulator unit 30. Incidentally, in the reaction device 3 according to the present embodiment, each of the temperature regulator units 30 has the same structure, but there is no need to be limited to this. A reaction device having temperature regulator units with different structures may also be used.

Figure 5:
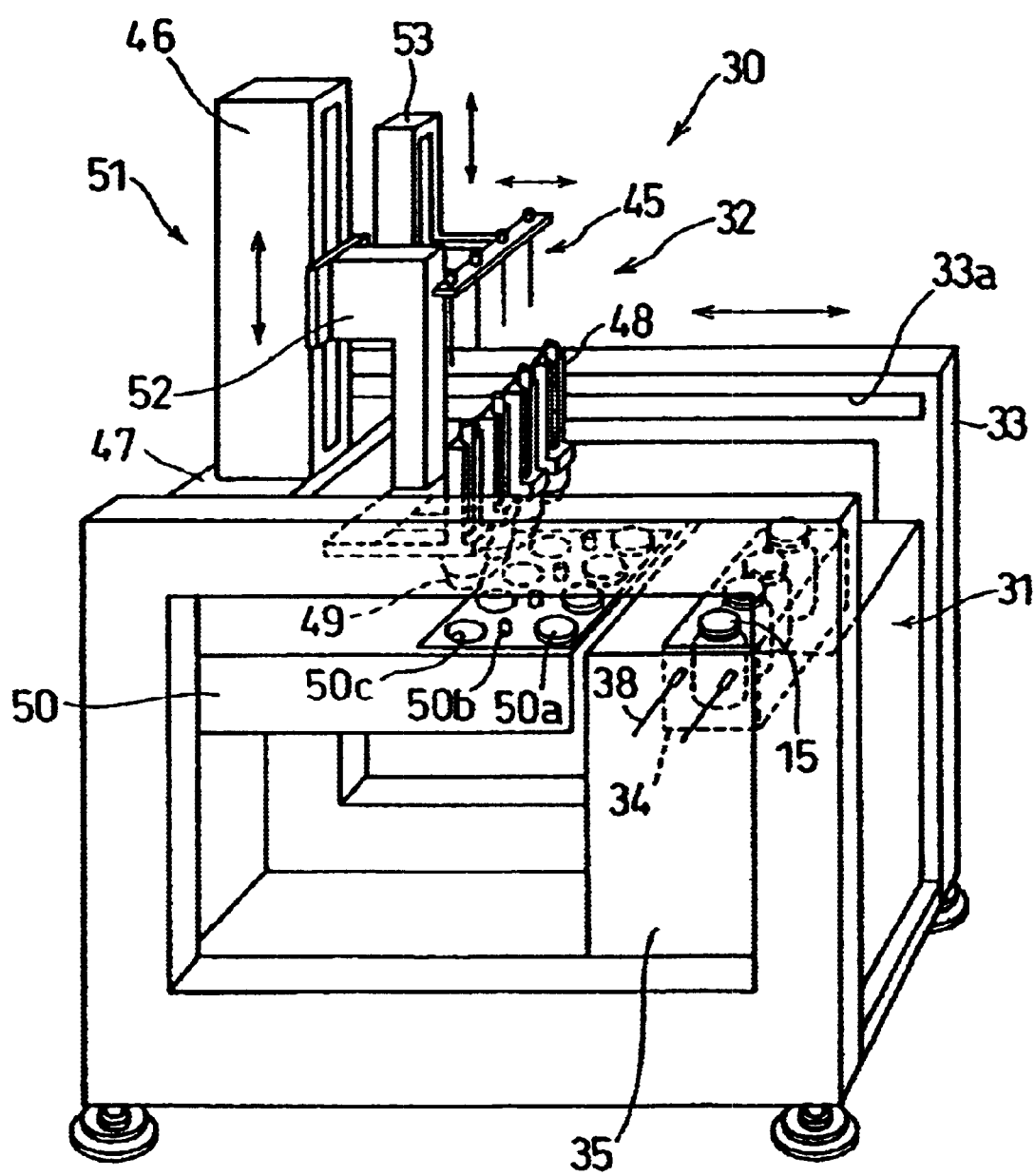
FIG. 5 is a schematic structural drawing of a reaction device provided in the synthesis experiment automation system shown in FIG. 1.

As shown in FIG. 5, the temperature regulator unit 30 is made up of a temperature control structure 31, which heats synthesis reaction containers 15 placed therein at a previously set temperature; a reagent introducing section 32, which introduces reagents into the synthesis reaction containers 15 placed in the temperature control structure 31; and a supporting body 33, which is provided so as to surround and support the temperature control structure 31 and the reagent introducing section 32. In other words, the temperature control structure 31 is supported by the lower part of the supporting body 33, and the reagent introducing section 32 is supported by the upper part of the supporting body 33 so as to be freely moveable horizontally.

The temperature control structure 31 is made up of a reaction vessel 34, which holds four synthesis reaction containers 15, and a stirring section 35, which stirs the solutions in the synthesis reaction containers 15 in the reaction vessel 34.

The reaction vessel 34 has a temperature regulating function, and is made of an aluminum block 36 (see FIG. 6) which is freely removable from the temperature control structure 31. The aluminum block 36 has four cylindrical openings 36a, which hold the synthesis reaction containers 15, and in the lower part of the aluminum block 36 is provided a heater 37 for heating the synthesis reaction containers 15.

Figure 7:
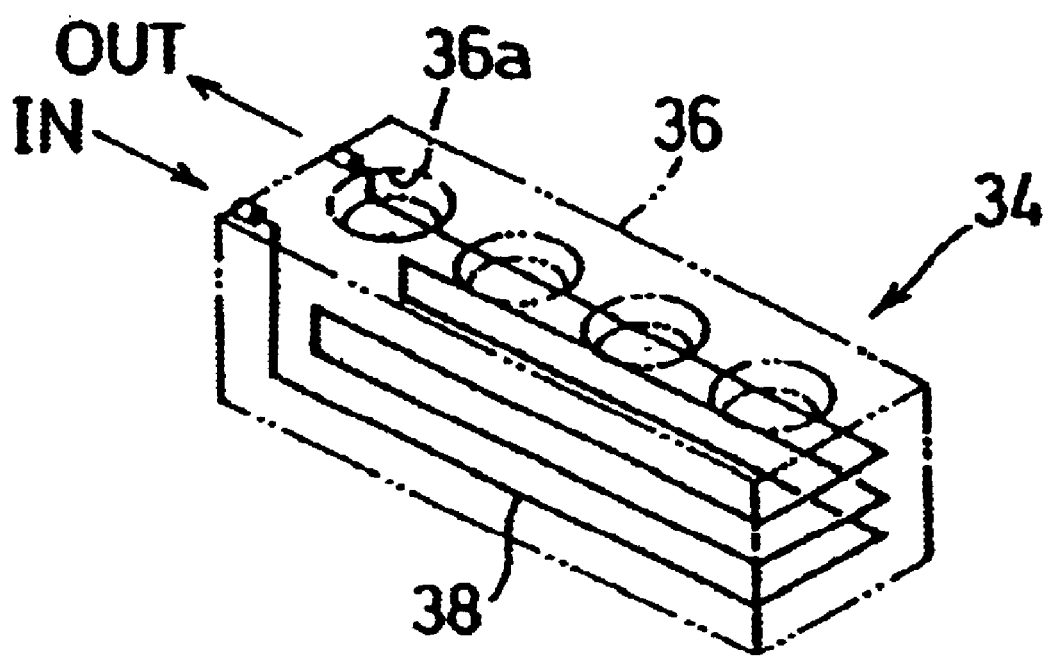
FIG. 7 is an explanatory drawing showing a cooling structure of the reaction vessel shown in FIG. 6.

Further, as shown in FIG. 7, the aluminum block 36 includes a cooling pipe 38, provided so as to wrap around the synthesis reaction containers 15, which prevents excessive heating thereof. The cooling pipe 38 is not provided solely to prevent excessive heating of the synthesis reaction containers 15, but is also provided (1) for cooling the reaction liquid to below room temperature (for low-temperature reactions); (2) for quick cooling of the thick aluminum block 36; and (3) for suppressing overshoot. The cooling pipe 38 is connected to a coolant circulation device 10 shown in FIG. 1.

The heater 37 is made of, for example, a cartridge-type heater, and heats the synthesis reaction containers 15 by transmitting heat to them through the aluminum part of the aluminum block 36. The cooling pipe 38 is made of fine tubing made of bronze tubing, and cooled water is circulated around the synthesis reaction containers 15 by introducing cooled water from the end of the cooling pipe 38 connected to the coolant circulation device 10, and discharging the cooled water from the other end thereof.

Further, a temperature sensor 39 is provided in the reaction vessel 34 below the position where the synthesis reaction containers 15 are placed. Based on a detection signal from the temperature sensor 39, a temperature controller 40 (shown in FIG. 8), provided below the reagent introducing section 32, performs temperature control of the heater 37.

However, the reaction liquid in the synthesis reaction containers 15 can easily be over-heated, even if the temperature controller 40 performs temperature control of the heater 37 based on the temperature of the reaction liquid in the synthesis reaction containers 15 as detected by the temperature sensor 39. Thus it is difficult to maintain the reaction liquid at a predetermined temperature.

For this reason, by providing the cooling pipe 38 around the synthesis reaction containers 15 as discussed above, the reaction liquid in the synthesis reaction containers 15 can be prevented from excessive heating. In this case, the flow of water through the cooling pipe 38 is controlled by controlling the coolant circulation system 10 to which the cooling pipe 38 is connected, and thus the synthesis reaction containers 15 can be maintained at a predetermined temperature by cooling as needed by the cooling pipe 38. Flow control in this case is performed on the basis of the detection signal of the temperature sensor 39.

Since a reaction vessel 34 with the foregoing structure is composed of the aluminum block 36, which is made of highly heat-conductive aluminum, it has the advantage of being able to precisely regulate the temperature of the reaction liquid in the synthesis reaction containers 15 placed in the reaction vessel 34. In addition, since aluminum is lighter than other metals, it also has the advantage of ease of handling.

Figure 6:
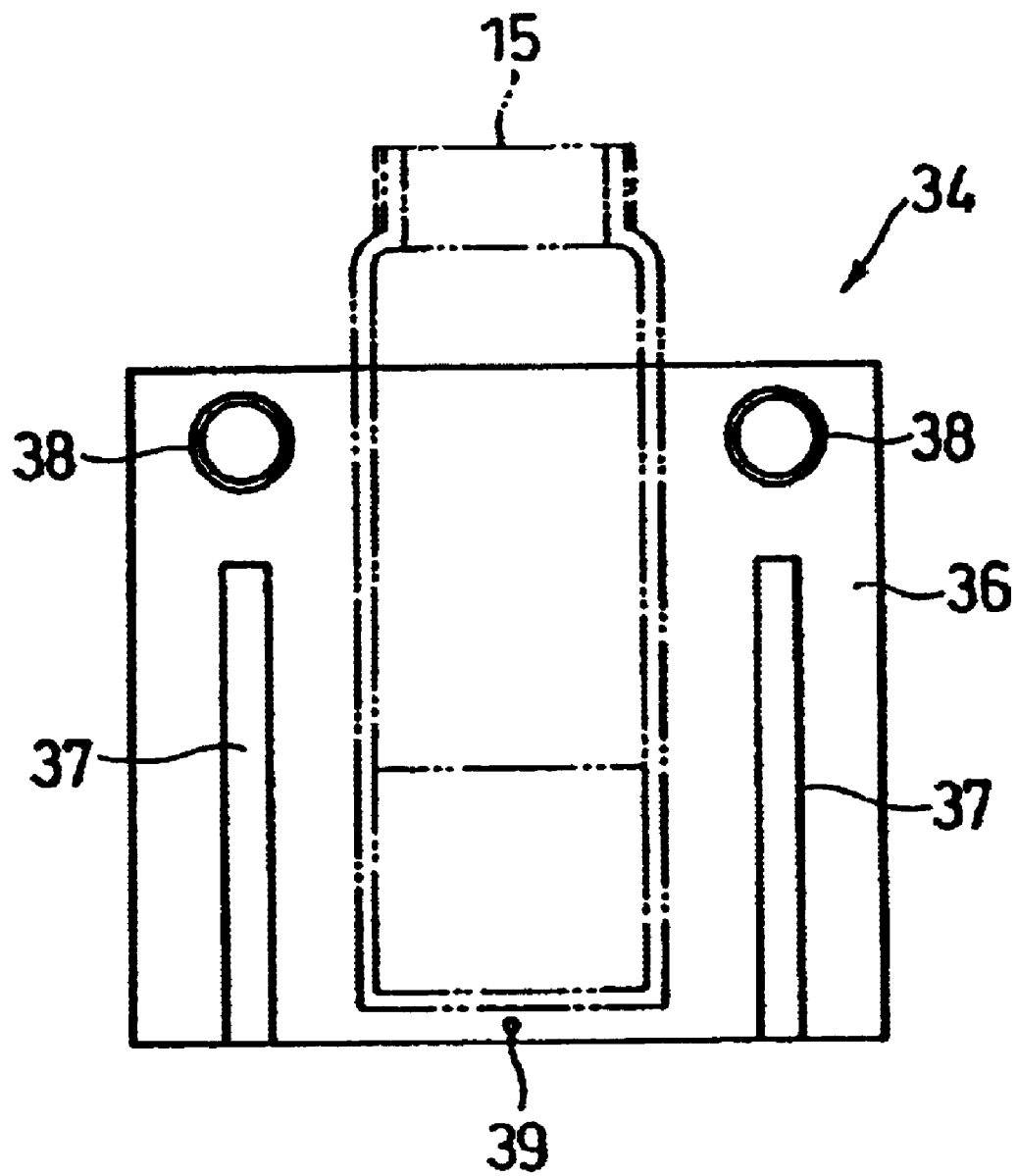
FIG. 6 is a schematic structural drawing of a reaction vessel of the reaction device shown in FIG. 5.

The aim of the heater 37 and the cooling pipe 38 is to maintain the solution in the synthesis reaction containers 15 at a set temperature, and thus there is no need to be limited to the structures shown in FIGS. 6 and 7, as long as the structure used is capable of maintaining the solution in the synthesis reaction containers 15 at a predetermined temperature.

Figure 8:
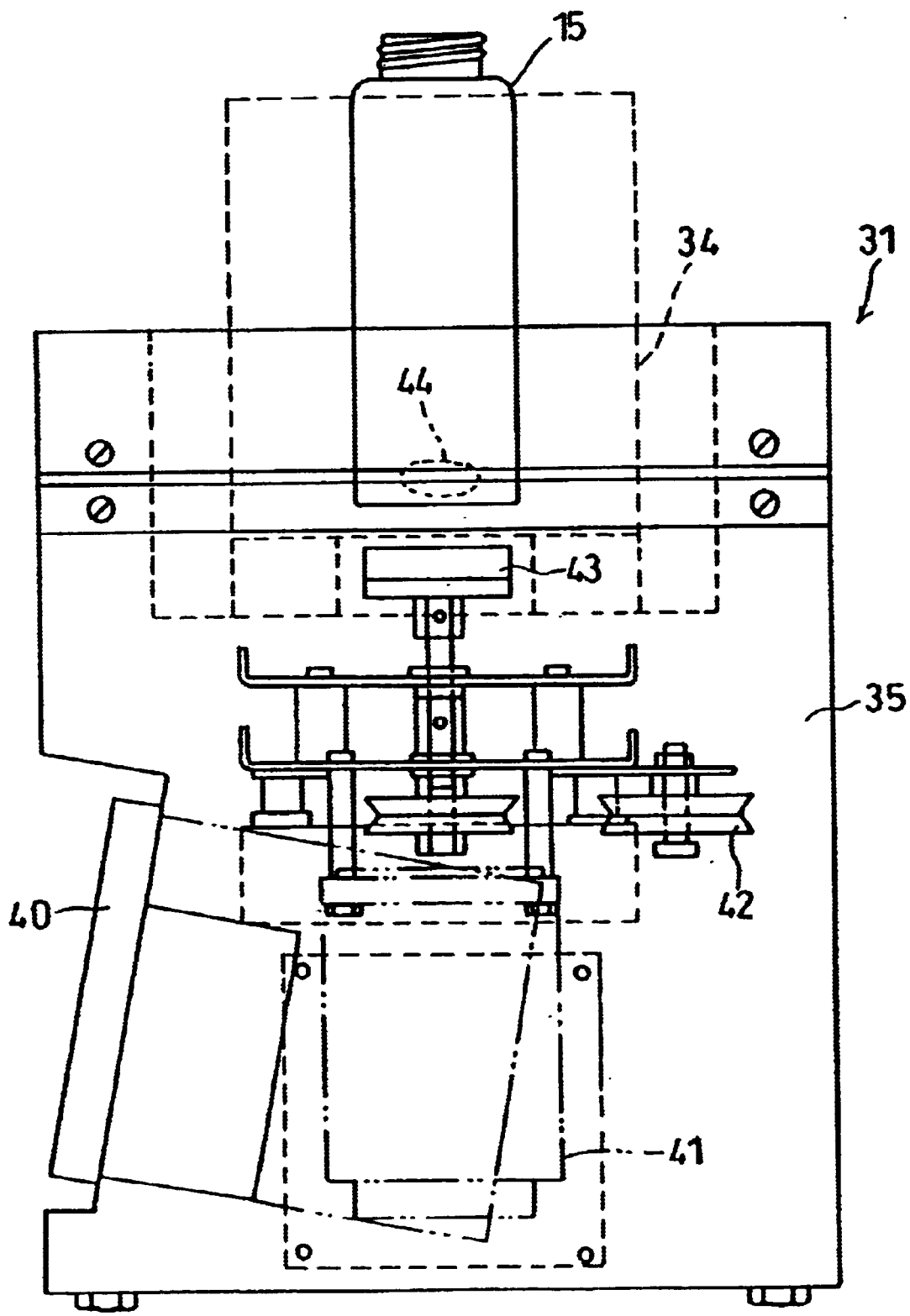
FIG. 8 is a schematic structural drawing of a temperature control structure provided in the reaction device shown in FIG. 5.

As mentioned above, the temperature control structure 31 has, in addition to the reaction vessel 34, a stirring section 35, shown in FIG. 8, for stirring the reaction solution in the synthesis reaction containers 15.

The stirring section 35 is made up of an AC motor 41, provided in the lower part of the temperature control structure 31; a pulley 42, provided above the AC motor 41 and connected to its driving shaft; and a magnet section, provided opposite a surface on which the synthesis reaction containers 15 are placed, which is rotated by belt transmission of the driving force of the AC motor 41 through the pulley 42.

The magnet section 43 includes a plurality of magnets, each rotated by the driving force of the AC motor 41, which cause stirrers 44 previously placed inside the synthesis reaction containers 15 to rotate, thus stirring the reaction solution in each synthesis reaction container 15.

The stirrers 44 are placed inside the synthesis reaction containers 15 at the time of introduction of reagents and solvents in advance by the dispensing and separation device 2.

The reagent introducing section 32 introduces reagents, as reaction materials, into synthesis reaction containers 15 placed in the temperature control structure 31 described above.

As shown in FIG. 5, the reagent introducing section 32 is made up of four reagent introducing needles 45 for introducing reagents into the synthesis reaction containers 15; four cooling tubes 48 for cooling the synthesis reaction containers 15; a lid washing and storage section 50 for washing and storing lids for the synthesis reaction containers 15 (hereinafter referred to as "seal caps 49"); and a driving section 51, which includes a vertical driving section 46 and a horizontal driving section 47.

In the lid washing and storage section 50, four each of the following members are provided, in four locations corresponding to the four reagent introducing needles 45: storage sections 50a, for storing the seal caps 49 for sealing the synthesis reaction containers 15 during reaction; needle rinses 50b, to which reagent introducing needles 45 are withdrawn; and washing sections 50c, for washing the seal caps 49.

By means of driving means (not shown), the horizontal driving section 47 moves horizontally along guide channels 33a provided in the supporting body 33 running toward the temperature control structure 31 side thereof.

The vertical driving section 46 is provided on the horizontal driving section 47, so as to move horizontally in accompaniment with the horizontal movement of the horizontal driving section 47.

The vertical driving section 46 is provided with a first supporting member 52, which supports the cooling tubes 48 and moves freely in a vertical direction. Further, the first supporting member 52 is provided with a second supporting member 53, which supports the reagent introducing needles 45.

The second supporting member 53 moves along with the first supporting member 52, and supports the reagent introducing needles 45 such that they are freely moveable horizontally and vertically. In other words, the second supporting member 53 moves the reagent introducing needles 45 so as to insert them into the cooling tubes 48, and also moves them to the needle rinses 50b of the lid washing and storage section 50.

By means of the vertical movement of the vertical driving section 46 and the horizontal movement of the horizontal driving section 47, the first supporting member 52 moves the cooling tubes 48 to predetermined positions, i.e., the washing sections 50c and storage sections 50a of the lid washing and storage section 50, and the set position of the synthesis reaction containers 15 in the temperature control structure 31.

Driving control of the vertical driving section 46 and the horizontal driving section 47 of the driving section 51 is performed by the computer 9, to be discussed below.

Next, a cooling tube 48 and a seal cap 49 will be explained.

Figure 9:
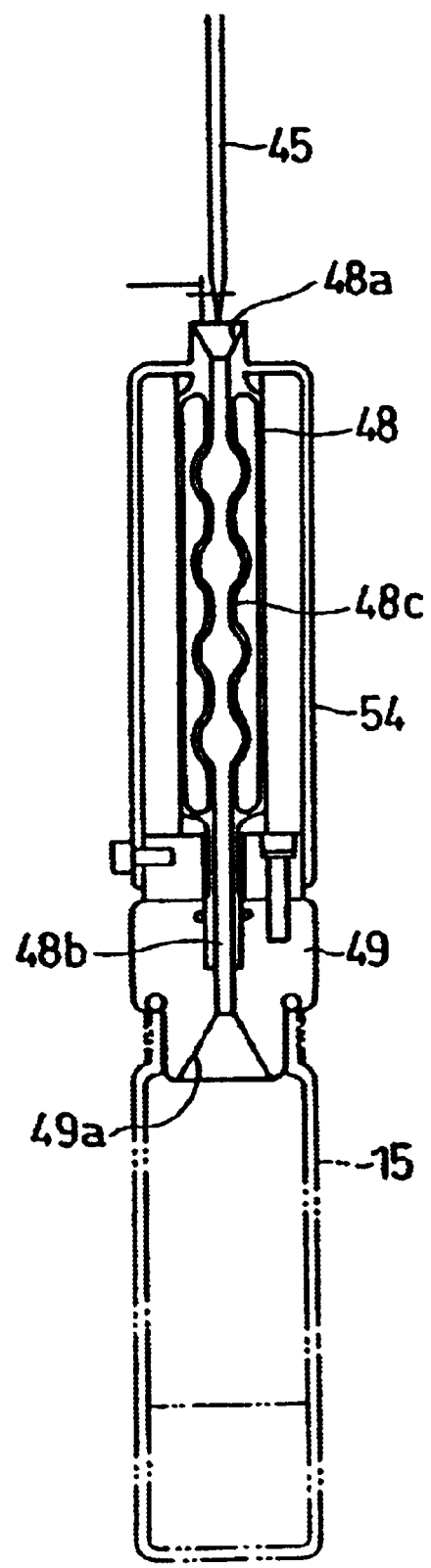
FIG. 9 is a schematic structural drawing of a cooling tube provided in the reaction device shown in FIG. 5.

As shown in FIG. 9, the cooling tube 48 is a reflex condenser made of glass, and its exterior is surrounded by a cylindrical member 54. When supporting the cooling tube 48, the cylindrical member 54 is held, thus protecting the cooling tube 48 from breakage.

In the cooling tube 48, a first opening section 48a is provided so that the end of a reagent introducing needle 45 can be inserted therein, and a second opening section 48b is provided so as to fit into a through hole 49a of a seal cap 49. The first opening section 48a is provided with a wide mouth, so that the reagent introducing needle 45 can be easily inserted therein. A cooling section 48c located substantially at the center of the cooling tube 48 is provided such that its surface area is greater than that of a typical cylinder, and acts to cool high-temperature gas flowing from a synthesis reaction container 15.

The seal cap 49 is chiefly composed of, for example, a PTFE (poly-tetraf luoro-ethylene) material, is sealed with a silicon material, and serves as a lid for the top of a synthesis reaction container 15. The through hole 49a of the seal cap 49 is provided so that it has a wide mouth on the side toward the synthesis reaction container 15.

The seal cap 49 is attached to the cooling tube 48 by tightening of screws, etc., and generally moves integrally with the cooling tube 48. Consequently, when a seal cap 49 is placed on a synthesis reaction container 15, a cooling tube 48 is also provided on the top of the seal cap 49.

After the reagent introducing needle 45 completes introduction of the reagents, and the synthesis reaction begins in the synthesis reaction container 15, the reagent introducing needle 45 performs a nitrogen gas purge from the first opening section 48a of the cooling tube 48, thus preventing air from flowing into the synthesis reaction container 15, and preventing the production of water therein.

The following will explain a reagent dispensing structure which uses the reagent introducing needles 45.

Figure 10:
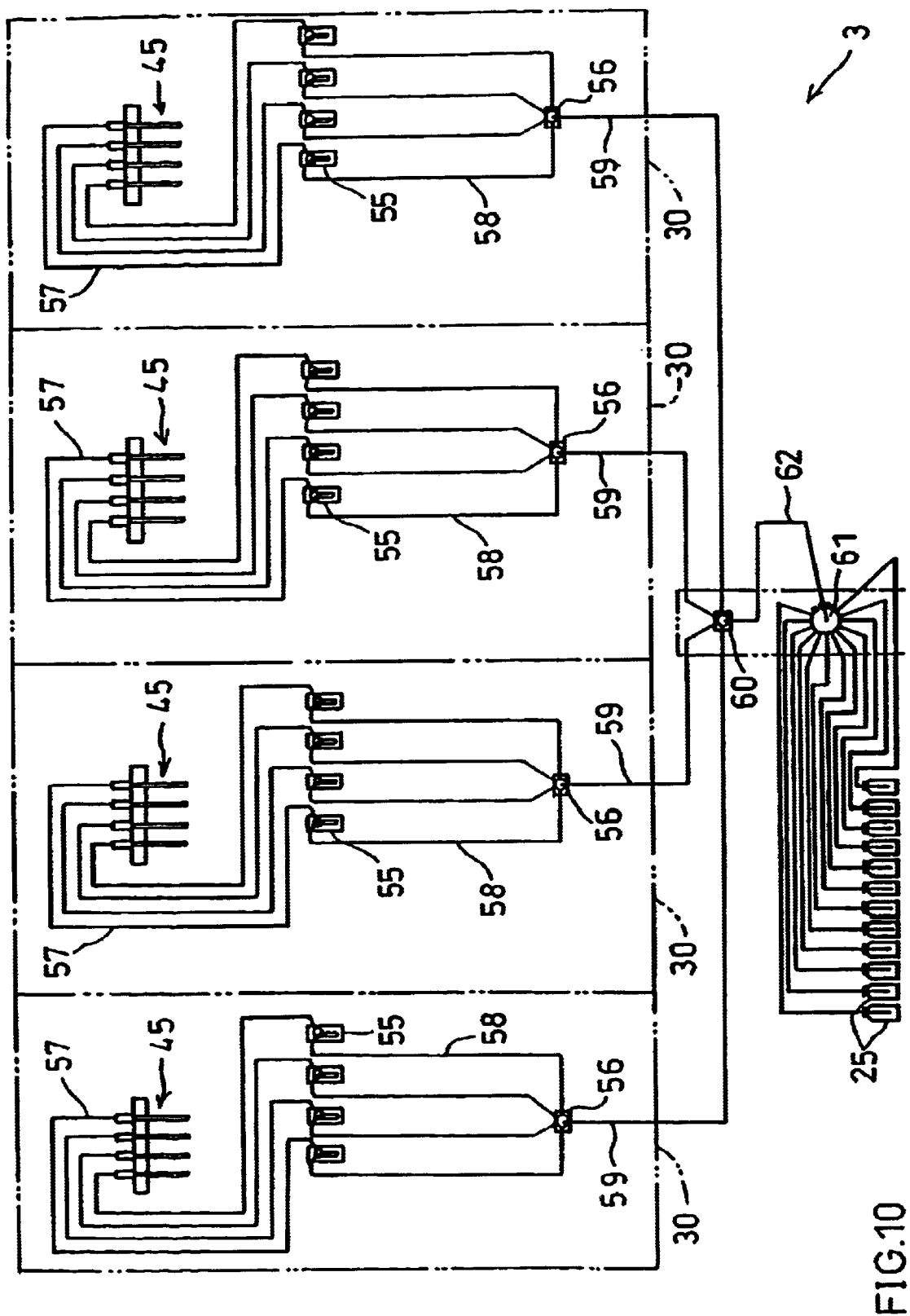
FIG. 10 is a schematic drawing showing a reagent and solvent supply system in the reaction device shown in FIG. 5.

As shown in FIG. 10, the reagent dispensing structure includes, for each of the four temperature regulator units 30 of the reaction device 3, digital syringe pumps 55 and a first switching valve 56, and each reagent introducing needle 45 is connected to the first switching valve 56 through one of the digital syringe pumps 55. In other words, each digital syringe pump 55 is connected to (a) one end of a first tube 57, the other end of which is connected to a reagent introducing needle 45, and to (b) one end of a second tube 58, the other end of which is connected to the first switching valve 56.

To the inflow side of each first switching valve 56 is connected a transport tube 59, which transports reagents from various solvent bottles 25, and to the outflow side of each first switching valve 56 are connected the four second tubes 58. By this means, a reagent is transported by the transport tube 59 to the first switching valve 56, which is selectively switched to transport the reagent through one of the first tubes 57 to one of the reagent introducing needles 45. At this time, in accompaniment with the switching operations of the first switching valve 56, the appropriate digital syringe pump 55 operates, thus transporting the reagent to the corresponding reagent introducing needle 45.

Further, the transport tube 59 for each temperature regulator unit 30 is connected to the outflow side of a second switching valve 60. To the inflow side of the second switching valve 60 is connected a connecting tube 62, the other end of which is connected to a third switching valve 61.

The third switching valve 61 is a sixteen-way switching valve with sixteen terminals on the inflow side and one terminal on the outflow side, and selectively switches among the various solvent bottles 25. In the present embodiment, twelve solvent bottles 25 are connected to terminals on the inflow side of the third switching valve 61. In this case, as shown in FIG. 10, four terminals on the inflow side have nothing connected to them, but if four solvent bottles 25 are connected to these four terminals, selection among a total of sixteen solvent bottles 25 may be performed.

Each of the solvent bottles 25 contains a different reagent, and the solvent bottle 25 containing a desired reagent may be selected by switching of the third switching valve 61. Further, if necessary, one or more of the solvent bottles 25 may contain a reaction suspension agent for stopping the synthesis reaction in a synthesis reaction container 15.

In the foregoing reagent dispensing structure, each of the switching valves is controlled by the computer 9 (to be discussed below). In other words, in the reagent dispensing structure, the computer 9 selects a solvent bottle 25 containing a desired reagent by switching control of the third switching valve 61. Then the computer 9 switches the second switching valve 60 so that the reagent from the solvent bottle 25 selected by the third switching valve 61 is transported to a desired temperature regulator unit 30. Next, the computer 9 switches the first switching valve 56 of the desired temperature regulator unit 30 so that the reagent transported via the second switching valve 60 and the transport tube 59 is transported to a desired reagent introducing needle 45. In this way, a reagent introducing needle 45 can introduce a desired reagent into a desired synthesis reaction container 15.

In the present embodiment, the reaction container used in the reaction device 3 is one made up of a synthesis reaction container 15 with its top covered, via a seal cap 49, by a cylindrical member 54 for reagent introducing and cooling. However, there is no need to be limited to this structure; the reaction container shown in FIGS. 36 through 38 may also be used. The details of this reaction container will be explained later.

The quantity of reagent introduced by each reagent introducing needle 45 is controlled by the corresponding digital syringe pump 55, and thus can be set separately for each reagent introducing needle 45. Driving of the digital syringe pumps 45 is controlled by the computer 9.

As discussed above, a reaction device 3 with the foregoing structure has four temperature regulator units 30, each of which can be set to a different reaction temperature, and each temperature regulator unit 30 can hold four synthesis reaction containers 15 having different synthesis conditions (other than temperature). Accordingly, a total of sixteen types of synthesis experiment may be carried out simultaneously. The foregoing reaction device 3 is capable of temperature control from −30° C. to 200° C.

Incidentally, in the present embodiment, as discussed above, four different synthesis reaction temperatures may be set, but there is no need to be limited to this. For example, the number of temperature regulator units 30 can be increased, thus increasing the number of synthesis temperatures which can be set. Again, the temperature regulator units 30 of the present embodiment hold four synthesis reaction containers 15 each, but there is no need to be limited to this. For example, the number of synthesis reaction containers 15 held by one temperature regulator unit 30 may be increased, giving consideration to the size of the temperature regulator unit 30, the size of the synthesis reaction container 15, etc. Accordingly, in the present embodiment, sixteen types of synthesis experiment may be performed simultaneously, but if the number of temperature regulator units 30 and the number of synthesis reaction containers 15 per temperature regulator unit 30 are increased, more than sixteen synthesis experiments can be performed simultaneously.

In the reaction device 3 with the foregoing structure, synthesis reaction containers 15 with completed synthesis reactions are temporarily stored in the second storage section 12 of the reaction container rack 1, and then the reaction solution is separated into layers in the shaking device 4.

Next, the shaking device 4 will be explained.

Figure 11:
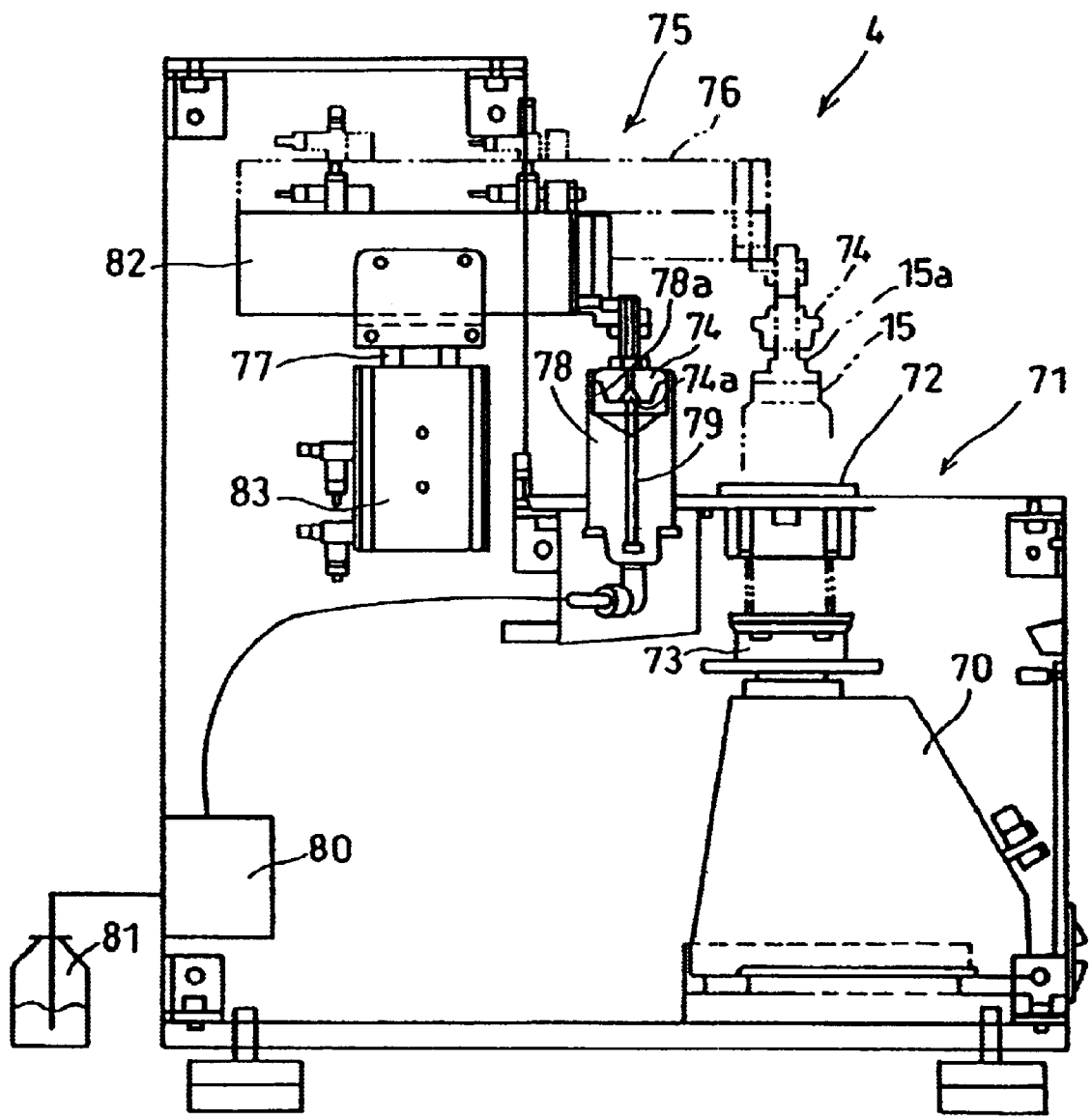
FIG. 11 is a schematic structural drawing of a shaking device provided in the synthesis experiment automation system shown in FIG. 1.

As shown in FIG. 11, the shaking device 4 is made up of a vortex mixer 70 as a container shaking section, which shakes a synthesis reaction container 15, and a container placement section 71 provided above the vortex mixer 70, where synthesis reaction containers 15 are placed.

The vortex mixer 70 shakes a synthesis reaction container 15 using vibration produced by transmission of the power of a motor (not shown) through an eccentric cam.

The container placement section 71 has an opening 72 for holding a synthesis reaction container 15. The opening 72 is provided in a location corresponding to a rubber shaking member 73 provided above the vortex mixer 70. By this means, the synthesis reaction container 15 is placed in the opening 72 so that it touches the rubber shaking member 73, and is shaken by the vibration of the vortex mixer 70 transmitted through the rubber shaking member 73.

During shaking by the shaking device 4, the top of the synthesis reaction container 15 is covered by a cap 74 (lid), so that the reaction solution in the synthesis reaction container 15 will not splash out. The cap 74 is provided on a driving member 75 provided in the shaking device 4, and is freely moveable horizontally and vertically.

The driving member 75 is made up of a horizontal driving shaft 76 and a vertical driving shaft 77, for moving the cap 74 horizontally and vertically, respectively. The horizontal driving shaft 76 and the vertical driving shaft 77 are connected to and driven by air cylinders 82 and 83, respectively. Driving control of the air cylinders 82 and 83 is performed by the computer 9, to be discussed later.

When a synthesis reaction container 15 is not being shaken, the cap 74 is withdrawn to a rinse port 78 provided at the rear of the container placement section 71.

In the upper part of the rinse port 78 is provided a withdrawal section 78a (washing section). When the cap 74 is withdrawn, the withdrawal section 78a has the function of washing the lower surface thereof, i.e., the surface onto which the reaction liquid may splash when the cap 74 is placed on a synthesis reaction container 15. In other words, in the lower part of the withdrawal section 78a, a tube 79 for transporting washing solvent is provided so as to provide and discharge washing solvent. At the end of the tube 79 opposite from that connected to the withdrawal section 78a is provided a liquid transport pump 80, which transports the washing solvent to the withdrawal section 78a.

Connected to the liquid transport pump 80 is a waste liquid bottle 81, which stores waste liquid produced at the time of washing the cap 74 in the withdrawal section 78a.

The cap 74 is provided with a through hole 74a, which allows gas produced in the synthesis reaction container 15 to escape. This structure can prevent bursting of the synthesis reaction container 15 due to gas produced therein during shaking.

Here, the operations of a shaking device 4 with the foregoing structure will be explained.

First, a synthesis reaction container 15 temporarily placed in the reaction container rack 1 after reaction is transported to and placed, with its blind plug 16 off, in the opening 72 of the container placement section 71 of the shaking device 4. Then, the driving member 75 moves the cap 74 from the rinse port 78 until the cap 74 lightly touches the mouth 15a of the synthesis reaction container 15. The vortex mixer 70 is always vibrating, and, simply by placing the synthesis reaction container 15 in the opening 72 of the container placement section 71 and lightly covering with the cap 74, stirring currents will be produced in the reaction liquid in the synthesis reaction container 15. Mixing is then performed for a predetermined time.

Next, after shaking, the driving member 75 removes the cap 74 from the mouth 15a of the synthesis reaction container 15, and again places the cap 74 in the withdrawal section 78a of the rinse port 78. Then, in the withdrawal section 78a, liquids attached to the lower surface of the cap 74, such as washing solvent, are removed.

After shaking as described above, the synthesis reaction container 15 is transported to the dispensing and separation device shown in FIG. 3. At this time, the solution in the synthesis reaction container 15 has separated into layers, and the dispensing and separation device 2 obtains a desired synthesis reaction solution by extracting one of these solutions separated into layers. In the dispensing and separation device 2, as discussed above, the conductivity sensor 29 detects the interface between the solutions, and one of the solutions is extracted. The solution extracted may be a desired synthesis reaction solution, or it may be a solution other than the desired synthesis reaction solution.

Accordingly, when extracting the desired synthesis reaction solution, a separate sample bottle, etc. is prepared, into which the extracted synthesis reaction solution is introduced, and then the solution may be analyzed by transporting the sample bottle, etc. to an analyzing device such as the gas chromatograph 6 or the liquid chromatograph 7. Again, when extracting a solution other than the desired synthesis reaction solution, after extraction, the synthesis reaction container 15 may be transported to the analyzing device, where the desired solution remaining in the synthesis reaction container 15 is analyzed.

In either case, it is necessary to perform preanalysis processing, using the pre-analysis processing device 5, of the solution to be analyzed by the gas chromatograph 6 or liquid chromatograph 7. Here, a standard liquid or a solvent for dilution is added to the solution to be analyzed. A standard liquid is a solution whose peak in the gas chromatograph 6 or liquid chromatograph 7 is previously known. Again, the solution is diluted when it has a high concentration and is likely to exceed the measurement range of the analyzing devices.

Next, the pre-analysis processing device 5 will be explained.

Figure 12:
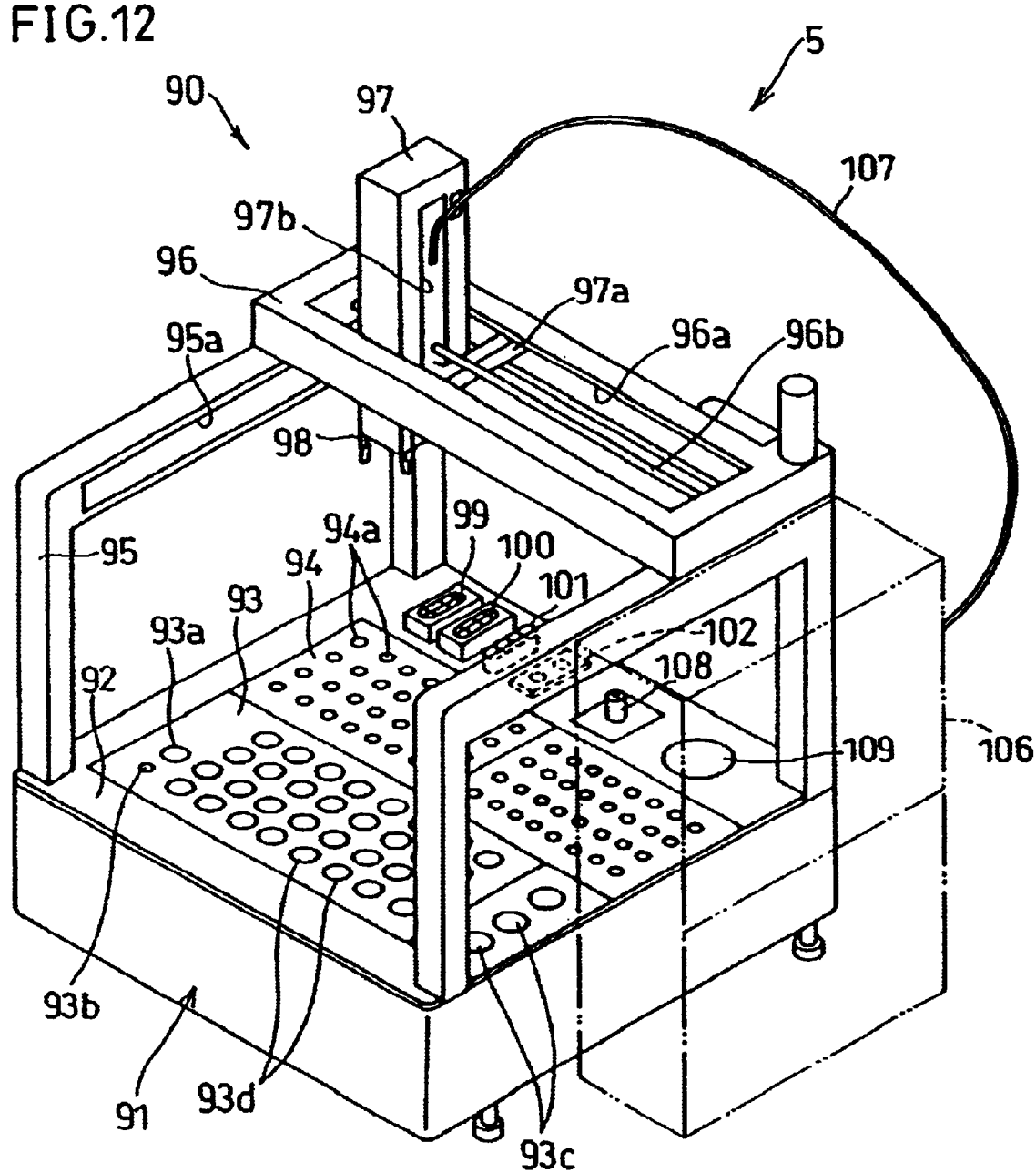
FIG. 12 is a schematic structural drawing of a pre-analysis processing device provided in the synthesis experiment automation system shown in FIG. 1.

As shown in FIG. 12, the pre-analysis processing device 5 is made up of a sampling section 90 and a sample container placement section 91.

In the sample container placement section 91, a placement stand 92 is provided with a first rack 93, in which are placed sample containers (first containers) holding separation-processed solutions, and a second rack 94 provided with placement holes 94a, in which are placed sample containers (second containers) for holding solutions sampled from the containers in the first rack 93.

The second containers placed in the second rack 94 are of smaller capacity than the first containers placed in the first rack 93, and are initially empty. When preanalysis processing operations begin, solutions stored in the first containers are introduced into the second containers, as is a standard liquid or diluting liquid necessary in analysis. Accordingly, the solutions stored in the second containers are used in the analyzing device such as the gas chromatograph 6 or liquid chromatograph 7.

At a predetermined position in the first rack 93 is provided a placement hole 93a, in which is placed a first container transported to the pre-analysis processing device 5 by the robot 8. Further, in addition to the placement hole 93a, the first rack 93 is also provided with a placement hole 93b, in which is placed a second container holding a solution which has been pre-analysis processed, for providing to a vial stocker (not shown) of the gas chromatograph 6; placement holes 93c, in which are placed standard liquid containers holding standard liquids to be introduced into the second containers; and placement holes 93d, for temporarily storing a first container after it has been placed in the placement hole 93a. Transport of first containers from the placement hole 93a to one of the placement holes 93d is performed by the sampling section 90.

In this way, introducing of desired solutions into the various containers placed in the first rack 93 and the second rack 94 is performed by the sampling section 90.

In the sampling section 90, as shown in FIG. 12, guide members 95 are provided above the right and left sides of the placement stand 92, and a horizontally moving member 96, which moves horizontally forward and backward along the top of the guide members 95, is provided in the shape of a frame.

The horizontally moving member 96 moves horizontally along the top of the guide members 95 by means of, for example, interlocking members (not shown) which fit into the guide grooves 95a, provided in the upper part of each of the guide members 95, extending forward and backward. Driving of the horizontally moving member 96 is performed by a driving means such as a motor (not shown), and driving control of the driving means is performed by the computer 9.

Further, inside the frame of the horizontally moving member 96 is provided a vertically and horizontally moving member 97, which moves in a horizontal direction perpendicular to the direction of movement of the horizontally moving member 96.

Inside the frame of the horizontally moving member 96 is provided a guide groove 96a and, parallel thereto, a guide shaft 96b, which collectively guide the movement of the vertically and horizontally moving member 97.

The vertically and horizontally moving member 97 is provided with an engaging member 97a, which engages with the guide groove 96a of the horizontally moving member 96, and with a guide groove 97b, which guides the vertical movement of the vertically and horizontally moving member 97, and which is penetrated by the guide shaft 96b.

Thus, the vertically and horizontally moving member 97 moves horizontally along the guide groove 96a of the horizontally moving member 96, and moves vertically along its own guide groove 97a, and, further, in accompaniment with the movement of the horizontally moving member 96, moves horizontally in a direction perpendicular to its own movement along the guide groove 96a. In short, the vertically and horizontally moving member 97 is freely moveable in three dimensions. Usually, the horizontally moving member 96 is withdrawn to the rear of the placement stand 92, i.e., to a position further back than the first and second racks 93 and 94.

Accordingly, the vertically and horizontally moving member 97 can move, by means of the movement of the horizontally moving member 96 and its own movement, to predetermined positions of the sample container placement section 91. Incidentally, the horizontally moving member 96 and the vertically and horizontally moving member 97 are connected to driving means (not shown), which are controlled by the computer 9.

The end of the vertically and horizontally moving member 97 pointing down toward the sample container placement section 91 is provided with an arm 98, for chucking of first containers, second containers, etc. placed on the placement stand 92.

The arm 98 of the vertically and horizontally moving member 97 is connected to an air pump 106 via a tube 107. Further, to the end of the arm 98 can be freely attached and detached fingers having various functions (to be discussed below), which are operated by air compression. A finger attached to the arm 98 is operated by adjusting the exhaust and intake quantities of the air pump 106.

In addition, first through fourth fingers 99 through 102, which can be engaged with the arm 98, are placed on the placement stand 92 opposite the withdrawn position of the vertically and horizontally moving member 97, i.e., the withdrawn position of the horizontally moving member 96. A finger is chosen, according to operating function, from among the first through fourth fingers 99 through 102, and attached to the arm 98. At this time, each of these fingers engages to the arm 98 by means of a pin and a flat spring (not shown). Among these fingers are ones functioning as sampling needle, vial finger, etc.

Figure 13:
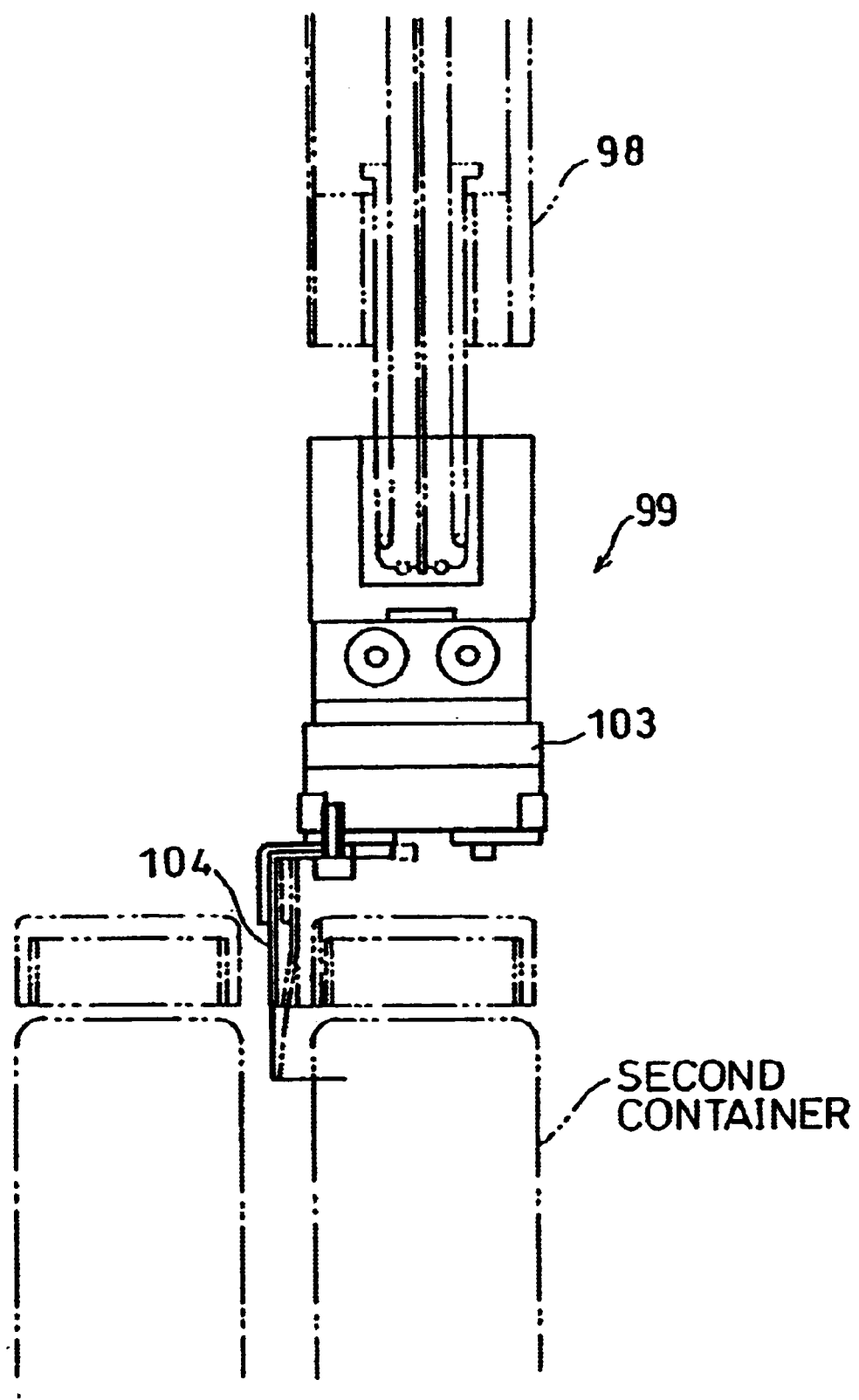
FIG. 13 is an explanatory diagram showing one example of a finger to be mounted on an arm provided in the pre-analysis processing device shown in FIG. 12.

For example, as shown in FIG. 13, the first finger 99 includes a vial finger 103 which is engaged to the arm 98 by means of a pin and a flat spring (not shown). The vial finger 103 has a claw holder 104, which chucks the upper part of a 30 ml vial (second container). The claw holder 104 chucks the upper part of the second container by moving vertically in response to air flowing through the tube 107 from the air pump 106 (both shown in FIG. 12).

Next, the second finger 100 includes a vial finger (not shown) for chucking of vials (first containers) of different capacity from those chucked by the first finger 99. As in the case of the first finger 99, the second finger 100 is also driven by means of air from the air pump 106.

Figure 14:
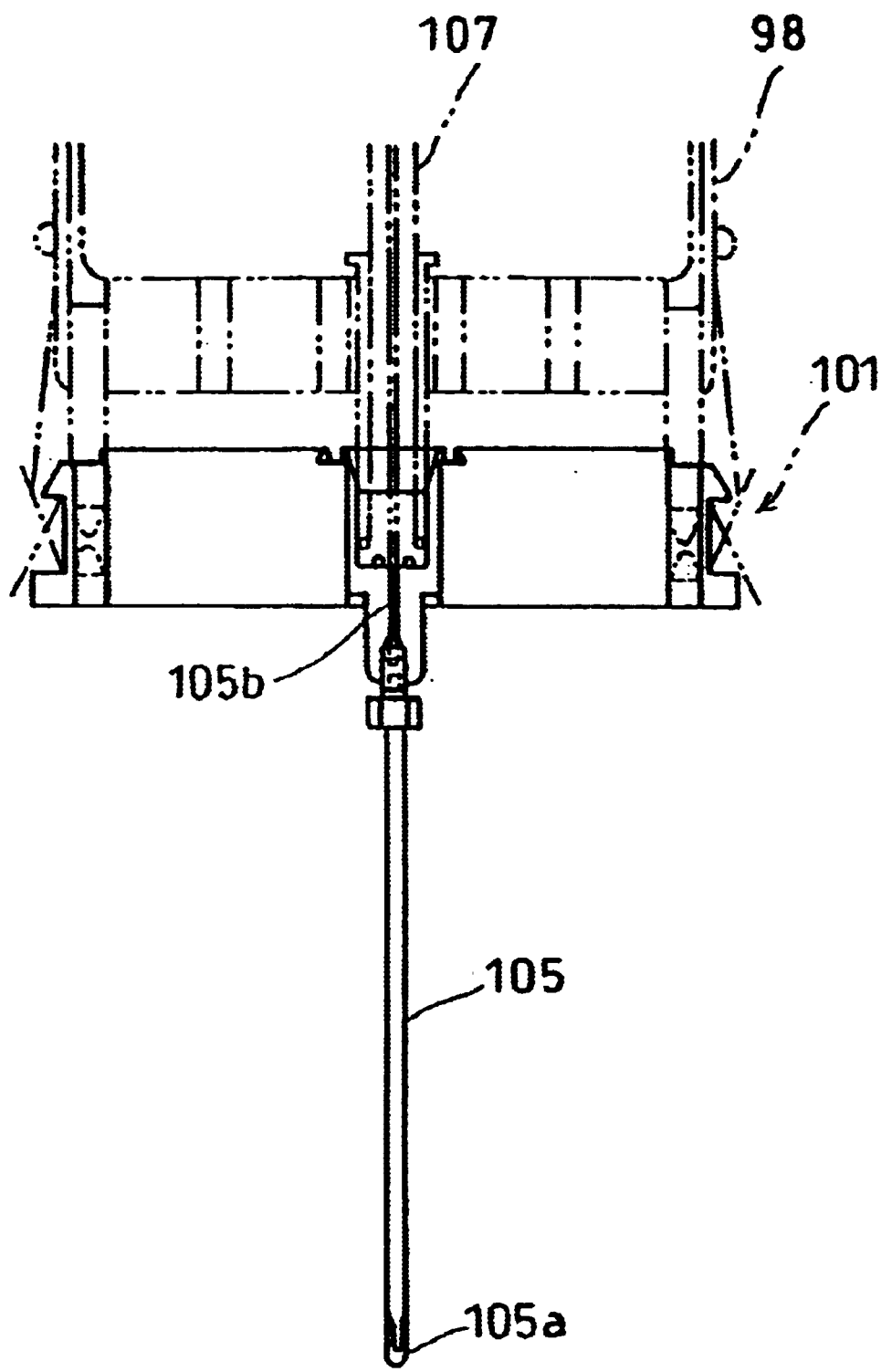
FIG. 14 is an explanatory drawing showing another example of a finger to be mounted on an arm provided in the pre-analysis processing device shown in FIG. 12.

Further, as shown in FIG. 14, the third finger 101 includes a sampling needle 105 which is engaged to the arm 98 by means of a pin and a flat spring. The sampling needle 105 is connected at its rear end 105*b* to the tube 107.

Thus air may be exhausted from the tube 107 through a tip 105*a* of the sampling needle 105, or sucked into the tube 107 through the tip 105*a*. In other words, by inserting the tip 105*a* of the sampling needle 105 into a solution in a container, and operating the air pump 106 shown in FIG. 12, a predetermined quantity of the solution in the container may be extracted or discharged.

Further, the fourth finger 102, like the third finger 101, also includes a sampling needle (not shown) which is engaged to the arm 98 by means of a pin and a flat spring. The sampling needle of the fourth finger 102 is used, for example, for extraction and discharge of solutions differing from those handled by the sampling needle 105 of the third finger 101.

Further, as shown in FIG. 12, a sample injection 108 and a touch mixer 109 are provided in the placement stand 92 near where the first through fourth fingers 99 through 102 are placed.

The sample injection 108 is connected to a sample intake of the liquid chromatograph 7, and sample solutions extracted by the sampling needle 105 of the third finger 101 which are to be examined are injected into the sample injection 108.

The touch mixer 109 mixes a solution in, for example, a second container chucked by the vial finger 103 of the first finger 99, when the second container is lightly touched to the surface of the touch mixer 109.

Here, the operations of the pre-analysis processing device 5 will be explained.

First, the device is operated so as to attach to the arm 98 a finger selected in advance by the computer 9. In this case, the device is controlled so that the first finger 99 is initially attached to the arm 98.

Next, the robot 8 transports to and places in the opening 93*a* of the first rack 93 a sample container (first container) containing a solution which has been separation processed by the dispensing and separation device 2. This first container is then chucked by the first finger 99 of the arm 98, and transported to and placed in a predetermined opening 93*d* of the first rack 93 by the movement of the vertically and horizontally moving member 97.

Next, the vertically and horizontally moving member 97 moves to its withdrawn position, and the first finger 99 attached to the arm 98 is exchanged for the third finger 101. Then the solution in the first container placed in the predetermined opening 93*d* of the first rack 93 is sampled by the sampling needle 105 of the third finger 101, and introduced into a second container stored in the second rack 94. At this time, if necessary, a diluting solution may be introduced into the second container, in addition to the solution from the first container. Operations for introducing this diluting solution are also performed by the sampling needle 105.

Next, a standard liquid stored in a container in one of the openings 93*c* of the first rack 93 is introduced into the second container by the sampling needle 105. The second container, into which the solution from the first container and the standard liquid have been introduced as described above, is then chucked by the second finger 100 attached to the arm 98 of the sampling section 90, and is placed on the touch mixer 109 for a predetermined duration, thus mixing the solutions inside.

This mixing of the solution in the second container completes pre-analysis processing. When the analyzing device to be used is the gas chromatograph 6, the second container is placed in the opening 93*b* of the first rack 93, and is then transported by the robot 8 to the vial stocker of the gas chromatograph 6. When the analyzing device to be used is the liquid chromatograph 7, on the other hand, the second container after mixing is temporarily placed in an opening 94*a* of the second rack 94, and the solution therein is sampled by the sampling needle 105 and then injected into the sample injection 108.

A solution which has been pre-analysis processed in this way by the pre-analysis processing device 5 is finally analyzed by the gas chromatograph 6 or the liquid chromatograph 7, and thus data on yield, etc. is obtained. This data on yield, etc. is stored in a memory device within or external to the computer 9, and may, as necessary, be retrieved and used as reference material for subsequent experiments.

In the foregoing synthesis experiment automation system, the robot 8 is used for transporting containers such as the synthesis reaction containers 15 among the reaction container rack 1, the dispensing and separation device 2, the reaction device 3, the shaking device 4, the pre-analysis processing device 5, and the gas chromatograph 6. The robot 8 is an industrial robot, and driving control thereof is performed by the computer 9.

Next, the robot 8 will be explained.

Figure 15A:
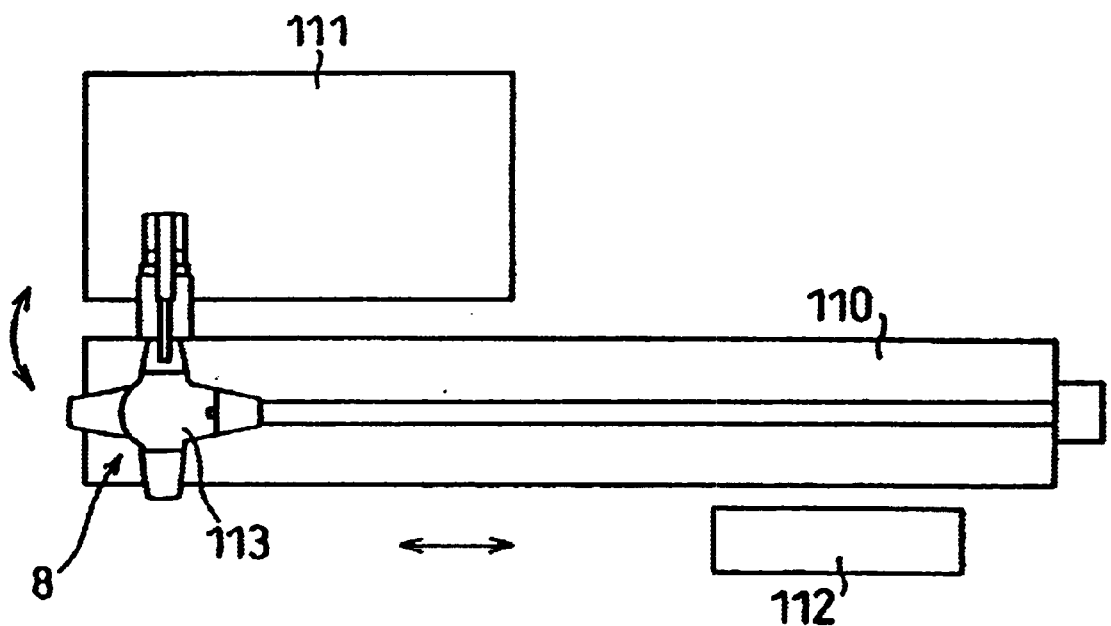
FIG. 15 (*a*) is a plan view showing a robot provided in the synthesis experiment automation system shown in FIG. 1.

As shown in FIGS. 15(*a*) and 15(*b*), the robot 8 is structured so that a main body 113 travels from one end to the other of a robot traveling rail 110 in the shape of a straight line. A multi-shaft traveling axis having one shaft with high extensibility is used for the robot traveling rail 110. Basically, the robot 8 is used as a means of transporting containers, etc. to and from devices 111 and 112 of the synthesis experiment automation system (such as the reaction container rack 1, the reaction device 3, etc.), which are arranged along the robot traveling rail 110. In other words, it is sufficient if the devices 111 and 112 are positioned within the range of action of the robot 8.

Figure 15B:
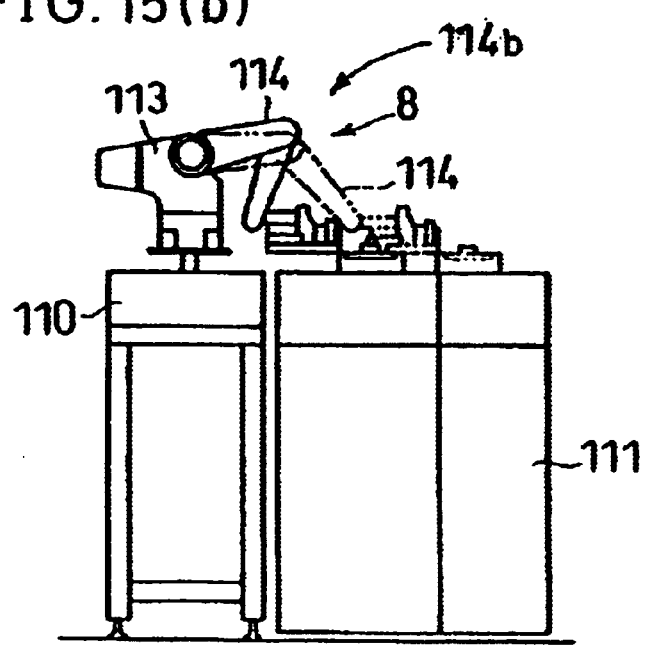

The main body 113 of the robot 8 is provided with an arm 114 having a polycentric joint 114*b* which turns freely on the main body 113. As shown in FIG. 15(b), the end of the arm 114 is freely moveable above the device 111, and thus the arm 114 serves to transport containers, etc.

Accordingly, if the computer 9 performs suitable driving control of the main body 113 and the arm 114 of the robot 8, containers, etc. can be efficiently transported between the devices 111 and 112.

Figure 16A:
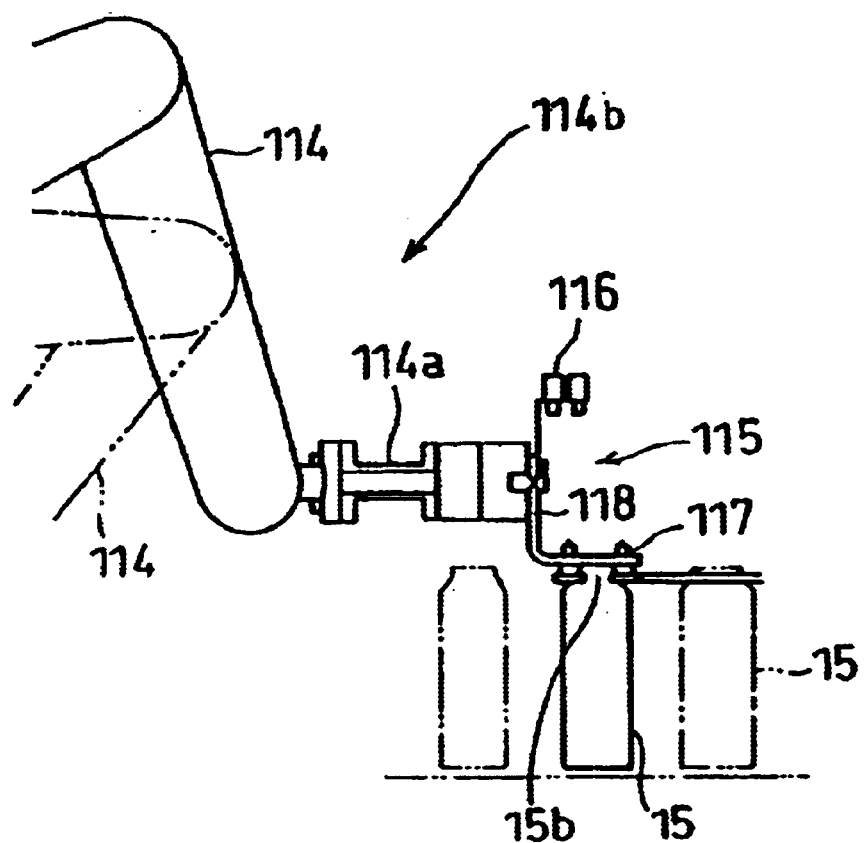
FIG. 16(*a*) is a side view of an arm of the robot shown in FIGS. 15(*a*) and 15(*b*).
Figure 16B:
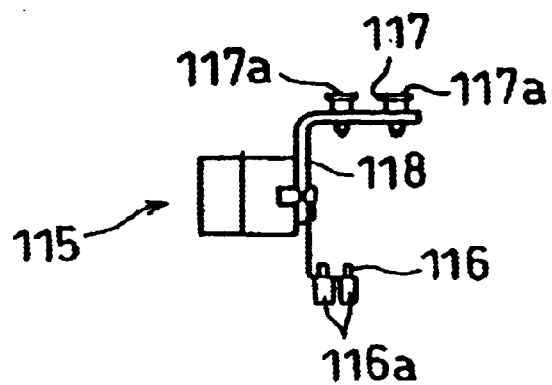

Further, as shown in FIGS. 16(a) and 16(b), a tip 114a of the arm 114 is provided with a detachable grasping section 115. The grasping section 115 is provided with a first finger 116 and a second finger 117, each of which is capable of grasping containers of a different size. The first and second fingers 116 and 117 are attached to the respective ends of a supporting member 118, which is rotatable 180° with respect to the tip 114a of the arm 114.

The second finger 117 is provided so as to grasp a neck 15b of the upper part of a synthesis reaction container 15, and the first finger 116 is provided so as to grasp the neck of a container of smaller capacity than the synthesis reaction containers 15.

Specifically, the second finger 117 is provided with four grasping members 117a, which support the object to be chucked, i.e., the neck 15b of the synthesis reaction container 15, at four points. In the same way, the first finger 116 is provided with four grasping members 116a. However, the structure of the fingers is not limited to the foregoing structure, and any structure capable of grasping the object to be chucked (container, etc.) is acceptable.

The first finger 116 and the second finger 117 may be used alternately by rotating the supporting member 118 180°. For example, if the second finger 117 is initially turned down and the first finger 116 turned up, a container smaller than the synthesis reaction container 15 may be grasped by rotating the supporting member 118 180° so that the first finger 116 is turned down, and grasping the container using the first finger 116.

In addition, since the grasping section 115 is freely rotatable by means of the supporting member 118, when, for example, a synthesis reaction container 15 containing a solution is chucked in the second finger 117, a solution in the synthesis reaction container 15 can be discharged by rotating the supporting member 118 180°.

Further, various grasping sections 115 are prepared according to the needs of the experiments, etc., and are attached to and detached from the arm 114 as necessary. Attachment of the grasping sections 115 to the arm 114 may be performed manually, by the operator, as needed, or automatically, as with attachment of the first through fourth fingers 99 through 102 to the arm 98 of the preanalysis processing device 5.

The following will explain the operations of the synthesis experiment automation system with the foregoing structure with reference to FIG. 1.

First, the robot 8 chucks a synthesis reaction container 15 stored in the reaction container rack 1, and transports it to the dispensing and separation device 2. After giving the interior of the chucked synthesis reaction container 15 a nitrogen atmosphere, specified reagents and solvents are introduced therein. The robot 8 then transports the synthesis reaction container 15 containing the reagents and solvents to a reaction position in one of the temperature regulator units 30 of the reaction device 3. At this time, as necessary, the weight of the synthesis reaction container 15 when empty and its weight when filled with the reagents and solvents may be measured using an electronic balance, etc. Weight data from this measurement is sent to the computer 9.

After completion of the synthesis reaction, the robot 8 again transports the synthesis reaction container 15 to and places it in the reaction container rack 1, where it waits with its mouth 15a covered with a blind plug 16.

Next, the robot 8 transports a synthesis reaction container 15 with a completed synthesis reaction, from which the blind plug has been removed, to the shaking device 4, where the reaction liquid in the synthesis reaction container 15 is stirred for a predetermined duration and separated into layers. Then the robot 8 transports the synthesis reaction container 15 containing the solution separated into layers to a separation position of the dispensing and separation device 2. Here, the conductivity sensor 29 of the dispensing and separation device 2 is inserted into the synthesis reaction container 15, the interface between the separated layers is detected, and, based on the detected results, an indicated solution is extracted and introduced into a sample bottle.

This sample bottle is transported to the pre-analysis processing device 5, where a pre-analysis processed solution is prepared by adding to the solution in the sample bottle a diluting liquid or a standard liquid. Then predetermined analysis of this solution is performed by the gas chromatograph 6 or the liquid chromatograph 7, and the yield of the synthesis reaction is determined.

The actions of the robot 8 in transporting the synthesis reaction container 15 are controlled on the basis of an execution schedule program in the computer 9, and these actions are performed as many times as there are synthesis reaction experiments. Control of the robot 8 and of the various devices of the synthesis experiment automation system by the computer 9 will be discussed later.

As discussed above, in the synthesis experiment automation system according to the present invention, the computer 9 performs driving control of the robot 8 and the various devices used in the experiments. The following will explain the synthesis experiment automation system software. In the present invention, a personal computer is used for the computer 9, because of its general applicability. Again, programs used in the computer 9 are prepared using a programming language capable of operating under the OS (operating system) of the Microsoft product Windows™ (version 3.1 or higher). Accordingly, as long as it is capable of operating under the foregoing OS, the programming language is not limited to any particular language.

First, the manner of connecting the computer 9 to the robot 8 and to the various devices of the synthesis experiment automation system will be explained.

As shown in FIG. 17, the computer 9 is provided with at least two serial ports (in the present embodiment, two COM ports COM 1 and COM 2), and to these two serial ports are connected, respectively, the robot 8 and the various devices of the synthesis experiment automation system. The serial ports are RS232C terminals or terminals governed by RS232C specifications.

Accordingly, in the synthesis experiment automation system, the dispensing and separation device 2, the reaction device 3, the shaking device 4, the pre-analysis processing device 5, the gas chromatograph 6, and the liquid chromatograph 7 (hereinafter collectively referred to as the "system devices") must have a communications function for sending and receiving data via the serial port of the computer 9. Specifically, it is sufficient if the system devices are provided with RS232C terminals, or with communications terminals governed by RS232C specifications, as serial ports.

The robot 8 is connected to COM 1 of the computer 9, and the dispensing and separation device 2, the reaction device 3, the shaking device 4, the pre-analysis processing device 5, the gas chromatograph 6, and the liquid chromatograph 7 are connected, via a signal distributor 120 such as a peripheral box, to COM 2 of the computer 9. The reason the robot 8 and the system devices of the synthesis experiment automation system are connected to different serial ports is that the communications data specifications of the robot 8 differ from those of the system devices.

The signal distributor 120 sends signals from the computer 9 to desired system devices, and selectively sends signals from the system devices to the computer 9. The signal distributor 120 is necessary because the communication function of the RS232C terminal is not capable of continuously sending to the system devices simultaneously.

Figure 18:
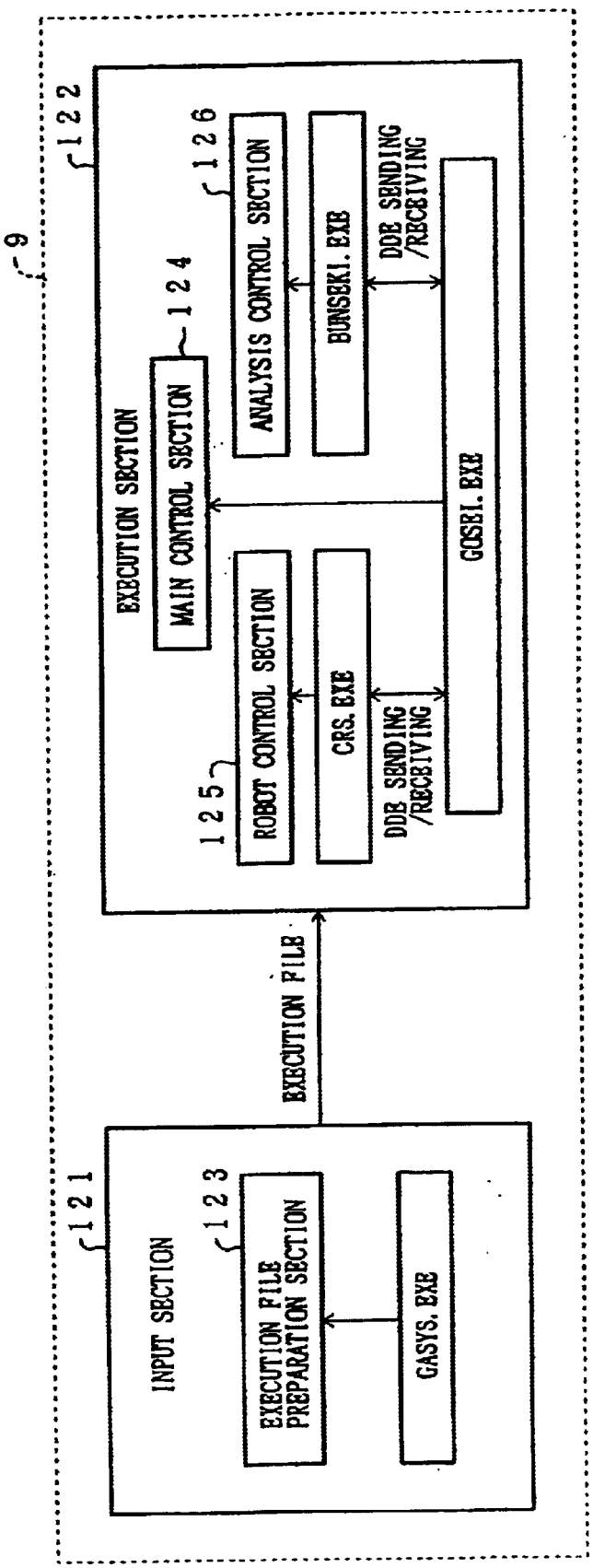
FIG. 18 is an explanatory drawing showing the internal structure of a computer shown in FIG. 17.

As shown in FIG. 18, the computer 9 is made up of an input section 121, which chiefly performs preparation of execution files, showing the steps of a synthesis reaction, for execution of a synthesis experiment to be performed by the synthesis experiment automation system; and an execution section 122, which performs operations control of the synthesis experiment automation system based on an execution file. In the input section 121, preparation of an execution file is performed by means of an application activation program called GASYS.EXE, and in the execution section 122, operations control is performed by means of three application activation programs called GOSEI.EXE, CRS.EXE, and BUNSEKI.EXE.

GOSEI.EXE, CRS.EXE, and BUNSEKI.EXE perform control while mutually sending and receiving information by means of DDE (Dynamic Data Exchange).

GASYS.EXE is a tool application for preparing execution files for the synthesis experiment automation system.

GOSEI.EXE is the central program of the execution section 122, and includes schedule management using a timer. Execution of GOSEI.EXE begins based on an execution file prepared in the input section 121.

CRS.EXE is a program which sends control signals to the robot 8. Control operations based on these signals are sent from GOSEI.EXE by means of DDE.

BUNSEKI.EXE is a program which sends control signals to an analyzing device (EX-Multi). Control operations based on these signals are sent to the various analyzing devices via GOSEI.EXE.

The input section 121 includes an execution file preparation section 123, where execution files are prepared. In the execution file preparation section 123, preparation of an execution file is begun by activating the program execution file GASYS.EXE. In an execution file are written the number of synthesis reaction experiments, experiment conditions, etc. The details of the execution file preparation section 123 will be discussed later.

The execution section 122 includes a main control section 124, which controls the various devices of the synthesis experiment automation system, a robot control section 125, which controls the robot 8, and an analysis control section 126, which controls the analyzing devices. In the main control section 124, programs concerned with main control are executed by activating the program execution file GOSEI.EXE. In the robot control section 125, programs concerned with robot control are executed by activating the program execution file CRS.EXE. In the analysis control section 126, programs concerned with analysis control are executed by activating the program execution file BUNSEKI.EXE.

GOSEI.EXE of the execution section 122 performs schedule management by means of a timer event. This is because, in Windows™, it is difficult to prepare applications in which a single program execution file (.EXE) performs multiple tasks. In other words, the execution section 122 performs schedule management of multiple experiments by stopping the flow of processing for each experiment after a period of several tens of milliseconds to 1 second (usually, the timing with which control signals are sent to a system device), and shifting to control of another experiment.

Generally, when a plurality of synthesis experiments are to be performed simultaneously, performing the experiments without order and without some sort of restriction leads to great problems.

For this reason, conventional control programs for performing a plurality of synthesis experiments solved the foregoing problem at the stage of preparation of experiment files (corresponding to the execution files of the present invention), by calculating the time needed for the operations of each unit experiment, preparing a timetable for each experiment, and combining these timetables in a manner so as not to exceed the limits of hardware (i.e., staggering the commencement times for each experiment).

However, with this kind of conventional control program, since the timetable must be prepared at the time of preparation of the experiment file, it is prepared by means of estimates based on the time required for each unit operation, for example, "At this moment the robot should be here," "The shaking device should be free," etc. This leads to the problem that the system is unable to promptly respond to unforeseen hardware circumstances.

In contrast, in the present invention, since it is always in communication with the system devices by means of the communication function, the computer 9 is always aware of the status of the system devices. For this reason, if unforeseen circumstances arise in the hardware, the system can promptly respond thereto.

The following will explain in detail the execution file preparation section 123 of the input section 121.

As shown in FIG. 19, the execution file preparation section 123 is made up of four programs: an experiment file preparation section 127, for preparing experiment files which set experiment parameters such as the temperature, reagents, etc. necessary for a synthesis experiment; an environment file preparation section 128, for preparing environment files which set the environment of the synthesis experiment automation system, including the action speed of the robot 8, the size of the reaction container rack 1, etc.; and a reagent/solvent name recording section 129, for recording the names of reagents, solvents, etc. to be used in synthesis experiments. These four programs are executed by activating GASYS.EXE.

In the experiment file preparation section 127, experiment files may be prepared using at least one of a simple mode and a detailed mode. In other words, experiment files may be prepared using only the simple mode, or using the simple mode and the detailed mode, or using only the detailed mode.

The simple mode is an experiment file preparation mode set up so that an experiment specialist not used to operating the synthesis experiment automation system may easily prepare an experiment file. In the simple mode, an experiment file may be prepared by changing only the reagents and solutions, reaction temperatures, etc. of previously prepared synthesis reaction operation control algorithms; for example, by choosing from among three courses: (1) optimum temperature/time investigation course, (2) optimum reagent/solvent investigation course, and (3) optimum mole ratio investigation course.

The detailed mode, on the other hand, is an experiment file preparation mode in which detailed selection and setting of the various parameters and sequences (unit operations) of a synthesis experiment are performed.

Generally, when preparing an experiment file, setup using the simple mode is followed by setup using the detailed mode. However, as mentioned above, an experiment file may be prepared without selecting the simple mode, using only the detailed mode, or by using only the simple mode.

The environment file preparation section 128 executes a program for preparing a file setting up the environment, including the speed of motion of the robot 8, speed of sampling and discharge in the diluter, number of times of washing of a tube when switching the reagent to be transported thereby, and the arrangement of the various devices of the synthesis experiment automation system, such as the size of the reaction container rack 1, etc.

Further, the reagent/solvent name recording section 129 executes a program for recording the names of the various reagents and solvents used in the synthesis experiments.

The programs of the execution file preparation section 123 of the input section 121 are activated when the operator selects a Windows™ program-activation icon displayed on a monitor (not shown) of the computer 9. This icon is set up so as to activate GASYS.EXE. Then, after the programs of the execution file preparation section 123 have been activated, an input setup main screen (not shown) is displayed on the monitor. On the display of this input setup main screen, the simple mode or the detailed mode may be selected.

Next, according to the object of the experiment, the operator chooses the simple mode or the detailed mode, and inputs the experiment conditions. At this time, after inputting experiment conditions using the simple mode, the detailed mode may be selected and further experiment conditions inputted. Again, the detailed mode may be initially selected, and experiment conditions inputted therein.

In both modes, the experiment conditions are inputted by selecting items for reagents, solutions, etc., or by inputting values for reaction temperature, reaction time, etc. At this time, error checking of the selected items (when selecting items) or of the value range (when inputting values) is performed. The operator is informed of any error by means of a warning. This warning is made by outputting a sound from a speaker, etc. of the computer 9, and by displaying a warning on the screen.

In this way, error checking is performed during inputting of the experiment conditions. When all experiment conditions have been inputted, a file to be sent to the execution section 122 is prepared. At the time of preparing this file, the operator is informed of any error in the inputted items by a warning, as above.

On the input setup main screen, in addition to icons for selection of the simple and detailed modes, icons for environment setup and reagent/solvent recording are also displayed. By selecting one of these icons, the operator can switch to the environment setup screen or the reagent/solvent recording screen, as desired.

Accordingly, preparation of execution files in the input section 121 is carried out according to, for example, a screen 200, shown in FIG. 23, which is displayed on the monitor (not shown) of the computer 9.

On the basis of execution files prepared in this way in the input section 121, the execution section 122 performs operations control of the synthesis experiment automation system.

Here, the main control section 124, the robot control section 125, and the analysis control section 126 of the execution section 122 will be explained in detail.

Figure 20:
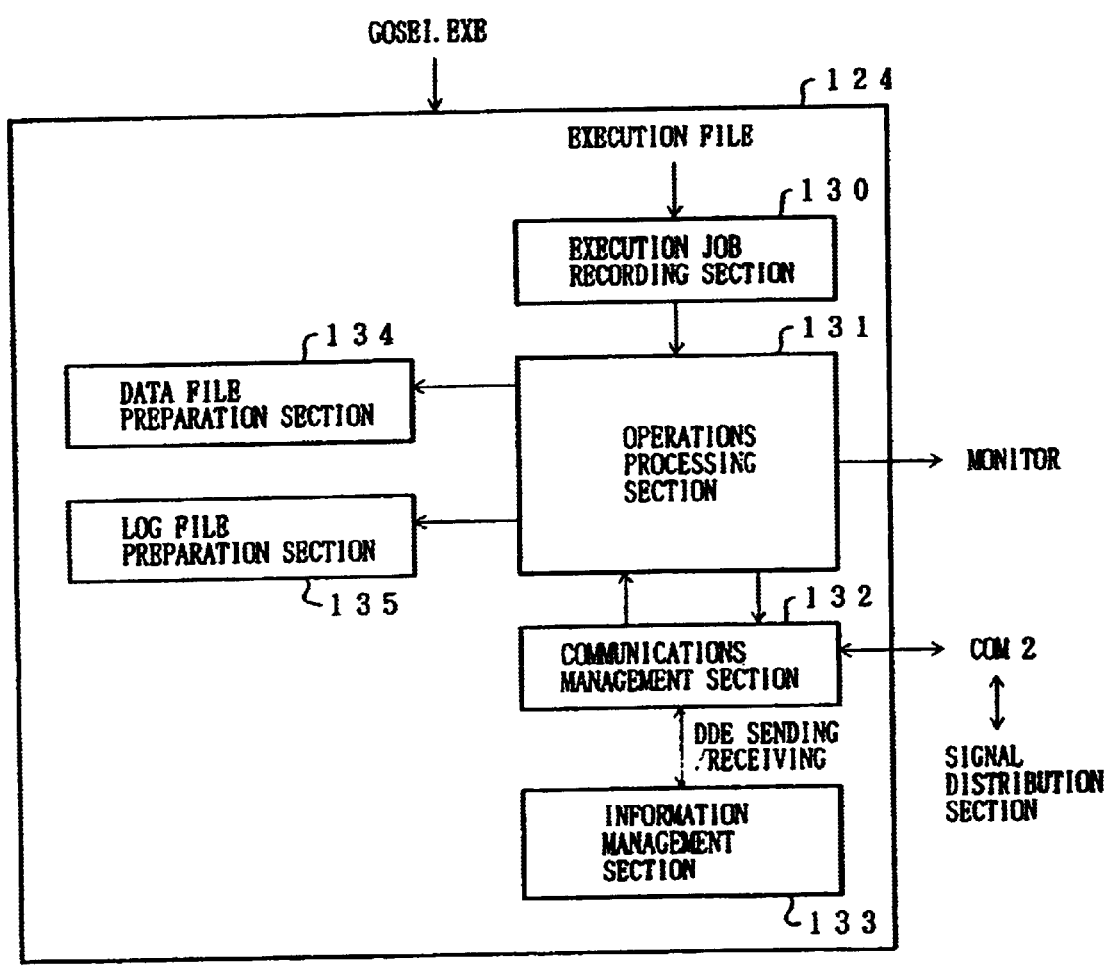
FIG. 20 is an explanatory drawing showing a main control section in an execution section of the computer shown in FIG. 18.

As shown in FIG. 20, the main control section 124 is made up of six programs: an execution job recording section 130, an operations processing section 131, a communications management section 132, an information management section 133, a data file preparation section 134, and a log file preparation section 135. These six programs are executed by activating the program GOSEI.EXE.

The execution job recording section 130 is a program which reads a selected execution file from among the execution files prepared in the execution file preparation section 123, and records the execution file as a number of execution jobs, one for each set temperature. These execution jobs are recorded for each set temperature, and are read into the operations processing section 131 with a set timing. The synthesis experiments are performed execution job by execution job.

At the time of reading each execution file, the execution job recording section 130 checks the set environment values and sequence parameters, confirms the devices of the synthesis experiment automation system and the arrangement of the devices and implements to be used, etc. For example, with regard to confirmation of system devices, before recording the execution file as execution jobs, an initializing action command is sent to each device to be used, and it is confirmed whether each device receives and sends that action command correctly. At this time, if it is found that a device is not correctly receiving and sending the action command (power is not switched on, a communications connector is not attached, etc.), a warning is given to the operator of the synthesis experiment automation system, and commencement of experiment operations is suspended. Then, after the problem (disconnection, etc.) is resolved, the system devices are again confirmed, and upon completion of confirmation of the execution file and the system devices, recording of execution jobs is performed.

The reason the contents of the execution files are checked in the execution job recording section 130 prior to recording of execution jobs is that, since the execution files are written in the form of regular text files, the contents of the text files may be easily changed using an editor, etc.

The operations processing section 131 operates the synthesis experiment automation system based on the contents of the execution jobs recorded in the execution job recording section 130. At this time, the operations processing section 131 executes programs for scheduling execution of experiments using a timer, ordering of execution jobs, arrangement of experiment devices and implements to be used, controlling DDE communications, controlling the actions of the system devices, etc.

With control by the operations processing section 131, four execution jobs can be executed simultaneously, because there are four temperature regulator units 30. When more than four execution jobs are to be performed, an execution job for an experiment in a temperature regulator unit 30 may be commenced when the execution job for the previous experiment in that temperature regulator unit 30 has been completed. In other words, there are four temperature regulator units 30 in the present embodiment, but increasing the number of temperature regulator units 30 will also increase the number of execution jobs which can be performed simultaneously.

Figure 24:
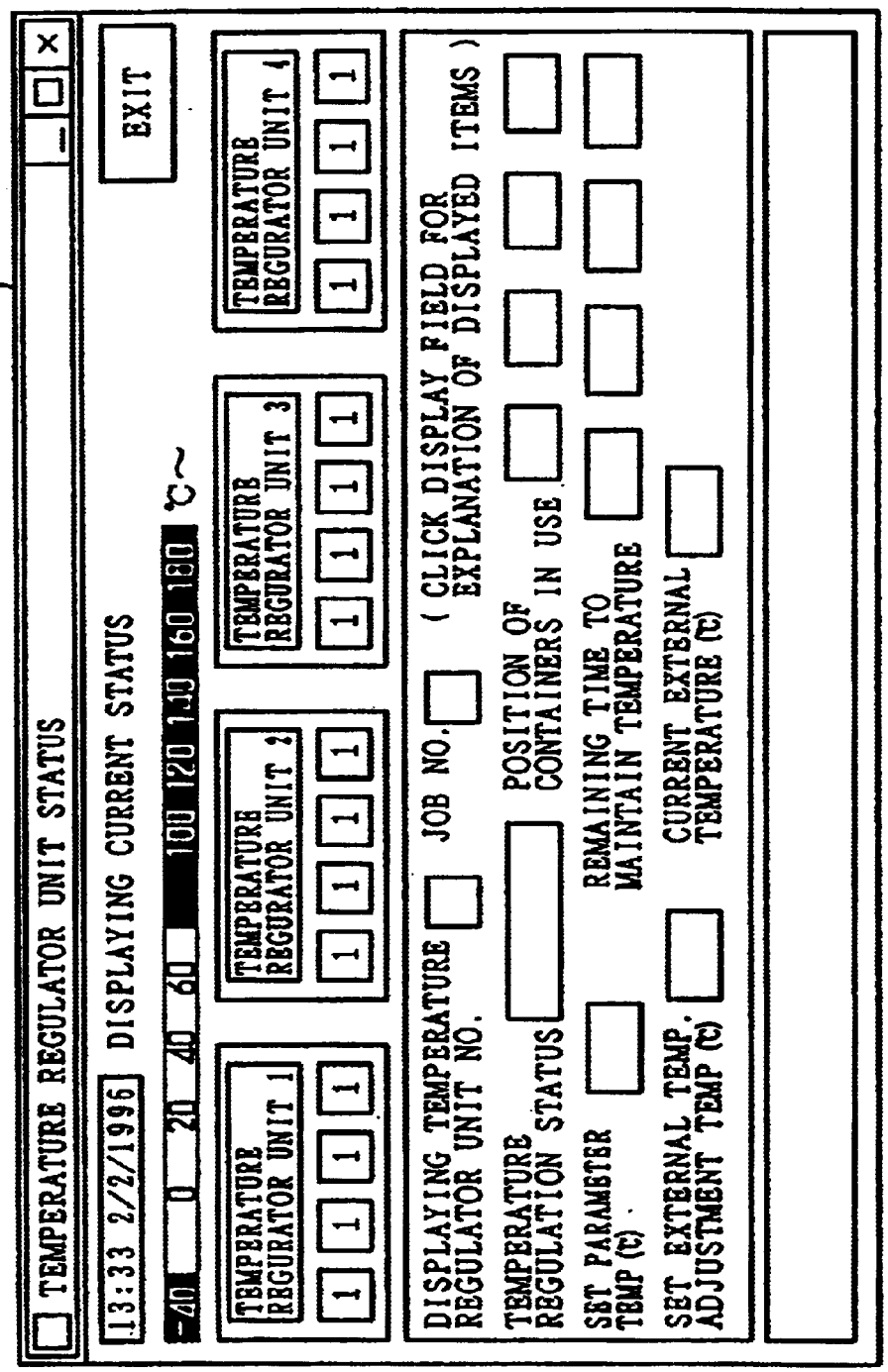
FIG. 24 is a an explanatory drawing showing one example of a screen showing the state of progress of an experiment in the synthesis experiment automation system shown in FIG. 1.

While the synthesis experiments are being carried out, execution screens like the execution screen 201 shown in FIG. 24, which display the state of progress of execution of the experiments, are displayed on the monitor (not shown) of the computer 9. Examples of execution screens are "Vial Execution Chain Diagram," which displays the progress of the experiment for each synthesis reaction container 15, "Temperature Regulator Unit Status," which displays the temperature of each temperature regulator unit 30 in the order of their arrangement, and "Working Jobs/Waiting Jobs," which displays the progress of each job.

Control signals produced by the operations processing section 131 based on the execution jobs are sent to the system devices through the communications management section 132, and information from the system devices is received through the communications management section 132.

Sending of control signals by the communications management section 132 uses COM 2. The communications management section 132 performs sending of the control signals according to a separate timer independent from that of the operations processing section 131. This is because multiple control signals cannot be sent continuously through COM 2.

The communications management section 132 sends information to and receives information from the information management section 133 by means of DDE. The information management section 133 is an information management program which manages the status of the operation environment, sending and receiving to the robot 8, peripheral sending and receiving, etc. in the synthesis experiment automation system during the synthesis experiment.

The information management program in the information management section 133 sends control signals (commands) to each system device in succession, with a short time interval according to the timer of the operations processing section 131, and checks whether that system device is ready to execute the next execution job, by means of bit-based information management means called "flags" provided in the program. Then, if that system device is ready to execute the next execution job, the information management section 133 controls the operations processing section 131 so as to send operating signals to that system device. If no system device is ready to execute the next execution job, the information management section 133 repeats this checking until a job which can be executed is found among the recorded execution jobs.

Further, the main control section 124 also includes a program called the data file preparation section 134, which files various data arising from the experiments conducted according to the execution jobs, such as weight measurements of reagents, solutions, and reaction liquids, etc.

Again, in addition to the data file preparation section 134, the main control section 124 also includes a program called the log file preparation section 135, which prepares log files recording the communications between the computer 9 and the system devices during the synthesis reactions, such as how the various system devices operated, what commands they operated in response to, etc.

The data files and log files prepared by the data file preparation section 134 and the log file preparation section 135, respectively, are stored in a memory device within or external to the computer 9, and can be referred to or used as necessary.

Next, the robot control section 125 will be explained in detail. Since the robot 8 is used for transporting containers such as the synthesis reaction containers 15 among the various devices of the synthesis experiment automation system, schedule management thereof is performed by the operations processing section 131. However, because of the independence of the actions of the robot 8 and the uniqueness of the specifications of the communications signals used, the section for sending and receiving communications signals for those actions is controlled by an independent control section. This control section is the robot control section 125.

Figure 21:
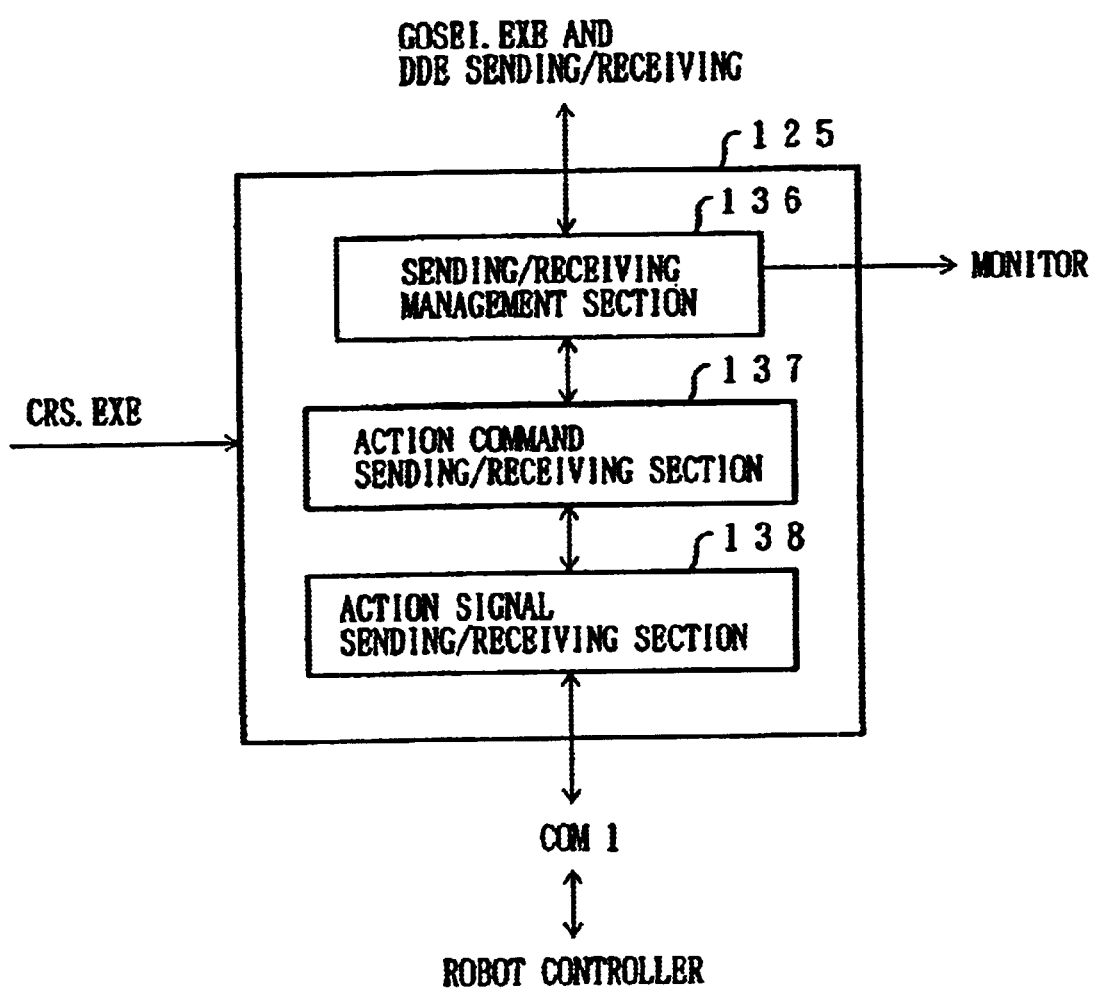
FIG. 21 is an explanatory drawing showing a robot control section in an execution section of the computer shown in FIG. 18.

As shown in FIG. 21, the robot control section 125 is made up of three programs: a sending/receiving management section 136, which performs sending to and receiving from GOSEI.EXE by means of DDE; an action command sending/receiving section 137, which receives action commands from DDE information signals, and converts these action commands into action signals for the robot 8; and an action signal sending/receiving section 138, which sends and receives action signals.

The action signal sending/receiving section 138 is a program which manages sending and receiving of action signals between COM 1 and a controller of the robot 8.

The programs making up the robot control section 125 are executed by activating CRS.EXE. CRS.EXE is activated by DDE communication with GOSEI.EXE at the time of activation of GOSEI.EXE.

During execution of the action signal sending/receiving section 138 program, a setup screen, for changing previously set movement positions of the robot 8 (hereinafter referred to as "locations"), and a terminal screen, for sending commands as desired, for example to move the robot 8 to a particular location, may be displayed on the monitor via the sending/receiving management section 136. These two functions, however, are not generally used in typical synthesis experiments.

The following will explain the analysis control section 126. As in the case of the robot control section 125, because of the independence of the actions of the analyzing devices (the gas chromatograph 6 and the liquid chromatograph 7) and the uniqueness of the communications signals used, the section for sending and receiving the communications signals for those actions is controlled by an independent control section. This control section is the analysis control section 126.

Figure 22:
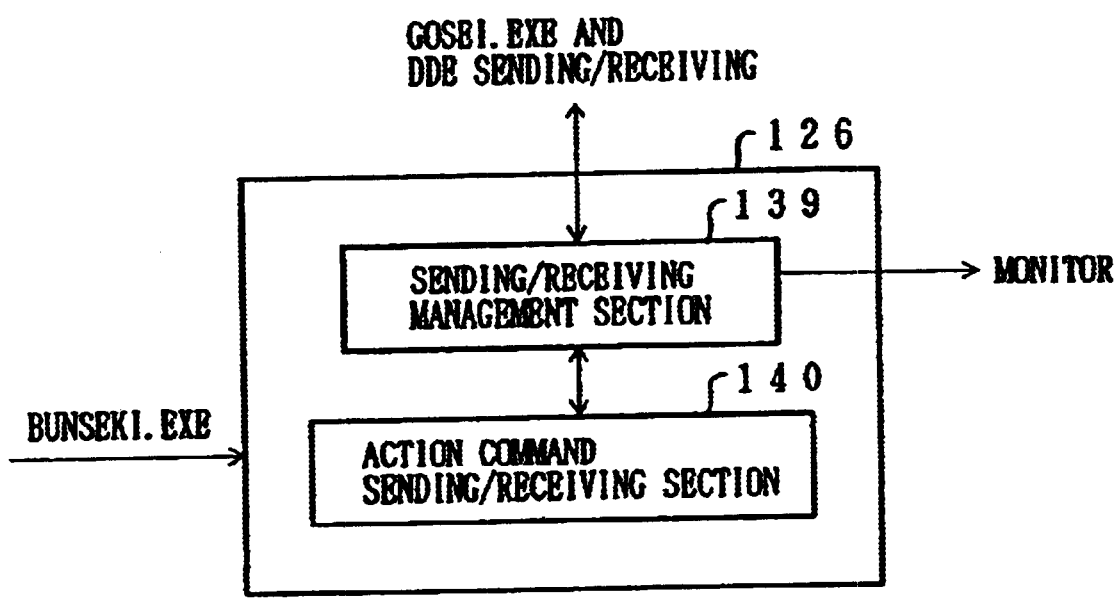
FIG. 22 is an explanatory drawing showing an analysis control section in an execution section of the computer shown in FIG. 18.

As shown in FIG. 22, the analysis control section 126 is made up of two programs: a sending/receiving management section 139, which performs sending to and receiving from GOSEI.EXE by means of DDE; and an action command sending/receiving section 140, which receives action commands from DDE information signals, and sends action commands.

Incidentally, with regard to management of the movement positions, etc. of each analyzing device, since this information is stored in the analyzing device itself, there is no need to display a terminal screen, etc. as with the robot control section 125.

The programs making up the analysis control section 126 are executed by activating BUNSEKI.EXE. BUNSEKI.EXE is activated by DDE communication with GOSEI.EXE at the time of activation of GOSEI.EXE. Then, control operations for the analyzing devices are performed by action signals sent from GOSEI.EXE by DDE communication, and control signals are sent to the analyzing devices through GOSEI.EXE.

The following will explain the flow of operations of the synthesis experiment automation system as a whole with reference to the flow charts shown in FIGS. 25 through 28. However, prior to putting the synthesis experiment automation system into operation, the operator performs experiment preparations such as turning on the power of each system device, supplying reagents and solvents, placing synthesis reaction containers 15, etc. When experiment preparations are complete, the computer 9 is put in operation.

Figure 25:
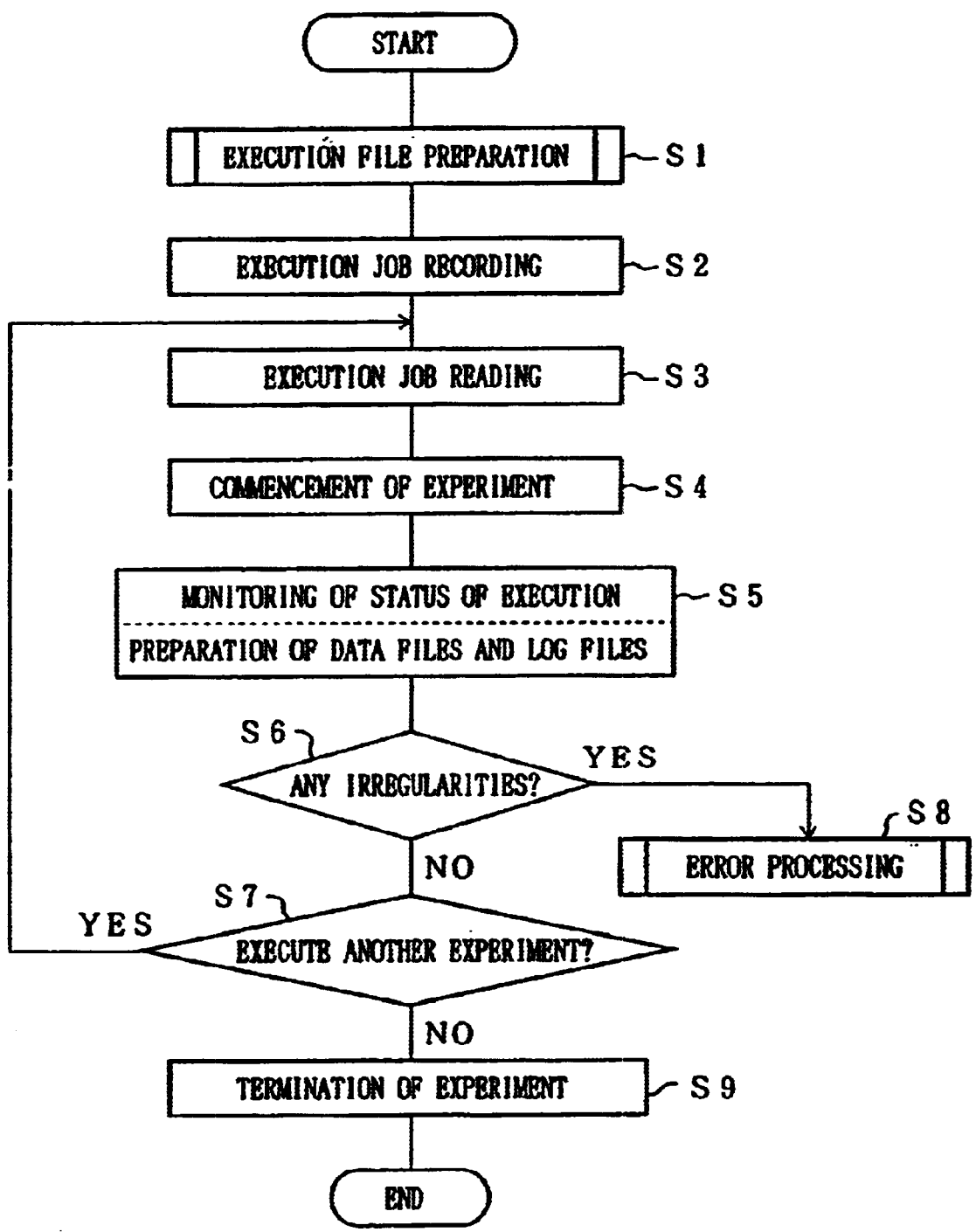
FIG. 25 is a flow chart showing the flow of processing in the synthesis experiment automation system shown in FIG. 1.

First, as shown in FIG. 25, execution files are prepared according to the synthesis experiment to be carried out (S1). A sub-routine for preparation of the execution files will be discussed later.

Next, execution jobs are recorded based on the execution files prepared (S2). The sub-routine for recording of execution jobs will also be discussed later.

Next, the execution jobs recorded in S2 are read (S3). Here, the execution jobs prepared for each reaction temperature written in the execution file, and the execution file itself, are checked for irregularities.

Then the experiment is commenced based on the execution jobs (S4). In the synthesis experiment automation system according to the present embodiment, since the reaction device 3 includes four temperature regulator units 30, which can be set to different reaction temperatures, four execution jobs can be executed.

Then, the status of execution of the experiment is displayed on the monitor, and data files recording various data obtained during the experiment, and log files showing the status of communications between the system devices and the computer 9, are prepared (S5) Accordingly, during execution of the experiment, the operator can monitor the status of execution, enabling discovery of irregularities during the experiment.

Next, the operator determines whether any irregularity occurred during monitoring of the execution status (S6). Here, if there was no irregularity, the operator determines whether to execute another experiment (S7).

If the operator determines in S6 that an irregularity occurred, the operator proceeds to a subroutine for error processing. This sub-routine will be discussed later.

If, in S7, another experiment is to be performed, operations return to S3, where another execution job is read. If, on the other hand, in S7, no further experiments are to be performed, the experiment is terminated (S9). Here, termination of the experiment means termination of all synthesis reactions in the synthesis experiment automation system.

The following will explain the execution file preparation sub-routine. Here, "execution file" refers to all data prepared and recorded by the experiment file preparation section 127, the environment file preparation section 128, and the reagent/solvent name recording section 129 of the execution file preparation section 123.

Figure 26:
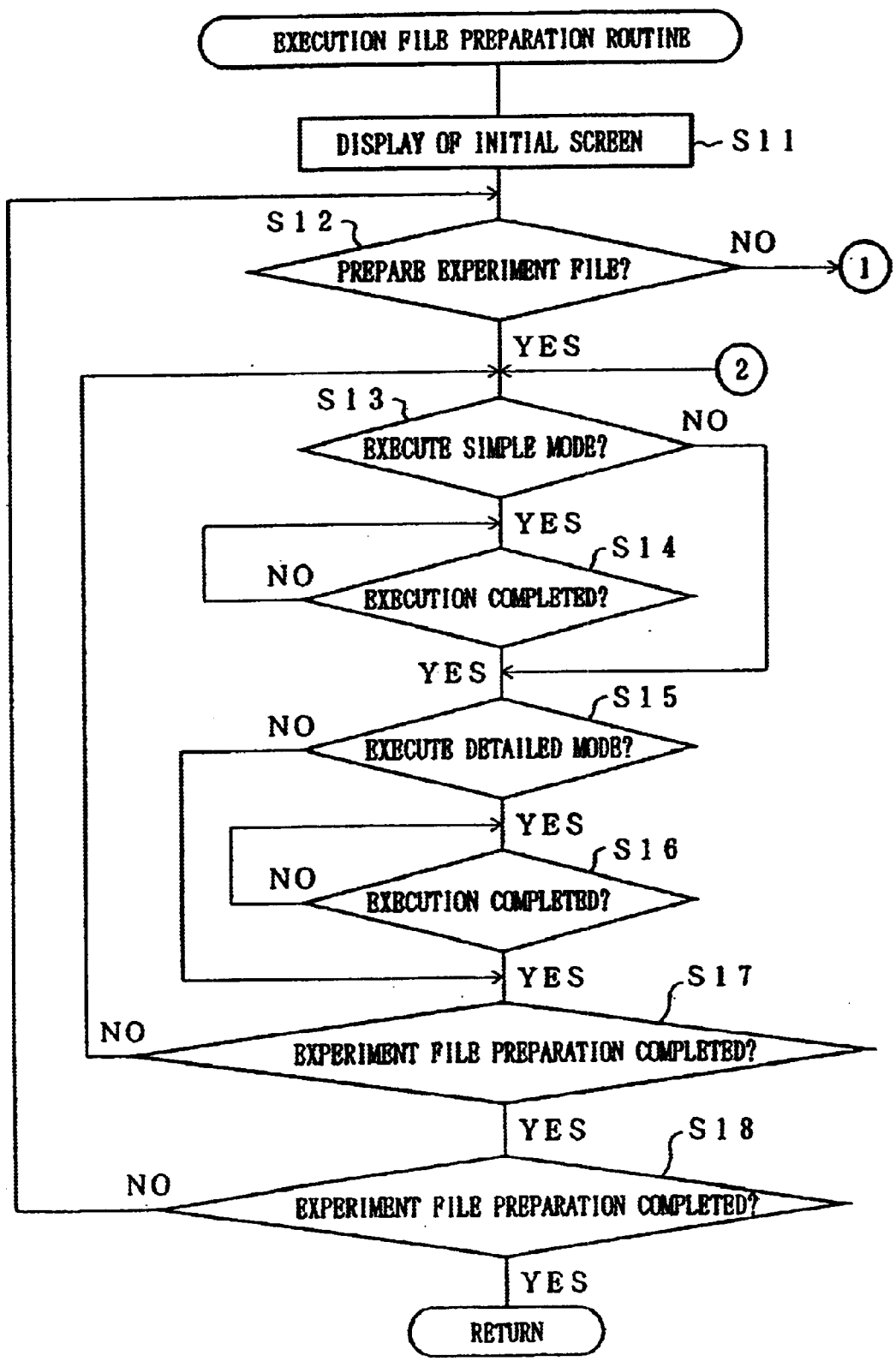
FIG. 26 is a flow chart showing the flow of execution file preparation in the flow chart shown in FIG. 25.

First, as shown in FIG. 26, GASYS.EXE is activated, and the execution file preparation section 123 displays on the monitor of the computer 9 the initial screen for input setup (S11). This initial screen displays three items: "Experiment file preparation," "Environment file preparation," and "Reagent/solvent name recording." Next, it is determined whether the item "Experiment file preparation" was selected from among the three items (S12). Here, if "Experiment file preparation" was not selected, operations proceed to S19, shown in FIG. 27. If, on the other hand, "Experiment file preparation" was selected, the initial screen displays the two items "Simple mode" and "Detailed mode." Next, it is determined whether "Simple mode" was selected (S13).

If it is determined that "Simple mode" was not selected in S13, operations proceed to S15, where it is determined whether "Detailed mode" was selected. Again, if it is determined that "Simple mode" was selected in S13, input of experiment conditions in the simple mode is performed.

Then, when execution of the simple mode is complete (S14), it is determined whether "Detailed mode" was selected. Here, if it is determined that "Detailed mode" was not selected, operations proceed to S17. If, on the other hand, it is determined that "Detailed mode" was selected, input of experiment conditions in the detailed mode is preformed.

Then, when execution of the detailed mode is complete (S16), it is determined whether experiment file preparation is complete (S17). Here, if it is not determined that experiment file preparation is complete, operations return to S13 in order to prepare another experiment file.

If, on the other hand, it is determined in S17 that experiment file preparation is complete, it is determined whether execution file preparation is complete (S18) Here, if it is determined that execution file preparation is complete, operations proceed to S2 shown in FIG. 25, and the sub-routine for execution job recording is performed. This sub-routine will be discussed later.

Again, if it is not determined in S18 that execution file preparation is complete, operations return to S12.

Figure 27:
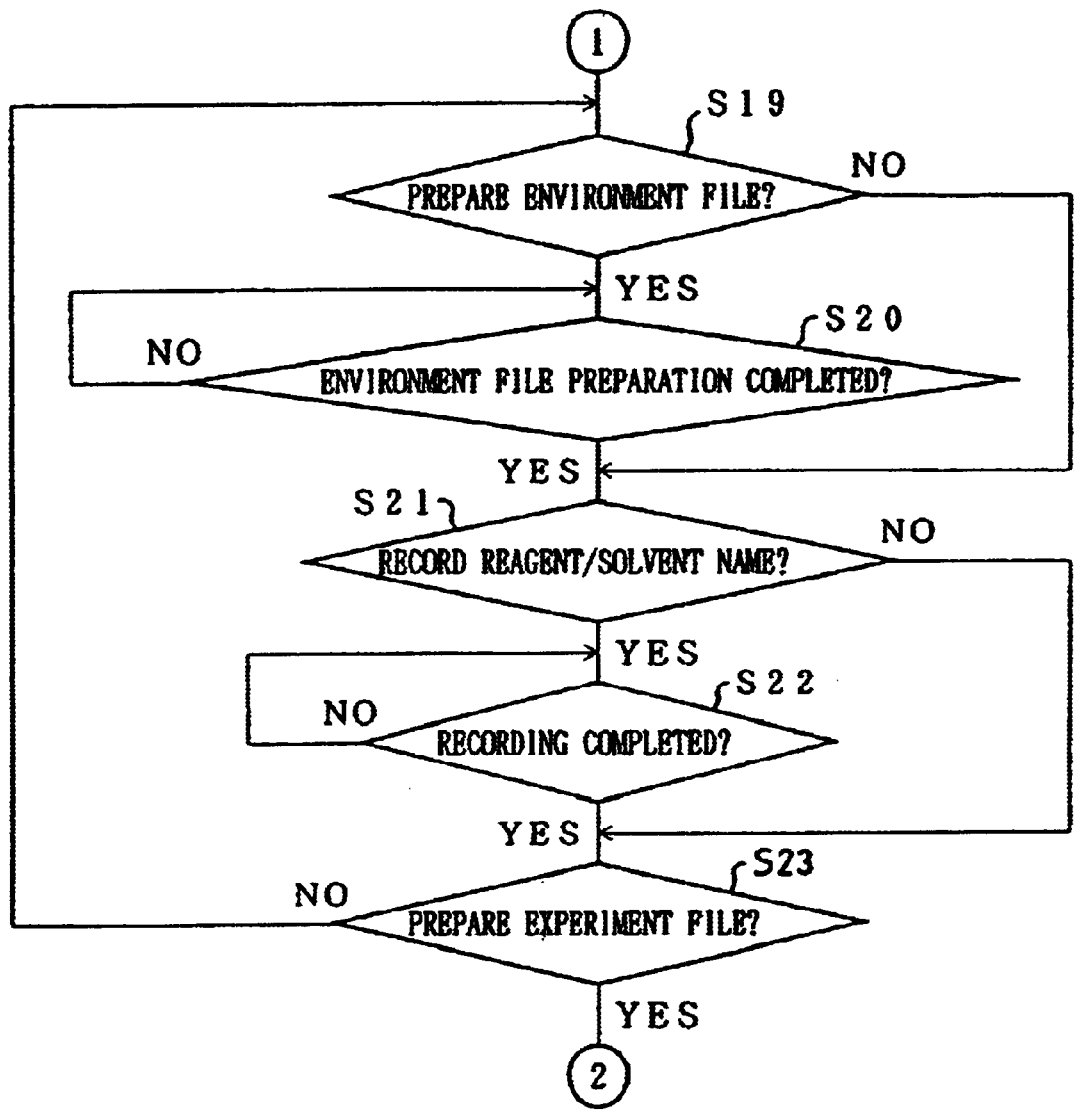
FIG. 27 is a flow chart showing the flow of execution file preparation in the flow chart shown in FIG. 25.

The following will explain, with reference to the flowchart in FIG. 27, the case in which experiment file preparation is not selected.

First, when the item "Experiment file preparation" is not selected from the initial screen, it is determined whether the item "Environment file preparation" was selected (S19). Here, if it is not determined that "Environment file preparation" was selected, operations proceed to S21. If, on the other hand, it is determined that "Environment file preparation" was selected, environment file preparation is performed. When environment file preparation is completed (S20), operations proceed to S21.

In S21, it is determined whether "Reagent/solvent name recording" was selected from the initial screen. Here, if it is not determined that "Reagent/solvent name recording" was selected, operations proceed to S23. If, on the other hand, it is determined in S21 that "Reagent/solvent name recording" was selected, recording of reagent and solvent names is performed. Then, when recording of reagent and solvent names is completed (S22), it is again determined whether experiment file preparation was selected (S23).

In S23, if it is not determined that experiment file preparation was selected, operations proceed to S19, where it is determined whether environment file preparation was selected. If, on the other hand, it is determined in S23 that experiment file preparation was selected, operations proceed to S13 in FIG. 26.

In this way, an execution file may be prepared for each synthesis experiment and set of experiment conditions.

Figure 28:
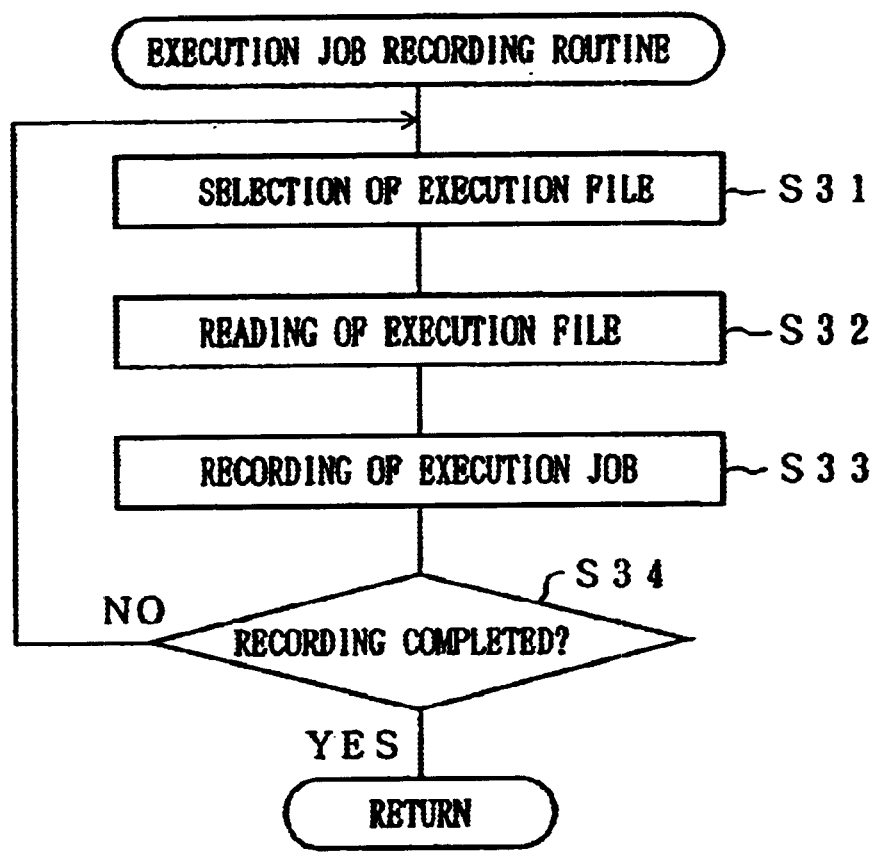
FIG. 28 is a flow chart showing the flow of execution job recording in the flow chart shown in FIG. 25.

The following will explain, with reference to FIG. 28, the sub-routine for execution job recording shown in FIG. 25.

First, one of the execution files prepared in the foregoing execution file preparation sub-routine is selected (S31).

Next, the execution file selected is read (S32). At this time, checking of the execution file read with regard to synthesis experiment automation system environment values and sequence parameters, confirmation of system devices to be used, confirmation of the arrangement of devices and implements to be used, etc. are performed. Then, if there are no irregularities in the execution file read, it is recorded as an execution job for actual execution of a synthesis experiment (S33)

Next, it is determined whether execution job recording is complete (S34). Here, if all of the execution files for the desired number of experiments have been recorded as execution jobs, execution job recording is terminated, and operations proceed to S3 shown in FIG. 25. If, on the other hand, execution files for the desired number of experiments have not all been recorded as execution jobs, operations return to S31.

In this way, an execution job may be recorded for each synthesis experiment and set of experiment conditions.

Figure 29:
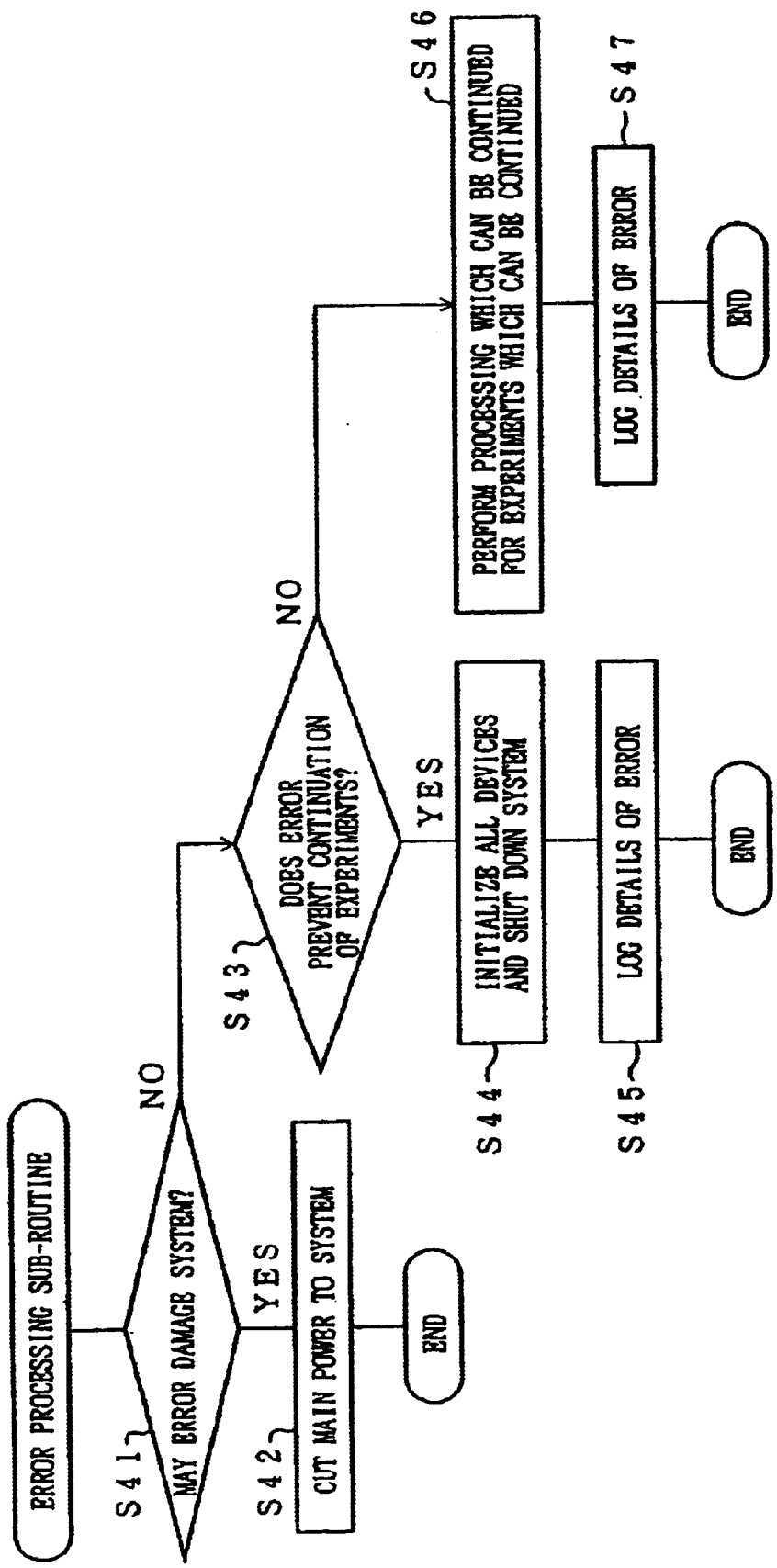
FIG. 29 is a flow chart showing the flow of error processing in the flow chart shown in FIG. 25.

The following will explain, with reference to FIG. 29, a sub-routine for the error processing mentioned above in connection with FIG. 25. In the present synthesis experiment automation system, when an error is detected, the type of the error is confirmed, and specific processing is performed according to the type of error.

First, it is determined whether the error is one which may damage the system, for example, one due to abnormal load, abnormal electric current, etc. (S41) Here, if the error is one which may damage the system, main power to the system is cut by, for example, throwing a breaker (S42). Then error processing is terminated.

In S41, if the error is not one which may damage the system, it is determined whether the error is one which prevents continuation of the experiment, for example, one due to a breakdown such as a traveling error of the robot 8 (S43). Here, if the error is one which prevents continuation of the experiment, all of the system devices are initialized, and the synthesis experiment automation system is shut down (S44). Then, after logging the details of the error detected (S45), error processing is terminated.

In S43, if the error is not one which prevents continuation of the experiment, processing which can be continued for experiments which can be continued is performed (S46). Then, after logging the details of the error detected (S47), error processing is terminated.

After performing the foregoing error processing, the details of the error are checked, and on the basis thereof, the synthesis experiment automation system is re-checked, and the next experiment prepared for.

In the synthesis experiment automation system according to the present invention, the devices of the reaction system are always in communication with the computer 9 while synthesis reactions are being performed, and accordingly any unforeseen circumstances, such as occurrence of an error, can be resolved by executing the error processing program (FIG. 29) as explained above. Moreover, as discussed above, in the present synthesis experiment automation system, irregularities are checked for at the execution file preparation and execution job recording stages, and thus these irregularities can be resolved. Accordingly, the present invention can provide a synthesis experiment automation system which is capable of safe and certain experiments.

In addition, with a synthesis experiment automation system with the foregoing structure, since the computer 9 controls the actions of the devices of the reaction system for each set of experiment conditions, each of the temperature regulator units 30 of the reaction device 3 can be operated under different experiment conditions.

For example, the temperature regulator units 30 are provided with temperature regulating means which can be set to different temperatures, and the computer 9 controls the temperature regulating operations of each temperature regulating means according to each set of experiment conditions. Consequently, the present synthesis experiment automation system is capable of performing simultaneous synthesis reactions under a plurality of different temperature conditions. Further, since each temperature regulator unit 30 can hold a plurality of synthesis reaction containers 15, simultaneous reactions can be performed under an even greater number of different experiment conditions.

In addition, since the transporting and placing actions of the robot 8 are also controlled by the computer 9, the robot 8 transports the robot 8 among the devices of the reaction system in accordance with each set of experiment conditions. Consequently, since the devices of the reaction system may be placed within the range of action of the robot 8, the extendibility of the synthesis experiment automation system can be improved.

Further, since the transporting and placing actions of the robot 8 and the actions of the devices in the reaction system are controlled for each set of synthesis reaction experiment conditions, the steps of the reaction process can be freely rearranged. Consequently, the flexibility of the system as a whole can be improved.

In order to perform a plurality of experiments simultaneously, it is sufficient, for example, for the computer 9 to set synthesis reaction steps in the reaction system for each experiment.

Further, the robot 8 used in the synthesis experiment automation system according to the present invention travels along a robot traveling rail 110 which is extendable. Consequently, by positioning the devices of the reaction system along the robot traveling rail 110, efficient transport of the reaction containers can be performed by the robot 8. Moreover, since the robot traveling rail 110 is extendable, the system can be easily extended by extending the robot traveling rail 110.

Incidentally, in the present embodiment, the devices positioned in the synthesis experiment automation system, i.e., the devices making up the reaction system, are the reaction container rack 1, the dispensing and separation device 2, the reaction device 3, the shaking device 4, the pre-analysis processing device 5, the gas chromatograph 6, and the liquid chromatograph 7, but a condensing device 150 may also be included in the reaction system, as shown in FIG. 1. Further, by extending the robot traveling rail 110, other devices may also be included in the reaction system.

The foregoing explanation merely discusses one example of the present invention, which may be embodied in any synthesis experiment automation system capable of reflecting the technical thought set forth in the claims appended hereto.

The following will explain a separation processing device which is an alternate device to the dispensing and separation device 2 used in the synthesis experiment automation system with the foregoing structure. The separation processing device described below is suitable for use in the synthesis experiment automation system, but may also be used alone.

Figure 30:
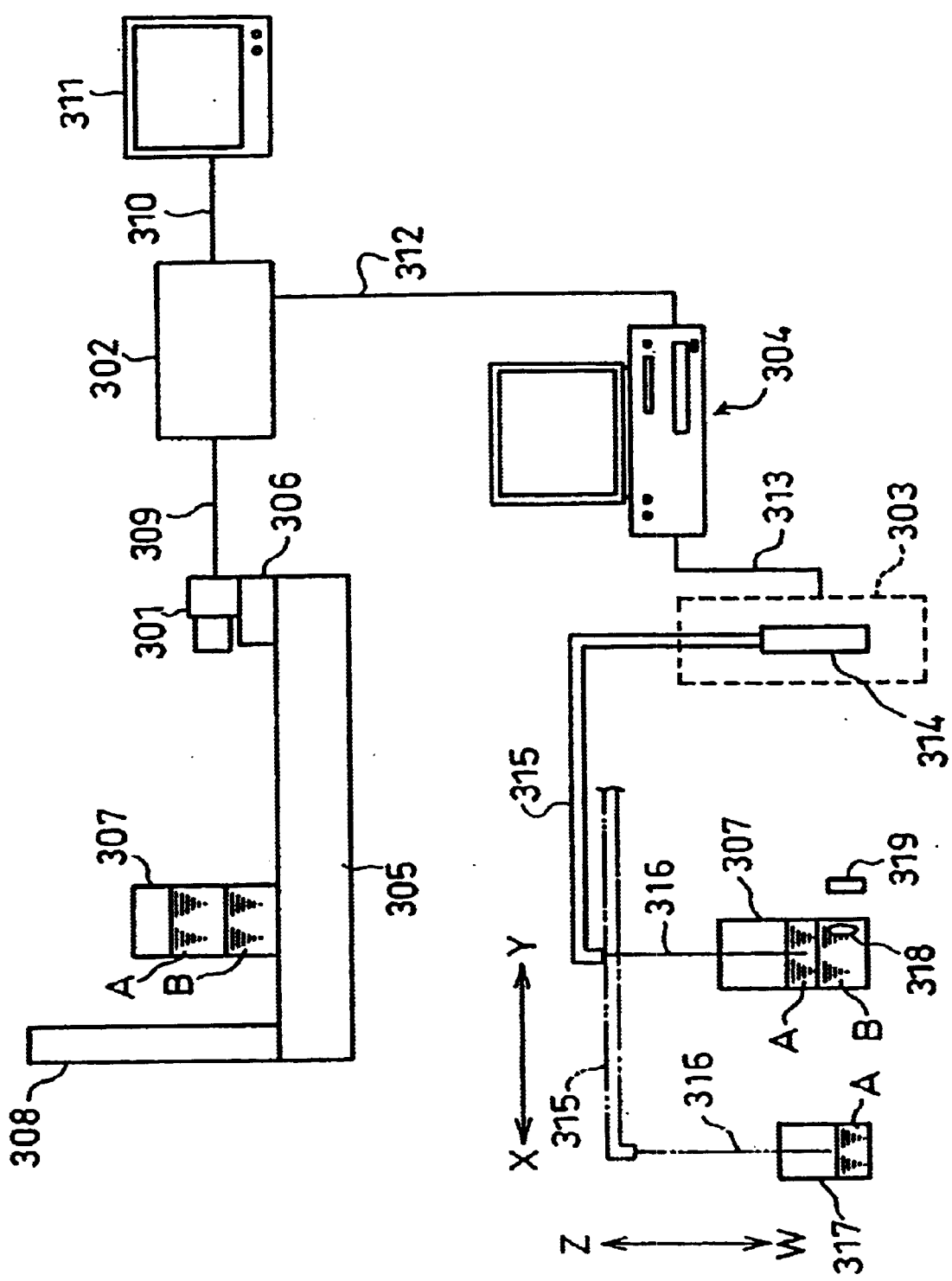
FIG. 30 is a schematic structural drawing of a system which uses a separation processing device according to the present invention.

As shown in FIG. 30, the separation processing device is made up of a CCD (charge coupled device) camera 301 as a reading means, a sensor main body 302, a liquid extracting device 303 as a solution extraction means, and a computer 304. Within the separation processing device, the devices other than the liquid extracting device 303, i.e., the CCD camera 301, the sensor main body 302, and the computer 304, make up a liquid level/interface position detecting device.

The CCD camera 301 is provided on a jack 306 on one end of a testing stand 305, which is positioned in the synthesis experiment automation system. In other words, by means of the jack 306, the CCD camera 301 can be moved vertically, i.e., up and down, on the testing stand 305. Consequently, the CCD camera 301 can accurately read an observed object from a suitable position.

At the other end of the testing stand 305 and perpendicular thereto is provided a fluorescent plate 308. A sample bottle 307 is placed on the testing stand 305 between the CCD camera 301 and the fluorescent plate 308. In other words, the CCD camera 301 reads as the observed object an image of the sample bottle 307, back-lit by the fluorescent plate 308.

The sample bottle 307 is a 100 cc sample tube, and holds a solution phase made up of two incompatible solutions A and B, which have separated into layers. In other words, the sample bottle 307 holds a solution A and a solution B, which have separated into two layers. The sample bottle 307 is roughly cylindrical, so as to make it easily transportable by the robot 8 (FIG. 1).

Figure 31:
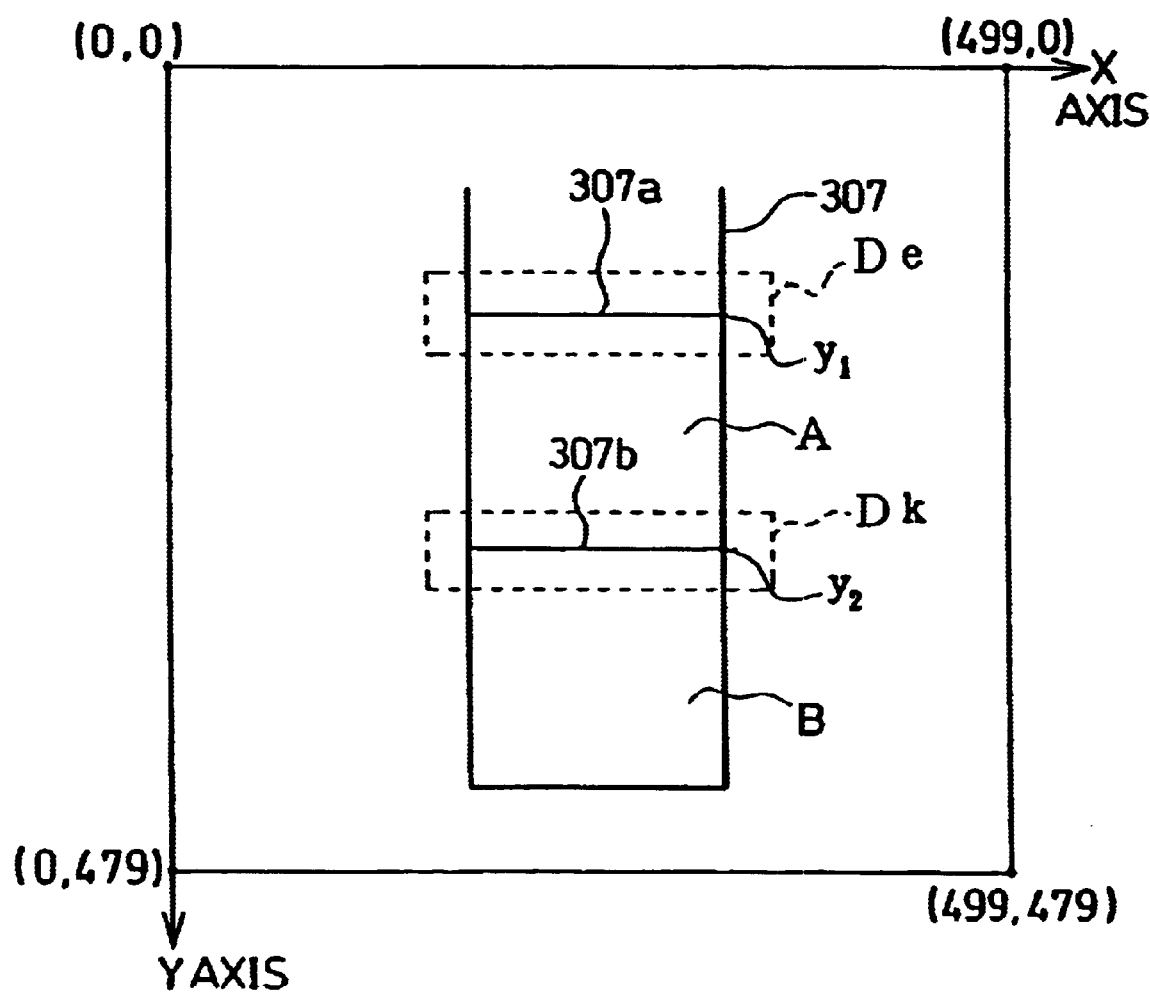
FIG. 31 is an explanatory drawing showing a pixel arrangement of an image of a sample bottle shown on a monitor provided in the system shown in FIG. 30.

The number of pixels of the CCD camera 307 is, for example, 240,000, with, as shown in FIG. 31, 500 pixels in the X axis direction, and 480 pixels in the Y axis direction. In reading the sample bottle 307, coordinates are used to express a liquid level 307a of the solution A on the upper level and an interface 307b formed between the solution A on the upper level and the solution B on the lower level. Here, the sample bottle 307 is a cylinder, and the area of the bottom is a constant. The coordinates of the liquid level 307a and the interface 307b are used to show the coordinate positions of the liquid level 307a and the interface 307b in terms of height only. Consequently, if the coordinates of the liquid level 307a and the interface 307b are known, the volumes of the solutions A and B can easily be calculated. Incidentally, the Y coordinate of the liquid level 307a is y1, and that of the interface 307b is y2.

As shown in FIG. 30, the CCD camera 301 is connected to the sensor main body 302 via a camera cord 309, and is provided so as to relay a read image to the sensor main body 302. The details of the sensor main body 302 will be discussed later.

The sensor main body 302 is connected to a monitor 311 via a monitor cable 310. The monitor 311 displays the image read by the CCD camera 301 in real time.

For the monitor 311, a 9-inch black and white monitor (KEYENCE Co. product, model OP-26171) is used, which displays in black and white the image read by the CCD camera 301.

The sensor main body 302 is connected to the computer 304 via a first RS-232C cable 312, through which is sent data read by the CCD camera 301. The details of the computer 304 will be discussed later. However, when the present separation processing device is included in the synthesis experiment automation system shown in FIG. 1, the computer 304 replaces the computer 9.

The computer 304 is connected to the liquid extracting device 303 via a second RS-232C cable 313, through which is sent data which has undergone predetermined processing.

The liquid extracting device 303 is provided with a syringe pump 314, a stepping motor (not shown), which raises and lowers a needle 316 (to be discussed below), and a driving motor (not shown), which moves the needle 316 forward and back. Driving control of the syringe pump and the motors is performed on the basis of data from the computer 304.

The syringe pump 314 is connected via a needle supporting body 315 to a needle 316, through which the syringe pump 314 extracts a solution from a sample bottle 307 into which the needle 316 is inserted. Then, through the needle supporting body 315, the needle 316 is moved in the X-Y direction, i.e., forward and back, by the driving motor, and is moved in the Z-W direction, i.e., up and down, by the stepping motor. The needle 316 is driven on the basis of data from the computer 304. The operations of the needle 316 will be discussed later.

Here, a case is shown in which, of the solutions A and B in the sample bottle 307, solution A is first extracted. The needle 316 extracts from the sample bottle 307 the solution A, and moves to a sample tube 317 of 30 cc capacity, into which the solution A is discharged. When the solution B is to be extracted, the needle 316 is lowered to the bottom of the sample bottle 307. In this case, a magnetic stirrer 318 used in stirring during the synthesis reaction is moved to the side of the sample bottle 307 and held there by a magnet 319 provided at the side of the sample bottle 307, so that the magnetic stirrer 318 will not be in the way of the needle 316.

Next, the sensor main body 302 and the computer 304 will be explained.

Figure 32:
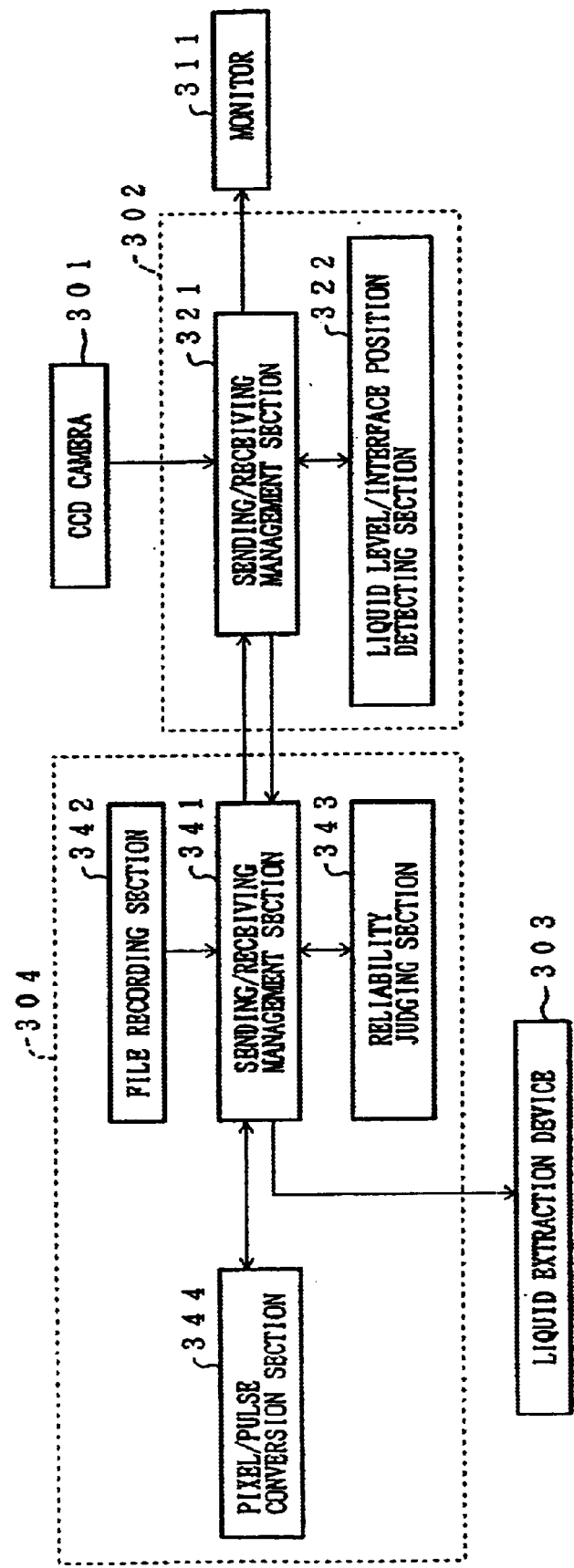
FIG. 32 is a schematic structural block diagram of the system shown in FIG. 30.

As shown in FIG. 32, the sensor main body 302 is made up of a sending/receiving management section 321 and a liquid level/interface position detecting section 322. Further, the computer 304 is made up of a sending/receiving management section 341, a file recording section 342, a reliability judging section 343, and a pixel/pulse conversion section 344.

The sensor main body 302 and the computer 304 collectively make up position detecting means for detecting a liquid level of a solution phase made up of two incompatible solutions which have separated into layers, and an interface between the two solutions.

To explain the sensor main body 302, the sending/receiving management section 321 receives image data from the CCD camera 301, and sends that image data to both the monitor 311 and the liquid level/interface position detecting section 322.

Further, the sending/receiving management section 321 receives from the computer 304 separation image files (image patterns), and sends these to the liquid level/interface position detecting section 322, and also sends data received from the liquid level/interface position detecting section 322 to the sending/receiving management section 341 of the computer 304. Here, the data sent to the sending/receiving management section 341 is data expressing the liquid level and interface coordinates in terms of pixels.

Based on image data read by the CCD camera 301 and on the separation image files, both provided by the sending/receiving management section 321, the liquid level/interface position detecting section 322 calculates the coordinates of the positions of a liquid level and an interface in the image of the sample bottle 307 observed by the CCD camera 301, and then sends the coordinates of the liquid level and interface positions to the sending/receiving management section 321. The details of the liquid level/interface position detecting section 322 will be discussed later.

Next, to explain the computer 304, the sending/receiving management section 341 reads separation image files recorded in the file recording section 342, and sends these separation image files to the sending/receiving management section 321 of the sensor main body 302, along with a signal requesting liquid level and interface coordinates. In detecting the liquid level and interface coordinates of image data of the sample bottle 307, the sending/receiving management section 341 requests liquid level and interface coordinates a plurality of times. The number of such requests can be set as desired.

Then, the sending/receiving management section 341 sends the liquid level and interface coordinates received from the sending/receiving management section 321 of the sensor main body 302 to the reliability judging section 343.

The reliability judging section 343 judges the reliability of the liquid level and interface coordinates sent from the sensor main body 302 to the sending/receiving management section 341, and sends a signal expressing that reliability to the sending/receiving management section 341. This reliability expresses the result of a judgment of whether the liquid level and interface coordinates detected by the sensor main body 302 are legitimate values for the actual sample bottle 307.

Since the sending/receiving management section 341 requests liquid level and interface coordinates a plurality of times for the solutions in a single sample bottle 307, liquid level and interface coordinate data obtained in response to each such request are sent to the reliability judging section 343.

Then, if the liquid level and interface coordinates for a single sample bottle 307 fall within a predetermined range for a predetermined number of times, the reliability judging section 343 judges that data to be reliable, and outputs a signal to that effect. The range and the number of times can be set as desired.

Accordingly, if the signal from the reliability judging section 343 indicates that the data is reliable, the sending/receiving management section 341 sends to the pixel/pulse conversion section 344 data corresponding to a pixel number (pixel data) corresponding to the liquid level and interface coordinates received from the sending/receiving management section 321.

The pixel/pulse conversion section 344 converts the pixel data into a number of pulses for the stepping motor for raising and lowering the needle 316, and sends data corresponding to this number of pulses (pulse data) to the sending/receiving management section 341.

Then the sending/receiving management section 341 sends the pulse data received from the pixel/pulse conversion section 344 to the liquid extracting device 303.

The following will explain liquid level/interface position detection processing in concrete terms.

First, the file recording section 342 will be explained.

In the file recording section 342 are recorded a plurality of images like that shown in FIG. 31, of domains in the vicinity of a liquid level 307a of a sample bottle 307 (liquid level domain De) and domains in the vicinity of an interface 307b (interface domain Dk). In other words, images of domains in the vicinity of a liquid level and images of domains in the vicinity of an interface are recorded in the file recording section 342.

The data concerning the liquid level domains De and the interface domains Dk also includes information such as liquid level coordinates y1 and interface coordinates y2 for two solutions in a sample bottle the same size as the sample bottle 307, the total quantity of the solution phase and the proportions of the solutions when separated, the color of each solution, etc.

Approximately 160 separation image files are stored in the file recording section 342, and these are sent one by one to the sensor main body 302 via the sending/receiving management section 341.

It is sufficient if the number of separation image files recorded in the file recording section 342 is at least two, i.e., one set each of data on the liquid level domain De and data on the interface domain Dk. It is not preferable to record too many separation image files, because this increases the time required in liquid level/interface position detection processing. For this reason, the number of separation image files recorded in the file recording section 342 may be set as appropriate in view of the relationship among the number of types of synthesis reaction (i.e., the number of types of solutions to be separated), the time available for processing, etc.

Next, the liquid level/interface position detecting section 322 will be explained in detail. The liquid level/interface position detecting section 322 detects liquid level coordinates and interface coordinates by means of separate separation image files, but in what follows, for the sake of convenience, explanations which apply to both liquid level coordinates and interface coordinates will not specify one or the other, but refer to them collectively as "sample coordinate values."

The liquid level/interface position detecting section 322 detects the sample coordinate values of the solutions actually stored in the sample bottle 307 using as a standard the separation image files recorded in the file recording section 342. In other words, the sensor main body 302 searches for the sample coordinate values based on the separation image files.

At this time, if the separation image file is close to the sample coordinate values, i.e., within the predetermined range of a previously set liquid level domain or interface domain, the sample coordinate values are correctly calculated based on the coordinate value y1 or y2 included in the separation image file.

In contrast, if the separation image file is far from the sample coordinate values, i.e., outside the predetermined range of a previously set liquid level domain or interface domain, a meaningless value is calculated.

Then the liquid level/interface position detecting section 322 sends the value detected to the computer 304 through the sending/receiving management section 321.

The foregoing actions are repeated a plurality of times for a single sample bottle 307, and the detected data is sent to the computer 304 each time.

Figure 33:
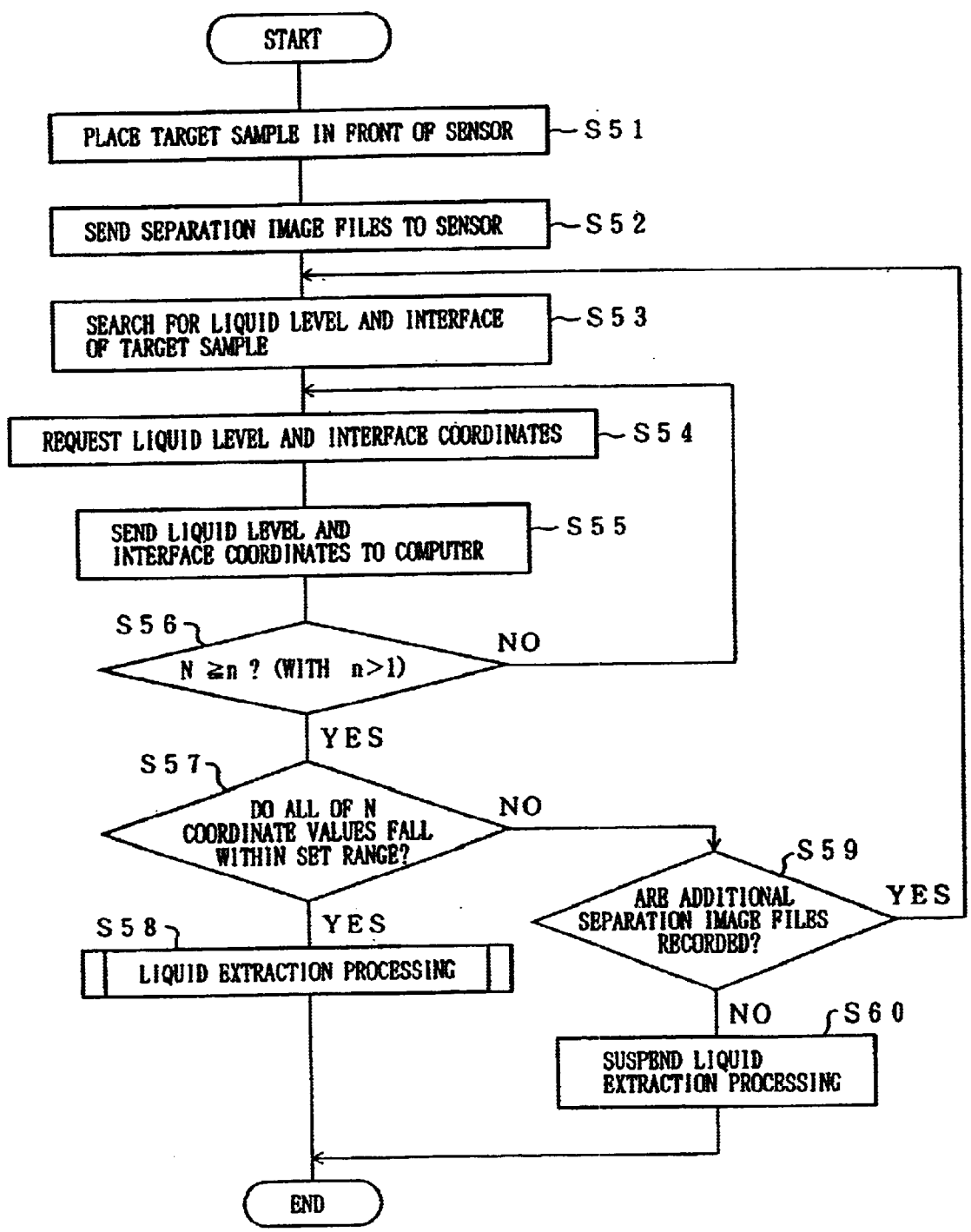
FIG. 33 is a flow chart showing the flow of separation processing carried out by the separation processing device shown in FIG. 30.
Figure 34:
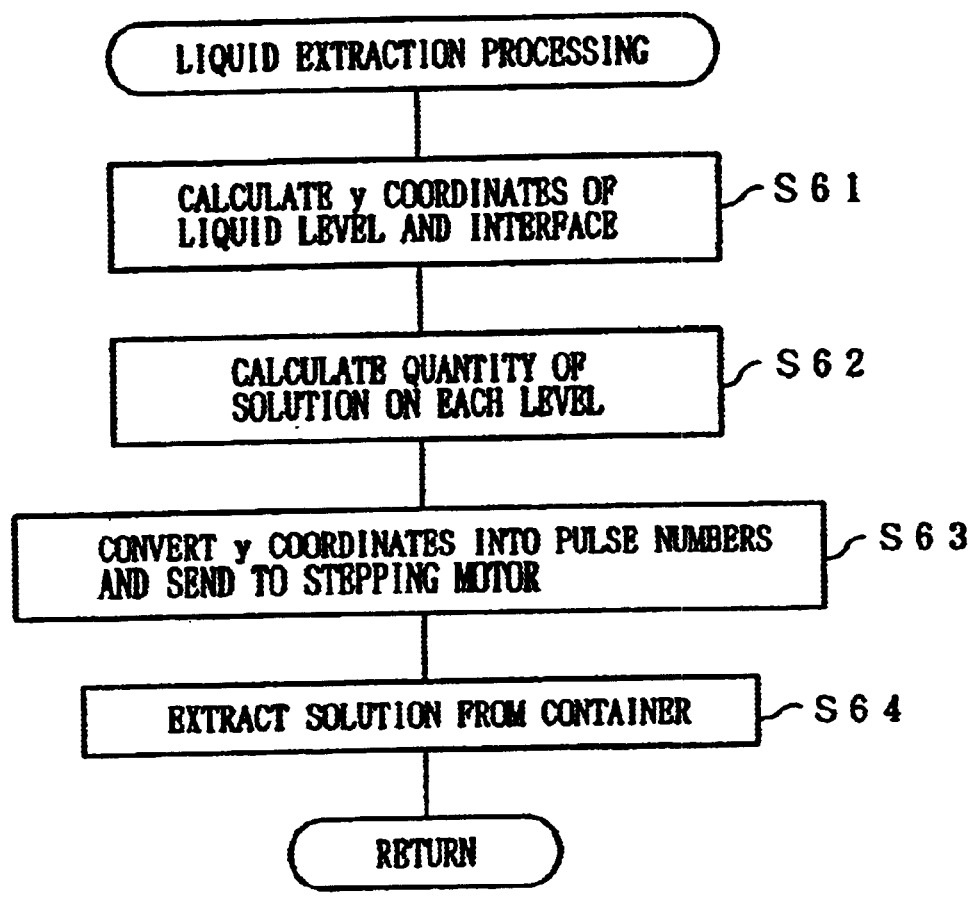
FIG. 34 is a flow chart showing a liquid extraction processing subroutine of the separation processing shown in FIG. 33.

Next, the flow of separation processing in a separation processing device with the foregoing structure will be explained with reference to FIGS. 30, 33, and 34.

First, liquid level/interface position detection processing will be explained with reference to the flow-chart in FIG. 34. Here, the sample bottle 307 holding the solution phase made up of two incompatible solutions which have separated into layers, which is read by the CCD camera 301, will be referred to as the "target sample."

First, a robot (not shown) places the target sample in front of the sensor main body 302 (S51).

Next, the computer 304 sends to the sensor main body 302 previously recorded separation image files. (S52).

Then the sensor main body 302 searches for the liquid level and interface of the target sample (S53). In other words, the sensor main body 302 searches for the pattern of the target sample using the separation image files as a standard.

Next, the computer 304 requests the coordinates of the liquid level and the interface of the target sample (S54). Here, this request for liquid level and interface coordinates is performed N times (N>1).

Then, the sensor main body 302 sends the liquid level and interface coordinates to the computer 304 (S55). In other words, in response to each request from the computer 304 in S55, the sensor main body 302 sends the positions of the liquid level and the interface of the target sample to the computer 304 as data, shown as coordinate values on the monitor 311 connected to the sensor main body 302. At this time, the number of replies from the sensor main body 302 to the computer 304 is N times, or the number of requests from the computer 304 to the sensor main body 302.

Next, the computer 304 determines whether the number n (n>1) of liquid level/interface coordinate replies from the sensor main body 302 is equal to a predetermined number of times, i.e., N (N>1) times (S56). Here, if n has not yet reached N, operations return to S54.

In S56, if n has reached N, the computer 304 determines whether the N coordinate values all fall within a previously set range (S57).

If all of the N coordinate values are within the previously set range in S57, repeatability is good, and the coordinate values received by the computer 304 are judged reliable. Then, liquid extraction processing is performed on the basis of the coordinate values (S58). Here, the coordinate values are the values obtained as a result of searching by the liquid level/interface position detecting section 322 of the sensor main body 302 using the separation image files received from the computer 304 as a standard. Liquid extraction processing will be discussed later.

If, in S57, not all of the N coordinate values fall within the previously set range, repeatability is judged to be poor. In other words, it is judged that the separation image files are not appropriate to the target file.

As a result, the computer 304 then determines whether there are additional separation image files recorded (S59). Here, if it is determined that there are additional separation image files recorded, operations return to S53, and the liquid level and interface of the target sample are searched for using the additional separation image files.

Again, if it is determined in S59 that there are no additional separation image files recorded, liquid extraction is suspended (S60). In other words, if all of the recorded separation image files yield values without repeatability, the liquid level and interface are judged to be unclear, and the computer 304 directs the liquid extraction device 303 to suspend operations, so that liquid extraction actions will not be performed.

Next, the flow of liquid extraction processing will be explained, with reference to the flow-chart shown in FIG. 34.

First, using the repeatable coordinate values obtained in S57 (on the flow-chart shown in FIG. 33), the y coordinates of the liquid level and the interface of the target sample are calculated (S61). In other words, the computer 304 judges that the greater of the coordinate values is the y coordinate of the liquid level (y1), and the smaller the y coordinate of the interface (y2).

Next, the quantity of the solution on each level is calculated from the liquid level coordinate y1 and the interface coordinate y2 (S62).

Then, each of the foregoing Y coordinates is converted into a pulse number, which is sent to the stepping motor which raises and lowers the needle 316 (S63).

Then the liquid extracting device 303 extracts a solution from the container (sample bottle 307) (S64). In other words, the stepping motor of the liquid extracting device 303 drives the needle 316 so as to extract either the upper- or lower-level solution from the sample bottle 307 and discharge it into another container.

Using the foregoing image processing, the positions of the liquid level and the interface (especially the interface) of the solution phase are detected primarily by using the separation image target to search for a difference in color between the two solutions. However, if, for example, there is almost no difference in color between the two solutions, it may be impossible to correctly detect the interface.

In such cases, an alternate method, which uses differences in refractive index to detect the interface of the solution phase, may be used. In this method, as shown in FIG. 35, a colored tape 351 having a uniform width is provided on the fluorescent plate 308 in a direction perpendicular to the liquid level 307a and the interface 307b, and the liquid level 307a and the interface 307b are confirmed by means of differences in refractive index when the colored tape 351 is viewed through the sample bottle 307.

Figure 35:
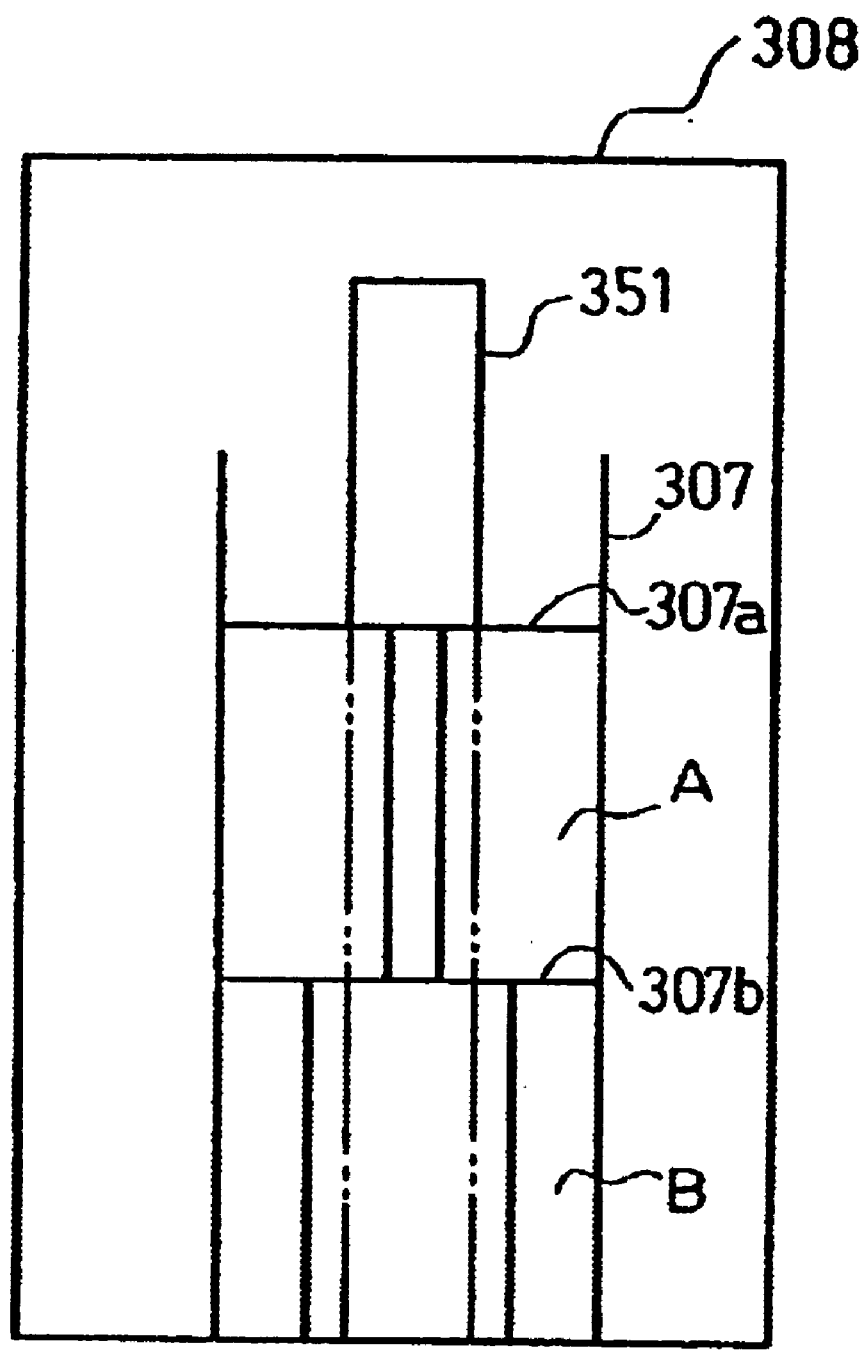
FIG. 35 is an explanatory diagram showing, in the separation processing device shown in FIG. 30, detection of a liquid level and an interface of a solution phase by means of differences in the refractive index of each solution.

In FIG. 35, since the refractive index of the solution A in the sample bottle 307 is smaller than that of air, the width of the colored tape 351 when viewed through the solution A is less than the actual width. In contrast, since the refractive index of the solution B in the sample bottle 307 is greater than that of air, the width of the colored tape 351 when viewed through the solution B is greater than the actual width.

It can be seen that, if the liquid level and interface are detected in this way, using the differences in refractive indices of the solutions in the solution phase, the liquid level and the interface can be effectively detected in cases when there is almost no difference in color between the two solutions in the solution phase.

It is satisfactory if the color of the colored tape 351 is different from the colors of the solutions in the sample bottle 7, and is not limited to any particular color. Again, the colored tape 351 need not be provided perpendicular to the liquid level 307a and the interface 307b of the solution phase in the sample bottle 307; it is satisfactory if the colored tape 351 is provided so as to cross the liquid level 307a and the interface 307b at an angle at which the difference in refractive indices of the respective solutions is evident.

In this way, since the liquid level 307a and the interface 307b of the sample bottle 307 can be detected automatically from the image of the solution phase read by the CCD camera 301, a separation processing device with the foregoing structure is suitable for use in a device for performing organic synthesis reactions automatically. Consequently, a device for performing organic synthesis reactions automatically can be fully automated.

Further, since the liquid level 307a and the interface 307b of the solution phase in the sample bottle 307 are found by approximating from among the separation image files recorded in the recording section 342, and then calculating from these approximate values, position detecting can be performed quickly and accurately.

In addition, since the liquid extracting device 303 of the separation processing device calculates the quantities of the upper- and lower-level solutions of the solution phase in the sample bottle 307 based on the detected liquid level 307a and interface 307b, and then extracts either of the two solutions, extraction of the solutions can be automated. As a result, the separation processing device is suitable for use in a synthesis experiment automation system.

In the foregoing separation processing device, the volumes of the solutions A and B in the sample bottle 307 are calculated from the liquid level 307a and interface 307b, and, based on these volumes, the driving amount of the needle 316 is calculated and the solutions are extracted. In this case, the shape and size of the sample bottles 307 must always be uniform.

As a method of performing separation using the separation processing device, the foregoing explained a method in which a solution is extracted after calculating the respective volumes of the solutions A and B in the sample bottle 307 using the liquid level 307a and the interface 307b. In addition to this method, another possible method is one in which a solution in the container is extracted using information regarding the heights of the liquid level 307a and the interface 307b from the bottom of the container.

In this method, driving of the needle 316 is controlled and the solution is extracted using information regarding the respective heights of the liquid level 307a and the interface 307b of the solution phase in the sample bottle 307. At this time, the coordinates of the liquid level 307a and the interface 307b are continuously detected, and these coordinates are sent to the liquid extracting device 303. Then, when the coordinates of the liquid level 307a reach a value within a predetermined range from the interface 307b, extraction of the upper-level solution A from the sample bottle 307 is discontinued.

In this way, using information regarding the respective heights of the liquid level 307a and the interface 307b of the solution phase in the sample bottle 307, the solutions A and B in the sample bottle 307 are separated.

With the foregoing method, the sample bottle 307 need not be limited to any particular shape, and the scope of application of the separation processing device according to the present invention can be broadened.

For the CCD camera 301 in the separation processing device with the foregoing structure, a KEYENCE Co., Ltd.

model CV-C1 was used, and for the sensor main body 302, a KEYENCE model CV-100 was used. In addition, the control program for the present separation processing device was prepared to run on the OS (operating system) Windows™ 95. Accordingly, it is satisfactory if the computer 304 is a computer on which Windows™ 95 can be operated. Incidentally, the present invention is not limited to the foregoing OS, another OS may be used. In this case, the program may be changed as necessary in order to run on the OS to be used.

The present invention is not limited to the various specific structures discussed in the present embodiment.

Next, the following will explain a reaction container which may be used instead of the reaction container used in the reaction device 3 of the synthesis experiment automation system shown in FIG. 1, i.e., instead of the reaction container made up of the synthesis reaction container 15 covered, via the seal cap 49, by the cylindrical member 54. The following reaction container is suitable for use in the foregoing synthesis experiment automation system, but may also be used alone.

Figure 36:
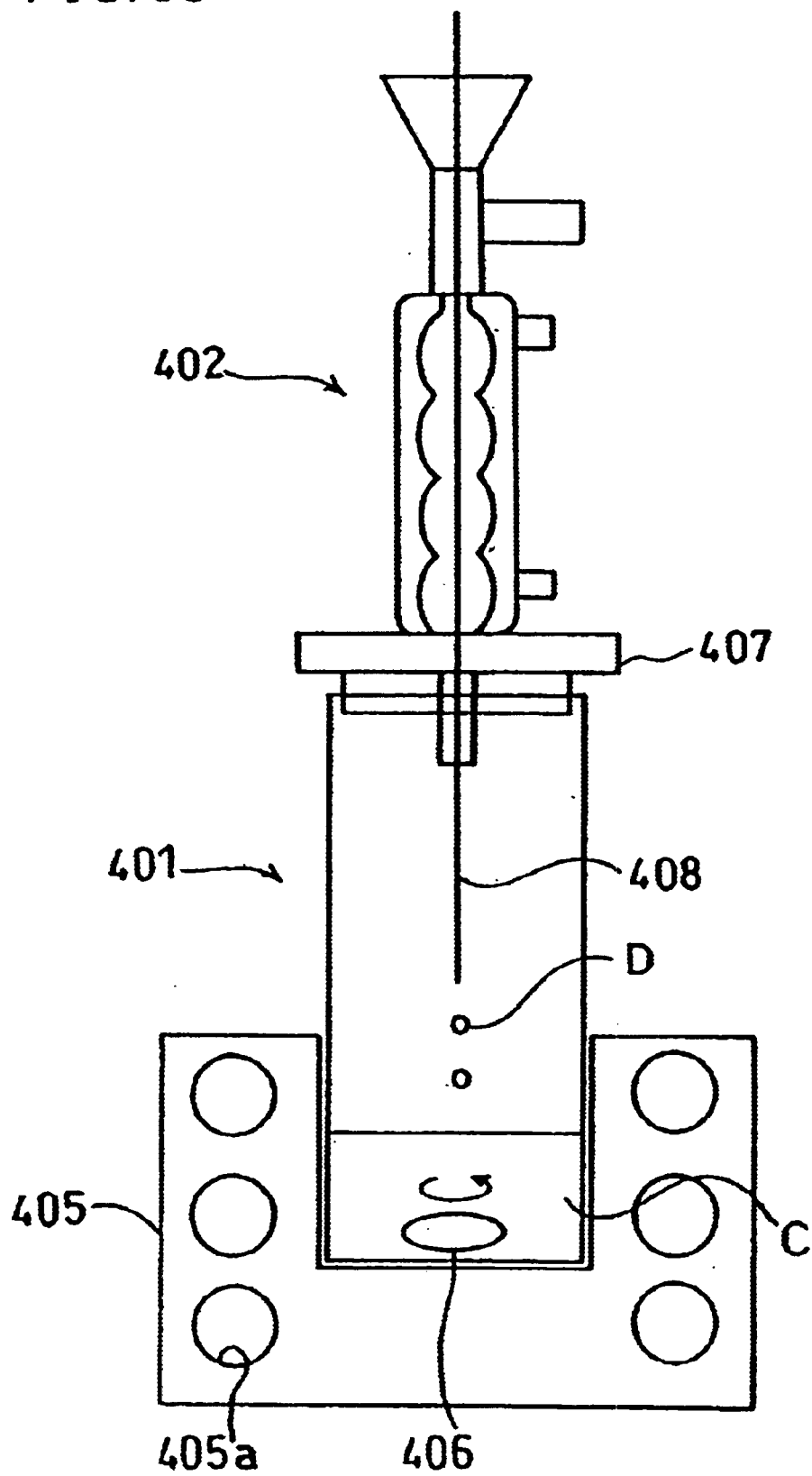
FIG. 36 is a side view showing the structure of a reaction container according to the present invention.

As shown in FIG. 36, the reaction container is made up of a container 401 (container section) and an introducing tube 402 provided on the upper part of the container 401.

The container 401 is, for example, a cylindrical glass tube of approximately 100 ml capacity.

Figure 37:
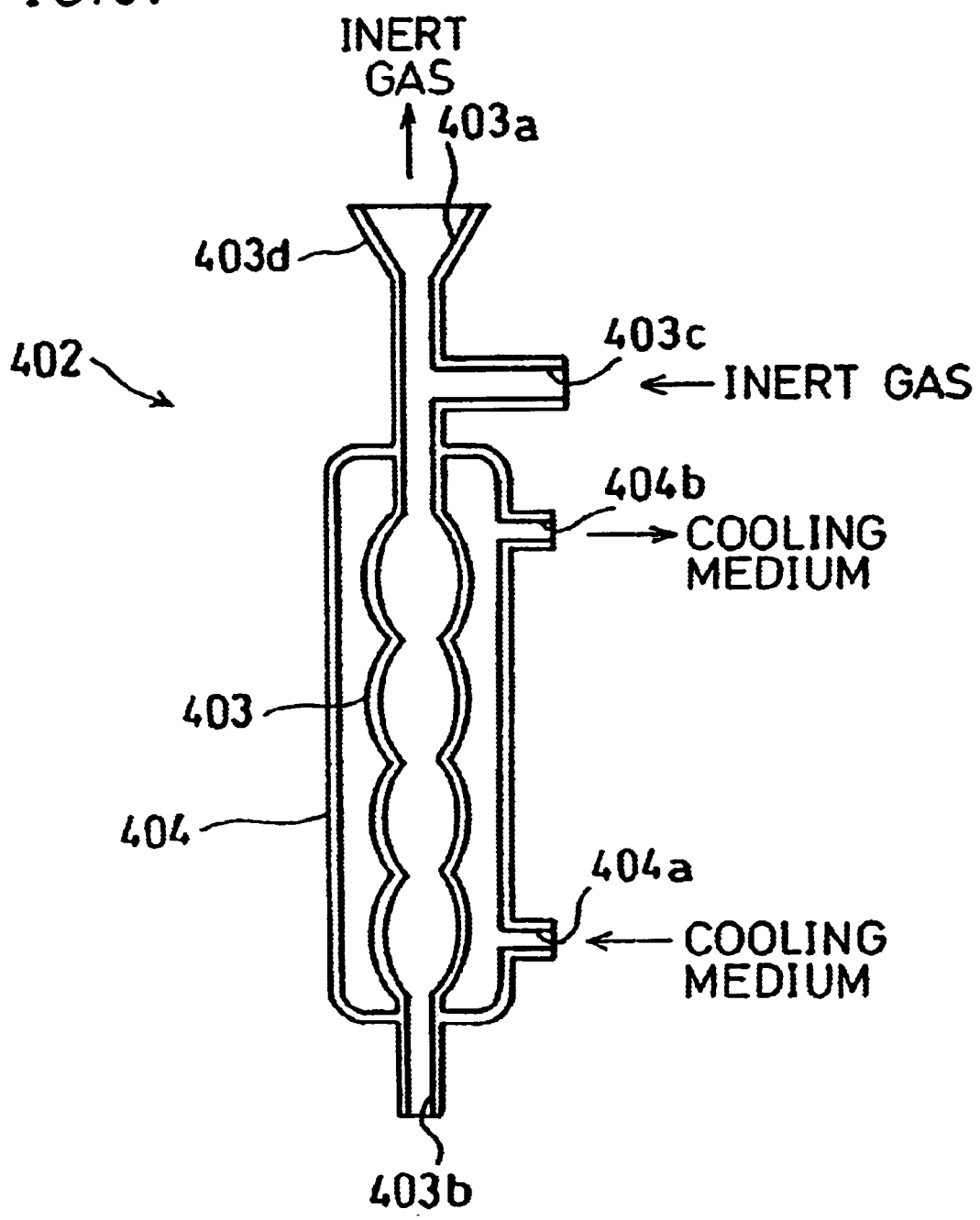
FIG. 37 is a cross-sectional view showing the structure of an introducing tube of the reaction container shown in FIG. 36.

The introducing tube 402, as shown in FIG. 37, has a double-walled structure of an inner tube 403 and an outer tube 404, the circulation of each of which is completely separate from that of the other. The inner tube 403 is provided with a reagent introduction opening 403a (upper opening) at its upper end, a reagent drip opening 403b (lower opening) at its lower end, and, in the tube wall near its upper end, a gas flow intake 403c. Further, the outer tube 404 is provided with a coolant intake 404a and a coolant outflow 404b, in the lower and upper parts of the tube wall, respectively.

In order to use the foregoing reaction container to conduct a reaction between a reagent C (first reagent) and a reagent D (second reagent), the reagent C is placed in the container 1 in advance, and the reagent D is introduced into the container 401 through the introducing tube 402 inserted into the top of the container 401. At this time, the reagent D is introduced through the reagent introduction opening 403a of the introducing tube 402, passes through the channel of the inner tube 403, and thence into the container 401 through the reagent drip opening 403b.

Incidentally, the terms "reagent C" and "reagent D" are used merely for convenience in explaining operations, and do not necessarily indicate single chemical compounds. In some cases, two or more compounds will be mixed together. Again, reagents C and D may each be mixed with a reaction solvent, or a reaction solvent may be placed in the container 401 in advance.

In this way, the reaction takes place by the mixing of the reagents C and D in the container 401. When the reaction is to be performed under heating, a heating device is provided to heat the container 401. Here, as shown in FIG. 36, an aluminum block thermostat 405 having the same structure as the aluminum block 36 shown in FIG. 7 is used for the heating device. The aluminum block thermostat 405 heats the container 401 by means of a heating section (not shown), and can also perform cooling by passing a coolant prepared by mixing ethylene glycol and water through holes 405a provided in the aluminum block thermostat 405. As a result, the aluminum block thermostat 405 can heat the container 401 at a constant temperature. However, the method of heating the container 401 is not limited to that outlined above.

When heat is applied in this way, or when the reaction produces heat, reaction materials, reaction products, reaction solvents, etc. which are vaporized by the heat in the container 401 attempt to escape into the atmosphere through the inner tube 403 of the introducing tube 402. In order to prevent this, a coolant is supplied through the coolant intake 404a in the lower part of the wall of the outer tube 404, flows between the inner tube 403 and the wall of the outer tube 404, and is discharged through the coolant outflow 404b in the upper part of the wall of the outer tube 404, thus cooling the wall of the inner tube 403 and liquefying the vapor components in the inner tube 403 and returning them to the interior of the container 401.

Further, in this kind of reaction, in order to prevent the reaction system from coming into direct contact with the atmosphere, it is sometimes necessary to seal the reaction system by closing off from the atmosphere the upper end of the introducing tube 402, which is where the reaction system contacts the atmosphere. In order to seal the reaction system in this way, an inert gas is supplied through the gas flow intake 403c of the inner tube 403, and released into the atmosphere through the reagent introduction opening 403a. As a result, the upper part of the inner tube 403 is filled with the inert gas flowing through it, and the reaction system is sealed by isolation from the atmosphere by the inert gas. A representative example of an inert gas to be supplied through the gas flow intake 403c is nitrogen, and nitrogen is used in the present embodiment. However, as long as the gas is inert to the reaction, there is no need to be limited to this, and another inert gas, such as argon, helium, or carbon dioxide gas, may be used.

Generally, stirring is performed during the reaction. In the present embodiment, a magnetic stirrer 406 (see FIG. 36) is placed inside the container 401 in advance, and stirring of the inside of the container 401 is performed by rotation of the magnetic stirrer 406.

The foregoing reaction container is made up of the container 401 and the introducing tube 402. In the introducing tube 402, the inner tube 403, the reagent introduction opening 403a, and the reagent drip opening 403b make up a reagent introducing section. The inner tube 403, the outer tube 404, the coolant intake 404a, and the coolant outflow 404b make up a cooling section, and the inner tube 403, the gas flow intake 403c, and the reagent introduction opening 403c make up a seal section.

Since the reagent introducing section, the cooling section, and the seal section are combined together in the introducing tube 402, the reaction container for allowing reagents to react can be made more compact.

Further, with the foregoing reaction container, since the reagent introducing section, the cooling section, and the seal section are combined into a single member, assembly of the reaction container is not troublesome, as was the case in the past. This is a great advantage especially when using a device for performing reaction experiments automatically (the synthesis experiment automation system).

When using the foregoing reaction container in the synthesis experiment automation system described above, it is preferable if the reaction container is further provided with the following structure.

Figure 38A:
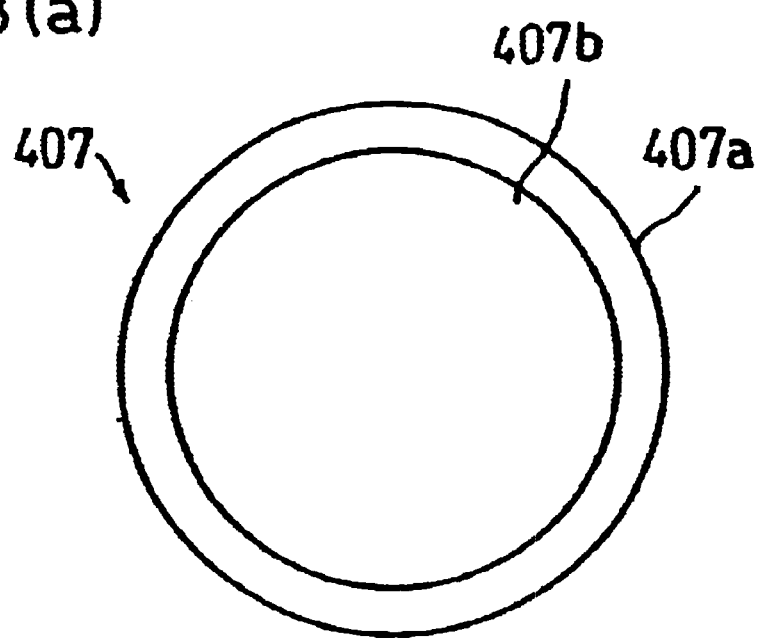
FIG. 38($a$) is a plan view of a lid of a container section of the reaction container shown in FIG. 36.
Figure 38B:
Figure 39:
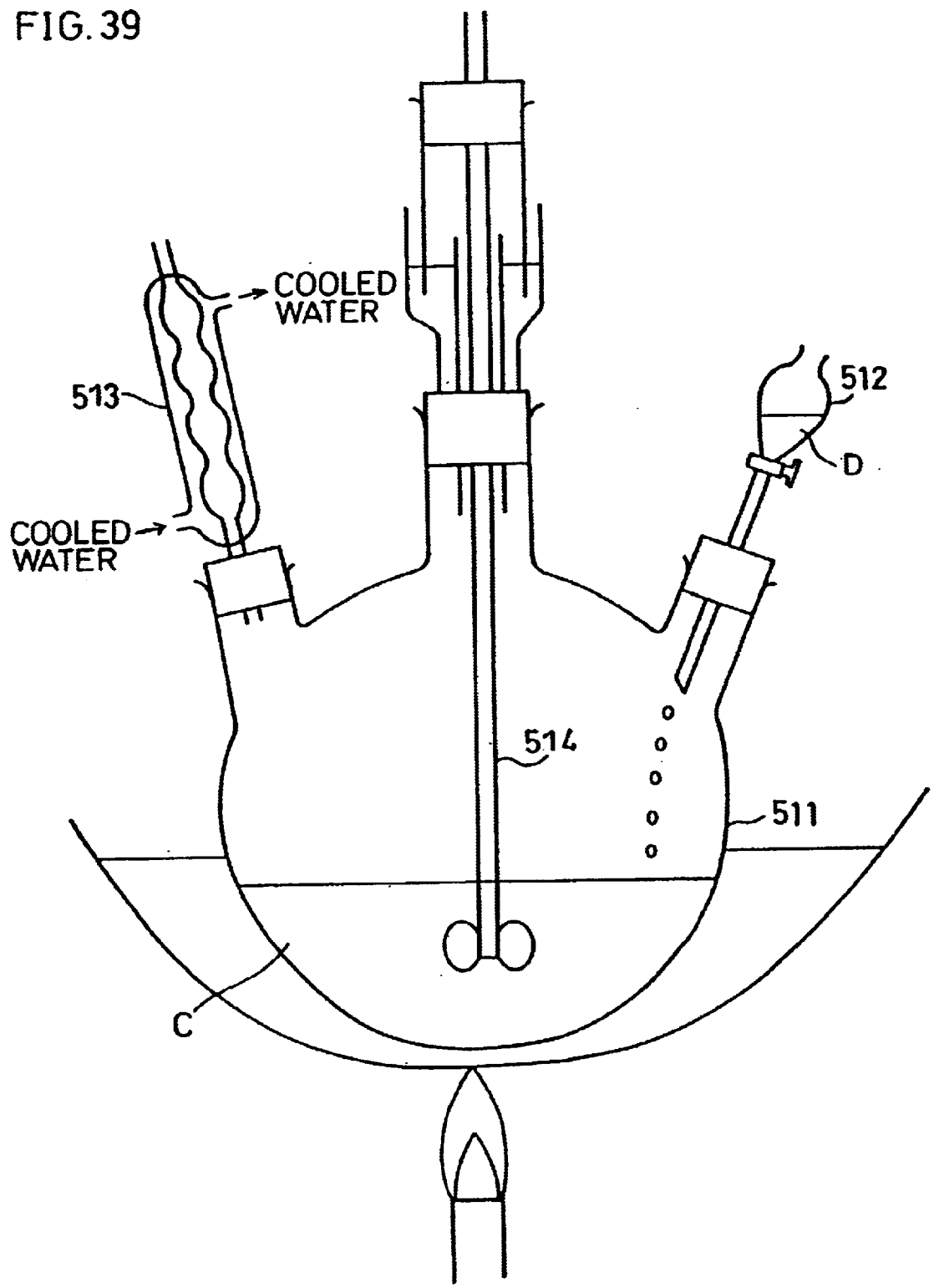
FIG. 39 is a side view showing a conventional reaction container.

Namely, the mouth of the container 401 in which the reagent C has been placed in advance is sealed with a lid 407 (septum) like that shown in FIGS. 38(a) and 38(b), which prevents spillage or vaporization of the reagent C during transportation of the container 401. The lid 407 is made up of, for example, a cylindrical cap section 407a made of polyethylene, etc., one surface of which is sealed by a very thin Teflon sheet 407b of approximately 2 µm. Then, when the reagent D is to be introduced into the container 401, the reagent drip opening 403b of the introducing tube 402 breaks the Teflon sheet and is inserted into the container 401 (see FIG. 36).

By this means, when assembling the reaction container in the synthesis experiment automation system, there is no need to remove the lid 407 from the container 401, and assembly of the reaction container is greatly simplified.

Further, when introducing the reagent D in the synthesis experiment automation system, a needle 408 made of fine tubing (see FIG. 36) is inserted into the inner tube 403 of the introducing tube 402, and the reagent D is introduced by passing it through the fine tubing of the needle 408. For this reason, it is preferable if the reagent introduction opening 403a of the introducing tube 402 is provided with a funnel-shaped guide section 403d, which guides the needle 408 into the inner tube 403 with certainty.

In addition, the method of using the foregoing reaction container is not limited to the method described above; the reaction container may also be used as follows. For example, instead of using the gas flow intake 403c shown in FIG. 37 for supply of an inert gas, the gas flow intake 403c can be connected to a pump via a trap. By this means, when, for example, the reaction produces a poisonous gas, if the pump is used to apply suction to the gas flow intake 403c, the poisonous gas produced can be prevented from escaping into the atmosphere through the reagent introduction opening 403a.

Incidentally, when it is used in the synthesis experiment automation system, the container 401 is provided with a cylindrical shape, in order to make it easy for the robot to transport, but the present invention is not limited to this shape. Neither are the capacity or material of the container 401 limited to any particular capacity or material.

The embodiments and concrete examples of implementation discussed in the foregoing explanation of the present invention serve solely to illustrate the technical contents of the present invention, which should not be narrowly interpreted within the limits of such concrete examples, but rather may be applied in many variations without departing from the spirit of the present invention and the scope of the patent claims set forth below.

INDUSTRIAL APPLICABILITY

With the synthesis experiment automation system according to the present invention, since the computer controls the actions of the various devices in the reaction system separately for each synthesis reaction experiment, each reaction section in the reaction device can be operated under different experiment conditions. For example, if each of the reaction sections in the reaction device is provided with a temperature regulating means, and the temperature regulating operations of each of the temperature regulating means are controlled by the computer, a plurality of synthesis reactions can be carried out simultaneously under different temperature conditions.

Further, since each reaction section can hold a plurality of reaction containers, synthesis reactions can be carried out under even more different experiment conditions.

In addition, since the actions of the robot in transporting and placing reaction containers are also controlled by the computer, the robot transports the reaction containers within the reaction system in accordance with the experiment conditions for each synthesis reaction. Consequently, the synthesis experiment automation system is easily extendable merely by placing more reaction system devices within the robot's range of action.

Moreover, since the computer controls the transporting and placing actions of the robot and the operations of the devices of the reaction system separately for the experiment conditions for each synthesis reaction, the synthesis experiment automation system can respond flexibly to different kinds of synthesis reactions, and the reaction process can be freely rearranged. Consequently, the flexibility of the system can be improved.

In order to carry out, as described above, a plurality of experiments simultaneously, it is sufficient if, for example, the synthesis reaction steps to be executed by the reaction system are set by the computer separately for each synthesis reaction experiment.

In addition, the foregoing reaction system may be further provided with a shaking device, which shakes a reaction container immediately after completion of the reaction in the reaction device, under conditions set in accordance with the experiment conditions of the reaction; and with a separation processing device, which, after shaking by the shaking device, separates an indicated solution from the reaction solutions in the reaction container. In this case, by placing the shaking device and the separation processing device within the range of action of the robot, these two devices can be operated in the reaction system in accordance with the experiment conditions for each synthesis reaction.

Again, with the synthesis experiment automation system according to the present invention, by providing the shaking device for shaking the reaction containers with a gas venting structure for discharging gas produced by the reaction, the reaction containers can be prevented from bursting due to gas produced during shaking. Furthermore, by providing the shaking device with a washing section for washing the side of reaction container lids which face the interior thereof, any reaction solution splashing thereon can be prevented from becoming mixed with a subsequent reaction solution when the lid is used for a subsequent experiment.

Further, with the synthesis experiment automation system according to the present invention, the interface of a reaction liquid which has separated into layers is detected by a difference in the electrical conductivity of each layer. Thus it is not necessary to perform light scanning from outside the reaction container with a refractive index detecting sensor, etc., as it is when the interface of the reaction liquid is detected using a difference in the refractive indices of the respective layers. Accordingly, increase of the size of the device can be prevented.

In this case, separation of the reaction liquid can be performed using an extracting means which extracts from the reaction liquid one of the solutions which have separated into layers.

Further, with the synthesis experiment automation system according to the present invention, since the robot travels along an extendable rail, by positioning the various devices of the reaction system along the rail, reaction containers can be efficiently transported by the robot. Moreover, since the rail is extendable, the system can easily be extended by merely extending the rail. Accordingly, since various devices to be used in synthesis reactions can be freely added, a synthesis experiment automation system can be provided which has great extendibility, and which is able to respond to experiment conditions for different types of synthesis reactions.

With the separation processing device according to the present invention, since the position detecting means detects the positions of a liquid level and an interface of a solution phase made up of two incompatible solutions which have separated into layers using an image of the solution phase, the operations of detecting the liquid level and the interface can be performed automatically.

Further, based on the results obtained by the position detecting means, i.e., the liquid level and interface positions detected thereby, a solution extracting means calculates the quantities of the upper- and lower-layer solutions and extracts one or both of the upper- and lower-layer solutions. Accordingly, solution extraction can be automated.

In this way, since the liquid level and interface positions can be automatically detected by the position detecting means using the image of the solution phase read by the reading means, and since, further, the solutions in the solution phase can be automatically extracted by the solution extracting means based on the results obtained by the position detecting means, the foregoing separation processing device is suitable for use in a device which performs organic synthesis reactions automatically. Consequently, a device for performing organic synthesis reactions automatically can be fully automated.

With the reaction container according to the present invention, when allowing a first reagent and a second reagent to react, the first reagent is placed in the container section in advance. Then, the second reagent is introduced into the container section through the introducing tube. At this time, the second reagent passes through the inner tube of the introducing tube. During reaction, vaporized components produced in the container attempt to escape through the inner tube of the introducing tube, but these vaporized components are cooled by a coolant (water, for example) passing between the inner tube and the wall of the outer tube, and are thus liquefied and returned to the interior of the container. Further, in order to seal the container under open pressure by isolating it from the atmosphere, an inert gas (nitrogen, for example) is supplied from the gas flow intake provided in the wall of the upper part of the introducing tube, and the inert gas flows through and fills the upper part of the inner tube, and is released from the upper opening of the introducing tube.

Incidentally, the terms "first reagent" and "second reagent" do not necessarily indicate single chemical compounds, and in some cases, two or more compounds will be mixed together. Again, the first and second reagents may each be mixed with a reaction solvent, or a reaction solvent may be placed in the container section in advance.

With the foregoing reaction container, the reagent introducing section, cooling section, and seal section, which were conventionally provided separately on the container section, can be combined into a single member, and thus a reaction container which is more compact, and which is easy to assemble, can be obtained.

In this way, assembly of the reaction container is no longer troublesome, as was the case in the past, and thus the reaction container is suitable for use in a device for performing reaction experiments automatically (the synthesis experiment automation system).

What is claimed is:

1. A synthesis experiment automation system comprising:
    a reaction system, which includes
        a reaction container rack for storing a plurality of reaction containers;
        a dispensing device for introducing reagents and solvents into said reaction containers;
        a reaction device made up of a plurality of reaction sections, each of which stores a plurality of said reaction containers containing reagents and/or solvents, and each of said reaction containers settable to simultaneously perform synthesis reactions under experiment conditions which are independent of the experiment conditions for the other of said reaction containers;
        a shaking device, which shakes a said reaction container immediately after completion of the synthesis reaction in said reaction device, under conditions set in accordance with the experiment conditions of the synthesis reaction, wherein said shaking device includes:
            a shaking section, which shakes said reaction container,
            a lid section, which prevents spillage of liquid during shaking, and which has a gas venting structure for discharging gas produced during shaking, and
            a washing section, which washes a surface of said lid section facing toward the interior of said reaction container;
        a separation processing device, which, after shaking by said shaking device, separates an indicated solution from reaction solutions in said reaction container; and
        an extendible rail, wherein said reaction container rack, dispensing device, and reaction device are positioned beside the rail;
    analyzing means for analyzing reaction products obtained in said reaction device;
    an industrial robot, which
        removes said reaction containers from said reaction container rack and transports said reaction containers to a dispensing position of said dispensing device, transports said reaction containers containing reagents and/or solvents to predetermined positions in said reaction sections of said reaction device, and
        supplies to said analyzing means reaction products produced in said reaction device,
        wherein the industrial robot has a main body provided with an arm having a polycentric joint that turns freely on the body, and wherein the industrial robot travels through the reaction system along the extendible rail;
    a computer, which controls
        the actions of said robot in transporting and placing said reaction containers.
        the operations of said dispensing device and said reaction device of said reaction system, and
        analysis operations of said analyzing means, in accordance with the experiment conditions of each synthesis reaction; and
        wherein said computer sets synthesis reaction steps to be executed by said reaction system independently for each synthesis reaction experiment performed in each reaction section, and wherein each reaction section is provided with a temperature regulator to set reaction temperature independently.

2. A synthesis experiment automation system comprising:
    a reaction system, which includes
        a reaction container rack for storing a plurality of reaction containers;
        a dispensing device for introducing reagents and solvents into said reaction containers;
        a reaction device made up of a plurality of reaction sections, each of which stores a plurality of said reaction containers containing reagents and/or solvents, and each of said reaction containers settable to simultaneously perform synthesis reactions under experiment conditions which are independent of the experiment conditions for the other of said reaction containers;
a shaking device, which shakes a said reaction container immediately after completion of the synthesis reaction in said reaction device, under conditions set in accordance with the experiment conditions of the synthesis reaction;
a separation processing device, which, after shaking by said shaking device, separates an indicated solution from reaction solutions in said reaction container;
wherein said separation processing device includes a sensor which detects an interface of a reaction liquid which has separated into layers using a difference in electrical conductivities of the respective layers, and said separation processing device performs separation based on the detected results; and
an extendible rail, wherein said reaction container rack, dispensing device, and reaction device are positioned beside the rail:
analyzing means for analyzing reaction products obtained in said reaction device;
an industrial robot, which
removes said reaction containers from said reaction container rack and
transports said reaction containers to a dispensing position of said dispensing device,
transports said reaction containers containing reagents and/or solvents to predetermined positions in said reaction sections of said reaction device, and
supplies to said analyzing means reaction products produced in said reaction device,
wherein the industrial robot has a main body provided with an arm having a polycentric joint that turns freely on the body, and wherein the industrial robot travels through the reaction system along the extendible rail;
a computer, which controls
the actions of said robot in transporting and placing said reaction containers,
the operations of said dispensing device and said reaction device of said reaction system, and
analysis operations of said analyzing means, in accordance with the experiment conditions of each synthesis reaction; and
wherein said computer sets synthesis reaction steps to be executed by said reaction system independently for each synthesis reaction experiment performed in each reaction section, and wherein each reaction section is provided with a temperature regulator to set reaction temperature independently.

3. The synthesis experiment automation system set forth in claim 2, wherein:
said separation processing device includes extracting means, which, based on the results detected by said sensor, extract from the reaction liquid one of the solutions which have separated into layers.

4. A synthesis experiment automation system comprising:
a reaction system, which includes
a reaction container rack for storing a plurality of reaction containers;
a dispensing device for introducing reagents and solvents into said reaction containers;
a reaction device made up of a plurality of reaction sections, each of which stores a plurality of said reaction containers containing reagents and/or solvents, and each of said reaction containers settable to simultaneously perform synthesis reactions under experiment conditions which are independent of the experiment conditions for the other of said reaction containers:
a shaking device, which shakes a said reaction container immediately after completion of the synthesis reaction in said reaction device, under conditions set in accordance with the experiment conditions of the synthesis reaction;
a separation processing device, which, after shaking by said shaking device, separates an indicated solution from reaction solutions in said reaction container,
wherein said separation processing device comprises:
reading means, which read as an image a solution phase made up of two incompatible solutions which have separated into layers; position detecting means, which detect positions of a liquid level and an interface of the solution phase from the image read by said reading means; and
solution extracting means, which, based on the results detected by said detecting means, calculate the quantities of the solutions on the upper and lower layers of the solution phase, and extract one or both of the upper- and lower-level solutions; and
an extendible rail, wherein said reaction container rack, dispensing device, and reaction device are positioned beside the rail;
analyzing means for analyzing reaction products obtained in said reaction device;
an industrial robot, which
removes said reaction containers from said reaction container rack and
transports said reaction containers to a dispensing position of said dispensing device,
transports said reaction containers containing reagents and/or solvents to predetermined positions in said reaction sections of said reaction device, and
supplies to said analyzing means reaction products produced in said reaction device,
wherein the industrial robot has a main body provided with an arm having a polycentric joint that turns freely on the body, and wherein the industrial robot travels through the reaction system along the extendible rail;
a computer, which controls
the actions of said robot in transporting and placing said reaction containers,
the operations of said dispensing device and said reaction device of said reaction system, and
analysis operations of said analyzing means, in accordance with the experiment conditions of each synthesis reaction; and
wherein said computer sets synthesis reaction steps to be executed by said reaction system independently for each synthesis reaction experiment performed in each reaction section, and wherein each reaction section is provided with a temperature regulator to set reaction temperature independently.

5. A synthesis experiment automation system comprising:
a reaction system, which includes
a reaction container rack forth a plurality of reaction containers, wherein said reaction container comprises a container section, in which a first reagent is placed in advance, and an introducing tube, which introduces a second reagent into said container section, said introducing tube comprising:
- a cooling section having an inner tube for introducing the second reagent, and an outer tube which surrounds an outer wall of said inner tube, with a cooling medium being passed through said outer tube, so as to cool vapor components passing through said inner tube,
- a reagent introducing section, which introduces the second reagent from an upper opening of said inner tube, and thence into said container section from a lower opening of said inner tube, and
- a seal section, which supplies a gas from a gas flow intake branching from a wall of an upper part of said inner tube;

a dispensing device for introducing reagents and solvents into said reaction containers;

a reaction device made up of a plurality of reaction sections, each of which stores a plurality of said reaction containers containing a reagents and/or solvents, and each of said reaction containers settable to simultaneously perform synthesis reactions under experiment conditions which are independent of the experiment conditions for the other of said reaction containers; and an extendible rail, wherein said reaction container rack, dispensine device, and reaction device are positioned beside the rail;

analyzing means for analyzing, reaction products obtained in said reaction device;

an industrial robot, which
- removes said reaction containers from said reaction container rack and
- transports said reaction containers to a dispensing position of said dispensing device,
- transports said reaction containers containing reagents and/or solvents to predetermined positions in said reaction sections of said reaction device, and
- supplies to said analyzing means reaction products produced in said reaction device,
- wherein the industrial robot has a main body provided with an arm having a polycentric joint that turns freely on the body, and wherein the industrial robot travels through the reaction system along the extendible rail;

a computer, which controls
- the actions of said robot in transporting and placing said reaction containers,
- the operations of said dispensing device and said reaction device of said reaction system, and
- analysis operations of said analyzing means, in accordance with the experiment conditions of each synthesis reaction; and
- wherein said computer sets synthesis reaction steps to be executed by said reaction system independently for each synthesis reaction experiment performed in each reaction section, and wherein each reaction section is provided with a temperature regulator to set reaction temperature independently.

6. A synthesis experiment automation system comprising:

a reaction system, which includes
- a reaction container rack for storing a plurality of reaction containers;
- a dispensing device for introducing reagents and solvents into said reaction containers;
- a reaction device made up of a plurality of reaction sections, each of which stores a plurality of said reaction containers containing reagents and/or solvents, and each of said reaction containers settable to simultaneously perform synthesis reactions under experiment conditions which are independent of the experiment conditions for the other of said reaction containers;
- a shaking device, which shakes a said reaction container immediately after completion of the synthesis reaction in said reaction device, under conditions set in accordance with the experiment conditions of the synthesis reaction;
- a separation processing device, which, after shaking by said shaking device, separates an indicated solution from reaction solutions in said reaction container, wherein said separation processing device comprises:
  - reading means, which read as an image a solution phase made up of two incompatible solutions which have separated into layers, and
  - position detecting means, which detect positions of a liquid level and an interface of the solution phase from the image read by said reading means; and
- an extendible rail, wherein said reaction container rack, dispensing device, and reaction device are positioned beside the rail;

analyzing means for analyzing reaction products obtained in said reaction device;

an industrial robot, which
- removes said reaction containers from said reaction container rack and
- transports said reaction containers to a dispensing position of said dispensing device,
- transports said reaction containers containing reagents and/or solvents to predetermined positions in said reaction sections of said reaction device, and
- supplies to said analyzing means reaction products produced in said reaction device,
- wherein the industrial robot has a main body provided with an arm having a polycentric joint that turns freely on the body, and wherein the industrial robot travels through the reaction system along the extendible rail;

a computer, which controls
- the actions of said robot in transporting and placing said reaction containers,
- the operations of said dispensing device and said reaction device of said reaction system, and
- analysis operations of said analyzing means, in accordance with the experiment conditions of each synthesis reaction; and
- wherein said computer sets synthesis reaction steps to be executed by said reaction system independently for each synthesis reaction experiment performed in each reaction section, and wherein each reaction section is provided with a temperature regulator to set reaction temperature independently.

7. A synthesis experiment automation system comprising:

a reaction system, which includes
- a reaction container rack for storing a plurality of reaction containers;
- a dispensing device for introducing reagents and solvents into said reaction containers; and
- a reaction device made up of a plurality of reaction sections, each of which stores a plurality of said reaction containers containing reagents and/or solvents, and each of said reaction containers settable to simultaneously perform synthesis reactions under experiment conditions which are independent of the experiment conditions for the other of said reaction containers;

an extendible rail, wherein said reaction container rack, dispensing device, and reaction device are positioned beside the rail;

a shaking device, which shakes a said reaction container immediately after said completion of the synthesis reaction in said reaction device, under conditions set in accordance with the experiment conditions of the synthesis reaction; and a separating processing device, which, after shaking by said shaking device, separates an indicated solution from reaction solutions in said reaction container, wherein the separating processing device comprises:

reading means, which read as an image a solution phase made up of two incompatible solutions which have separated into layers;

position detecting means, which detect positions of a liquid level and an interface of the solution phase from the image read by said reading means, wherein said position detecting means comprise:

an image pattern recording section, which records a plurality of image patterns showing a liquid level position and an interface position of a solution phase made up of two incompatible solutions which have separated into layers; and position calculating section, which approximates, from among other the image patterns recorded in said image pattern recording section, liquid level and interface positions shown in the image read by said reading means, and calculates the liquid level and interface positions shown in the image read by reading means based on the approximate positions; and solution extracting means, which, based on the results detected by said detecting means, calculate the quantities of the solutions on the upper and lower layers of the solution phase, and extract one or both of the upper- and lower-level solutions;

analyzing means for analyzing reaction products obtained in said reaction device;

an industrial robot, which removes said reaction containers from said reaction container rack and transports said reaction containers to a dispensing position of said dispensing device, transports said reaction containers containing reagents and/or solvents to predetermined positions in said reaction sections of said reaction device, and supplies to said analyzing means reaction products produced in said reaction device, wherein the industrial robot has a main body provided with an arm having a polycentric joint that turns freely on the body, and wherein the industrial robot travels through the reaction system along the extendible rail;

a computer, which controls the actions of said robot in transporting and placing said reaction containers, the operations of said dispensing device and said reaction device of said reaction system, and analysis operations of said analyzing means, in accordance with the experiment conditions of each synthesis reaction; and wherein said computer sets synthesis reaction steps to be executed by said reaction system independently for each synthesis reaction experiment performed in each reaction section, and wherein each reaction section is provided with a temperature regulator to set reaction temperature of each said reaction section independently.

8. A synthesis experiment automation system comprising:

a reaction system, which includes a reaction container rack for storing a plurality of reaction containers;

a dispensing device for introducing reagents and solvents into said reaction containers; and a reaction device made up of a plurality of reaction sections, each of which stores a plurality of said reaction containers containing reagents and/or solvents, and each of said reaction containers settable to simultaneously perform synthesis reactions under experiment conditions which are independent of the experiment conditions for the other of said reaction containers;

an extendible rail, wherein said reaction container rack, dispensing device, and reaction device are positioned beside the rail;

a shaking device, which shakes a said reaction container immediately after said completion of the synthesis reaction in said reaction device, under conditions set in accordance with the experiment conditions of the synthesis reaction; and a separating processing device, which, after shaking by said shaking device, separates an indicated solution from reaction solutions in said reaction container, wherein the separating processing device comprises:

reading means, which read as an image a solution phase made up of two incompatible solutions which have separated into layers, wherein the solution phase made up of two incompatible solutions which have separated into layers is contained in a transparent container, and a tape of uniform width is provided in the direction of the height of said container, so as to cross the liquid level and the interface of the solution phase;

position detecting means, which detect positions of a liquid level and an interface of the solution phase from the image read by said reading means, wherein said reading means read the solution phase as an image, from a position such that said transparent container is between said reading means and said tape; and solution extracting means, which, based on the results detected by said detecting means, calculate the quantities of the solutions on the upper and lower layers of the solution phase, and extract one or both of the upper- and lower-level solutions;

analyzing means for analyzing reaction products obtained in said reaction device;

an industrial robot, which removes said reaction containers from said reaction container rack and transports said reaction containers to a dispensing position of said dispensing device, transports said reaction containers containing reagents and/or solvents to predetermined positions in said reaction sections of said reaction device, and supplies to said analyzing means reaction products produced in said reaction device, wherein the industrial robot has a main body provided with an arm having a polycentric joint that turns freely on the body, and wherein the industrial robot travels through the reaction system along the extendible rail;

a computer, which controls
the actions of said robot in transporting and placing said reaction containers,
the operations of said dispensing device and said reaction device of said reaction system, and
analysis operations of said analyzing means, in accordance with the experiment conditions of each synthesis reaction; and wherein said computer sets synthesis reaction steps to be executed by said reaction system independently for each synthesis reaction experiment performed in each reaction section, and wherein each reaction section is provided with a temperature regulator to set reaction temperature independently.

* * * * *